(12) United States Patent
Tomoda et al.

(10) Patent No.: US 9,896,456 B2
(45) Date of Patent: Feb. 20, 2018

(54) PHARMACEUTICAL COMPOUND HAVING INHIBITORY ACTIVITY AGAINST CHOLESTEROL ACYLTRANSFERASE ISOZYME 2 (ACAT2)

(71) Applicant: School Juridical Person Kitasato Institute, Tokyo (JP)

(72) Inventors: Hiroshi Tomoda, Sagamihara (JP); Masaki Ohtawa, Sagamihara (JP); Satoshi Omura, Sagamihara (JP); Tohru Nagamitsu, Sagamihara (JP)

(73) Assignee: School Juridical Person Kitasato Institute, Tokyo (JP)

( * ) Notice: Subject to any disclaimer, the term of this patent is extended or adjusted under 35 U.S.C. 154(b) by 0 days.

(21) Appl. No.: 15/320,834

(22) PCT Filed: Jun. 18, 2015

(86) PCT No.: PCT/JP2015/067636
§ 371 (c)(1),
(2) Date: Dec. 21, 2016

(87) PCT Pub. No.: WO2015/198966
PCT Pub. Date: Dec. 30, 2015

(65) Prior Publication Data
US 2017/0204114 A1  Jul. 20, 2017

(30) Foreign Application Priority Data
Jun. 24, 2014  (JP) ................. 2014-129126

(51) Int. Cl.
*C07D 493/04*  (2006.01)
(52) U.S. Cl.
CPC ................. *C07D 493/04* (2013.01)
(58) Field of Classification Search
CPC ................................. C07D 493/04
USPC ....................................... 549/283
See application file for complete search history.

(56) References Cited

U.S. PATENT DOCUMENTS

| | | |
|---|---|---|
| 6,916,824 B1 | 7/2005 | Hua et al. |
| 2011/0184173 A1 | 7/2011 | Tomoda et al. |
| 2013/0085163 A1 | 4/2013 | Tomoda et al. |

FOREIGN PATENT DOCUMENTS

| | | |
|---|---|---|
| JP | 08-291164 | 11/1996 |
| JP | 2014-144922 | 8/2014 |
| WO | 2009/081957 | 7/2009 |
| WO | 2010/150739 | 12/2010 |
| WO | 2011/122468 | 10/2011 |

OTHER PUBLICATIONS

Libby, Peter "The Forgotten Majority—Unfinished Business in Cardiovascular Risk Reduction", Journal of the American College of Cardiology, 2005, vol. 46, No. 7, pp. 1225-1228.

Roth, Bruce D., "ACAT Inhibitors: Evolution from Cholesterol-Absorption Inhibitors to Antiatherosclerotic Agents", Drug Discovery Today, Jan. 1998, vol. 3, No. 1, pp. 19-24.

Meuwese, Marijn C., et al., "And Then There Were Acyl Coenzyme A:cholesterol Acyl Transferase Inhibitors", Current Opinion in Lipidology, 2006, vol. 17, pp. 426-431.

Chang, Catherine, et al., "Human Acyl-CoA:cholesterol Acyltransferase (ACAT) and its Potential as a Target for Parmaceutical Intervention Againse Atherosclerosis", Acta Biochimica et Biophysica Sinica, 2006, vol. 38, No. 3, pp. 151-156.

Farese, Robert V., Jr., "The Nine Lives of ACAT Inhibitors", Arteriosclerosis, Thrombosis, and Vascular Biology, Journal of the American Heart Association, 2006, vol. 26, pp. 1684-1686.

Yagyu, Hiroaki, et al., "Absence of ACAT-1 Attenuates Atherosclerosis but Causes Dry Eye and Cutaneous Xanthomatosis in Mice with Congential and Hyperlipidemia", The Journal of Biological Chemistry, Jul. 14, 2000, vol. 275, No. 28, pp. 21324-21330.

Accad, Michel, et al., "Massive Xanthomatosis and Altered Composition of Atherosclerotic Lesions in Hyperlipidemic Mice Lacking Acyl CoA:cholesterol Acyltransferase 1", The Journal of Clinical Investigation, Mar. 2000, vol. 105, No. 6, pp. 711-719.

Buhman, Kimberly K., et al., "Resistance to Diet-Induced Hypercholesterolemia and Gallstone Formation in ACAT2-Deficient Mice", Nature Medicine, Dec. 2000, vol. 6. No. 12, pp. 1341-1347.

Ohshiro, Taichi, et al., "Isoform-Specific Inhibitors of ACATs: Recent Advances and Promising Developments", Future Medicinal Chemistry, 2011, vol. 3, No. 16, pp. 2039-2061.

Tomoda, Hiroshi, et al., "Pyripyropenes, Novel Inhibitors of ACYL-CoA: Cholesterol Acyltransferase Produced by Aspergillus Fumigatus", The Journal of Antibiotics, Feb. 1994, vol. 47, No. 2, pp. 148-153.

(Continued)

*Primary Examiner* — Rita J Desai
(74) *Attorney, Agent, or Firm* — McCarter & English, LLP

(57) ABSTRACT

This invention provides a novel non-natural pharmaceutical compound having a different mechanism than statin drugs and having a selective inhibitory activity against ACAT2. This invention relates to the compound represented by Formula (I), a salt thereof, or a solvate thereof:

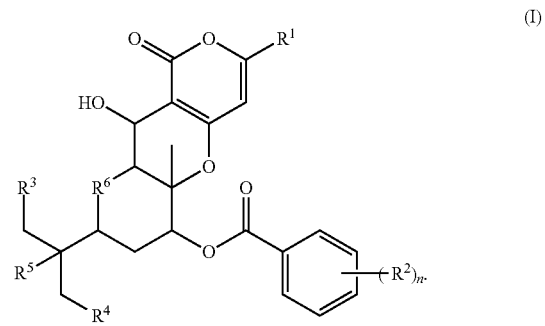

11 Claims, No Drawings

(56) References Cited

OTHER PUBLICATIONS

Bell, Thomas A. III, et al., "Dietary Fat-Induced Alterations in Atherosclerosis Are Abolished by ACAT2-Deficiency in ApoB100 Only, LDLr-/-Mice", Arteriosclerosis, Thrombosis, and Vascular Biology, Journal of the American Heart Association, Jan. 9, 2007, vol. 27, pp. 1396-1402 (with Expanded Materials and Methods Section i-vii).

Ohshiro, Taichi, et al., "Pyripyropene A, an Acyl-Coenzyme A:Cholesteroi Acyltransferase 2-Selective Inhibitor, Attenuates Hypercholesterolemia and Atherosclerosis in Murine Models of Hyperlipidemia" Arteriosclerosis, Thrombosis, and Vascular Biology, Journal of the American Heart Association, 2011, vol. 31, pp. 1108-1115 (with Supplemental Figures and Supplemental Material).

Odani, Atsuki, et al., "Total Synthesis of Pyripyropene A", Tetrahedron, 2011, vol. 67, pp. 8195-8203.

Ohtawa, Masaki, et al., "Structure-Activity Relationship Study and Total Synthesis of Pyripyropene A as a Potent ACA T2-Selective Inhibitor", Journal of Synthetic Organic Chemistry, Japan, 2013, vol. 71, pp. 830-843.

PHARMACEUTICAL COMPOUND HAVING INHIBITORY ACTIVITY AGAINST CHOLESTEROL ACYLTRANSFERASE ISOZYME 2 (ACAT2)

RELATED APPLICATIONS

This application is a national stage application filed under 35 USC 371 of PCT/JP2015/067636, filed Jun. 18, 2015, which claims the benefit of Japanese Patent Application No. 2014-129126, filed Jun. 24, 2014, all of which are incorporated herein, in entirety, by reference.

TECHNICAL FIELD

The present invention relates to a novel pharmaceutical compound having an extremely high degree of inhibitory activity against cholesterol acyltransferase isozyme 2 (hereinafter abbreviated as "ACAT2").

BACKGROUND ART

The number of patients in Japan with arteriosclerosis and hyperlipemia, which are associated with a high risk of high-mortality diseases such as myocardial infarction and cerebral apoplexy, is said to be as many as thirty million, including subjects having no subjective symptoms. Even at the present time, after the Guidelines for Prevention of Atherosclerotic Cardiovascular Diseases have been revised by the Japan Atherosclerosis Society, such diseases rank high among the causes of death in Japan. Arteriosclerosis and hyperlipemia are significant health problems not only in Japan but also in Europe and the Americas.

The drugs that are primarily used at present for prevention and treatment of arteriosclerosis and/or hyperlipemia are statin drugs, which specifically inhibit hydroxy-3-methyl-glutaryl coenzyme A (Co-A) (hereinafter abbreviated as HMG-CoA) reductase. Statin drugs were among the best-selling drugs in the world for 8 consecutive years, starting in 2001. These drugs are widely used, as demonstrated by the fact that two statin drugs ranked among the top thirty drugs having the highest worldwide sales in 2008.

In fact, however, it has been found that statin drugs affect the prevention of onset in only 30% to 40% of patients, and these drugs do not suppress cardiovascular diseases or the like in about half of patients who have received therapy with them (Non-Patent Document 1). The reasons why HMG-CoA reductase inhibitors, such as statin drugs, which are currently used as prophylactic or therapeutic agents for arteriosclerosis, cannot sufficiently suppress cardiovascular diseases or similar diseases are considered to relate to the fact that the mechanism of onset of arteriosclerosis is complicated. Often, arteriosclerosis is considered to develop due to various factors, such as heredity factors, disease history of diabetes or the like, or drug ingestion history, acting in combination. Therefore, diagnosis and treatment should be performed in accordance with the pathological conditions of each patient, so as to prevent or treat arteriosclerosis and/or hyperlipemia. Accordingly, there is an urgent need for the development of a pharmaceutical product having a new mechanism that is different from the mechanism of statin drugs and can be expected to have effects of suppressing the onset of disorders in the coronary artery and/or degenerating lesions in the coronary artery.

Cholesterol acyltransferase (hereinafter abbreviated as ACAT) is expected to serve as a target for a preventive and therapeutic agent for arteriosclerosis and/or hyperlipemia having a new mechanism (Non-Patent Document 2). ACAT is an enzyme that introduces an acyl group into cholesterol. A number of synthetic ACAT inhibitors have heretofore been developed. However, these inhibitors have not yet been put to clinical use due to side effects or insufficient effects (Non-Patent Document 3).

It has recently been revealed that ACAT exists in the form of two isozymes, ACAT1 and ACAT2, which have different in vivo functions and different locations from each other (Non-Patent Document 4). ACAT1 is widely found in many living cells and tissues and is highly expressed particularly in macrophages and smooth muscle cells. Also, ACAT1 is known to cause the formation of foam macrophage cells causing arteriosclerosis on the artery wall. In contrast, ACAT2 is expressed specifically in the small intestine or liver. ACAT2 is considered to be involved in the absorption of dietary cholesterol and the secretion of very low-density lipoproteins in each of these organs.

As described above, ACAT1 and ACAT2 were found to be different with respect to in vivo functions. In the development of new drugs targeting ACAT, accordingly, it is critical to identify the selectivity of ACAT1 and that of ACAT2. For example, synthetic ACAT inhibitors, the development of which had been abandoned, were found to have activity of selectively inhibiting ACAT1 (e.g., Wu-V-23 and K-604) or inhibiting both ACAT1 and ACAT2 isozymes (e.g., avasimibe and pactimibe) (Non-Patent Document 5). Development of such synthetic ACAT inhibitors had been abandoned due to side effects, and ACAT1 knockout mice had developed side effects in the past (Non-Patent Documents 6 and 7). On the contrary, ACAT2 knockout mice exhibited effects of anti-arteriosclerosis (Non-Patent Document 8). As preventive/therapeutic agents against arteriosclerosis and/or hyperlipemia (including lipemia, fatty liver, and obesity), accordingly, the development of drugs from a selective inhibitor against ACAT2, which is an ACAT isozyme, has been strongly desired (Non-Patent Document 9).

As selective ACAT2 inhibitors, a naturally occurring organic compound (that is, pyripyropene A) (Non-Patent Document 10) and pyripyropene A derivatives obtained from pyripyropene A via a semi-synthetic technique (Patent Documents 1 to 3) were found. In addition, anti-arteriosclerotic effects in liver ACAT2 knockout mice achieved with an antisense oligonucleotide (Non-Patent Document 11), anti-arteriosclerotic effects resulting from animal experiments using pyripyropene A (Non-Patent Document 12), and the results of total synthesis of pyripyropene A (Non-Patent Document 13) were reported.

PRIOR ART DOCUMENTS

Patent Documents

Patent Document 1: WO 2009/081957
Patent Document 2: WO 2010/150739
Patent Document 3: WO 2011/122468

Non-Patent Documents

Non-Patent Document 1: Libby et al., J. Am. Coll. Cardiol., Vol. 46, pp. 1225-1228, 2005
Non-Patent Document 2: Roth, Drug Discovery Today, Vol. 3, pp. 19-25, 1998
Non-Patent Document 3: Meuwese et al., Curr. Opin. Lipidol., Vol. 17, pp. 426-431, 2006
Non-Patent Document 4: Chang et al., Acta. Biochim. Biophys. Sin., Vol. 38, pp. 151-156, 2006

Non-Patent Document 5: Farese, Arterioscler. Thromb. Vasc. Biol., Vol. 26, pp. 1684-1686, 2006

Non-Patent Document 6: Yagyu et al., J. Biol. Chem., Vol. 275, pp. 21324-21330, 2000

Non-Patent Document 7: Mccad et al., J. Clin. Invest., Vol. 105, pp. 711-719, 2000

Non-Patent Document 8: Buhman et al., Nat. Med., Vol. 6, pp. 1341-1347, 2000

Non-Patent Document 9: Ohshiro & Tomoda, Future Med. Chem., Vol. 3, pp. 2039-2061, 2011

Non-Patent Document 10: Tomoda et al., J. Antibiot., Vol. 47, pp. 148-153, 1994

Non-Patent Document 11: Bell et al., Arterioscler. Thromb. Vase. Biol., Vol. 27, 1396-1402, 2007

Non-Patent Document 12: Ohshiro et al., Arterioscler. Thromb. Vase. Biol., Vol. 31, pp. 1108-1115, 2011

Non-Patent Document 13: Odani et al., Tetrahedron, Vol. 67, pp. 8195-8203, 2011

Non-Patent Document 14: Masaki Ohtawa et al., Journal of Synthetic Organic Chemistry, Japan, Vol. 71, pp. 830-843, 2013

SUMMARY OF THE INVENTION

Objects to be Attained by the Invention

Atorvastatin, which is a statin-based drug aimed at the prevention and treatment of arteriosclerosis, was developed from a naturally occurring organic compound (i.e., Compactin) by simplifying the chemical structure thereof. The development of Atorvastatin from Compactin is an example from a study aimed at drug development, so as to obtain a novel non-natural pharmaceutical compound from a naturally occurring organic lead compound.

As with the development of Atorvastatin, development of a novel non-natural pharmaceutical compound from a naturally occurring organic lead compound (i.e., pyripyropene A) achieved by simplifying the chemical structure thereof was desired. The present inventors developed a method for synthesizing a compound having the simplified chemical structure of a pyripyropene A ring structure (Non-Patent Document 14). However, it was very difficult to simplify the chemical structure of a lead compound (i.e., pyripyropene A) because of its structural complexity. When developing a novel pharmaceutical compound by simplifying the chemical structure of a naturally occurring lead compound, the resulting compound may exhibit a different structure-activity relationship than a naturally occurring lead compound as a result of such simplified chemical structure. Therefore, no novel non-natural pharmaceutical compound having a high degree of selective inhibitory activity against ACAT2 has been previously developed.

Under the above circumstances, it is an object of the present invention to provide a novel non-natural pharmaceutical compound having a different mechanism than statin drugs and having selective inhibitory activity against ACAT2.

Means for Attaining the Object

The present inventors have examined various means in order to attain the object described above. As a result, the present inventors have discovered that a novel compound having a structure resulting from simplification of the ring structure of an A ring portion of pyripyropene A represented by the formula:

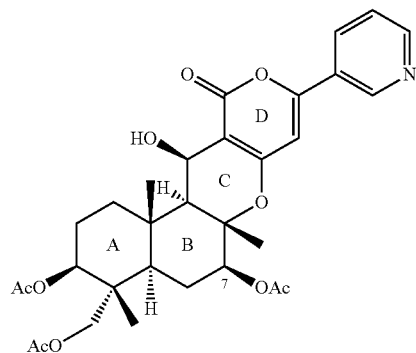

and having a substituted or unsubstituted benzoyloxy group at position 7 would have inhibitory activity against ACAT2 equivalent to that of pyripyropene A. The present inventors have also discovered that such novel compound could be synthesized without the use of pyripyropene A, which is a naturally occurring compound, as a starting material. The present inventors have completed the present invention based on the finding described above.

Specifically, the present invention is summarized as follows.

(1) A compound represented by Formula (I):

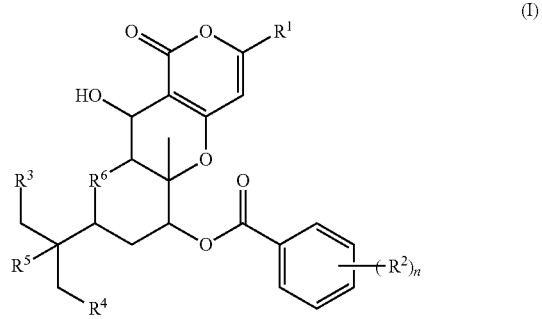

wherein $R^1$ represents substituted or unsubstituted cycloalkyl, substituted or unsubstituted aryl, substituted or unsubstituted heterocycloalkyl, or substituted or unsubstituted heteroaryl;

n is an integer from 0 to 5;

$R^2$ represents halogen, cyano, nitro, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted aryl, substituted or unsubstituted arylalkyl, substituted or unsubstituted arylalkenyl, substituted or unsubstituted heteroaryl, substituted or unsubstituted heteroarylalkyl, substituted or unsubstituted alkoxy, substituted or unsubstituted cycloalkoxy, substituted or unsubstituted heterocycloalkoxy, substituted or unsubstituted aryloxy, substituted or unsubstituted arylalkyloxy, substituted or unsubstituted arylalkenyloxy, substituted or unsubstituted heteroaryloxy, substituted or unsubstituted heteroarylalkyloxy, substituted or unsubstituted acyl, or —$NR^{N1}R^{N2}$, provided that, when n is an integer from 2 or greater, a plurality of $R^2$s may be the same or different;

$R^{N1}$ and $R^{N2}$ each independently represent a monovalent group selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted aryl, substituted or unsubstituted arylalkyl, substituted or unsubstituted arylalkenyl, substituted or unsubstituted heteroaryl, substituted or unsubstituted heteroarylalkyl, substituted or unsubstituted alkoxy, substituted or unsubstituted cycloalkoxy, substituted or unsubstituted heterocycloalkoxy, substituted or unsubstituted aryloxy, substituted or unsubstituted arylalkyloxy, substituted or unsubstituted arylalkenyloxy, substituted or unsubstituted heteroaryloxy, substituted or unsubstituted heteroarylalkyloxy, and substituted or unsubstituted acyl;

$R^3$ and $R^4$ each independently represent hydrogen, hydroxyl, substituted or unsubstituted alkylcarbonyloxy, substituted or unsubstituted arylcarbonyloxy, or substituted or unsubstituted alkoxy, or $R^3$ and $R^4$ together form $—O—CR^7R^8—O—$;

$R^5$ represents hydrogen, hydroxyl, substituted or unsubstituted alkylcarbonyloxy, substituted or unsubstituted arylcarbonyloxy, or substituted or unsubstituted alkoxy;

$R^6$ represents $—C(CH_3)_2—$ or $—CH_2—$; and $R^7$ and $R^8$ each independently represent hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted aryl, substituted or unsubstituted arylalkyl, substituted or unsubstituted arylalkenyl, substituted or unsubstituted heteroaryl, or substituted or unsubstituted heteroarylalkyl, or a salt thereof, or a solvate thereof.

(2) The compound according to (1), wherein $R^1$ represents substituted or unsubstituted aryl or substituted or unsubstituted heteroaryl;

$R^2$ represents halogen, cyano, nitro, substituted or unsubstituted alkyl, substituted or unsubstituted alkenyl, or substituted or unsubstituted alkynyl; and $R^7$ and $R^8$ each independently represent hydrogen, substituted or unsubstituted alkyl, substituted or unsubstituted alkenyl, substituted or unsubstituted alkynyl, or substituted or unsubstituted aryl.

(3) The compound according to (1) or (2), wherein $R^2$ represents a cyano group.

(4) The compound according to any of (1) to (3), wherein n is the integer 1; and $R^2$ represents a 4-cyano group.

(5) A method for producing the compound according to any of (1) to (4) comprising:

a step of epoxidation epoxidizing a compound represented by Formula (II):

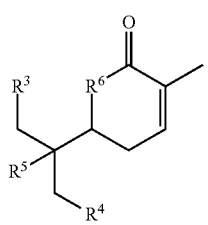

(II)

wherein $R^3$, $R^4$, $R^5$, and $R^6$ are as defined in any of (1) to (4) above, to obtain a compound represented by Formula (III):

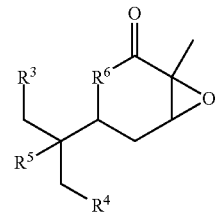

(III)

wherein $R^3$, $R^4$, $R^5$, and $R^6$ are as defined above;

a step of aldehyde group introduction introducing an aldehyde group into the compound represented by Formula (III) obtained by the step of epoxidation to obtain a compound represented by Formula (IV):

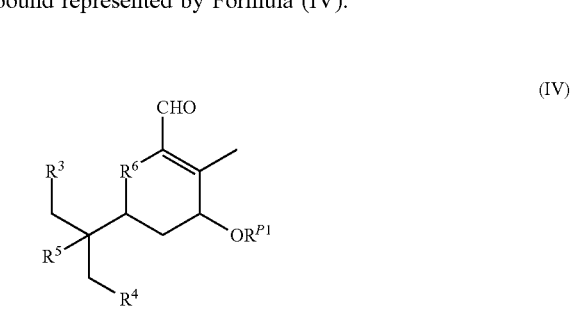

(IV)

wherein $R^3$, $R^4$, $R^5$, and $R^6$ are as defined above, and $R^{P1}$ represents a hydroxyl protecting group;

a step of C ring introduction increasing the number of carbon atoms of the compound represented by Formula (IV) obtained by the step of aldehyde group introduction and subjecting it to cyclization, so as to obtain a compound represented by Formula (V):

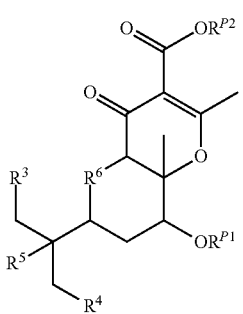

(V)

wherein $R^3$, $R^4$, $R^5$, $R^6$, and $R^{P1}$ are as defined above, and $R^{P2}$ represents a carboxylic acid protecting group;

a step of D ring introduction subjecting the compound represented by Formula (V) obtained by the step of C ring introduction to cyclization, so as to obtain a compound represented by Formula (VII):

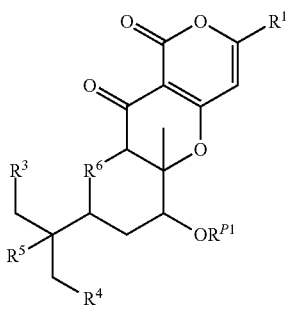

(VII)

wherein
$R^1$ is as defined in any of (1) to (4) above, and
$R^3$, $R^4$, $R^5$, $R^6$, and $R^{P1}$ are as defined above;
a step of benzoyl group introduction allowing the compound represented by Formula (VII) obtained by the step of D ring introduction to react with a compound represented by Formula (VIII):

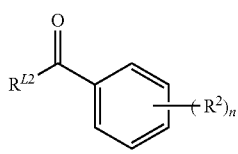

(VIII)

wherein
$R^2$ and n are as defined above; and
$R^{L2}$ represents a carboxylic acid protecting group, to obtain a compound represented by Formula (IX):

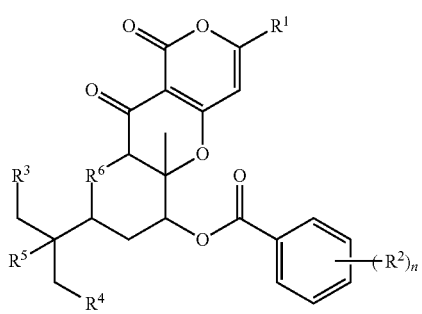

(IX)

wherein $R^1$, $R^2$, $R^3$, $R^4$, $R^5$, $R^6$, and n are as defined above; and
a step of reduction reducing a carbonyl group at position 10 of the compound represented by Formula (IX) obtained by the step of benzoyl group introduction to obtain the compound represented by Formula (I).

(6) An ACAT2 inhibitor comprising, as an active ingredient, the compound according to any of (1) to (4) or a salt thereof, or a solvate thereof.

(7) A medicament comprising, as an active ingredient, the compound according to any of (1) to (4) or a pharmaceutically acceptable salt thereof, or a pharmaceutically acceptable solvate thereof.

(8) A pharmaceutical composition comprising the compound according to any of (1) to (4) or a pharmaceutically acceptable salt thereof, or a pharmaceutically acceptable solvate thereof, and one or more pharmaceutically acceptable carriers.

(9) The medicament according to (7) for use in prevention or treatment of one or more diseases or symptoms selected from the group consisting of hyperlipemia, arteriosclerosis, hypertension, fatty liver, and obesity.

(10) The pharmaceutical composition according to (8) for use in prevention or treatment of one or more diseases or symptoms selected from the group consisting of hyperlipemia, arteriosclerosis, hypertension, fatty liver, and obesity.

(11) A method for prevention or treatment of diseases or symptoms selected from the group consisting of hyperlipemia, arteriosclerosis, hypertension, fatty liver, and obesity comprising administering an effective amount of the compound according to any of (1) to (4) or a pharmaceutically acceptable salt thereof, or a pharmaceutically acceptable solvate thereof to a subject who is in need of prevention or treatment of the diseases or symptoms.

(12) The compound according to any of (1) to (4) or a salt thereof, or a solvate thereof for use in prevention or treatment of diseases or symptoms.

(13) The compound according to (12) or a salt thereof, or a solvate thereof, wherein the diseases or symptoms are one or more diseases or symptoms selected from the group consisting of hyperlipemia, arteriosclerosis, hypertension, fatty liver, and obesity.

(14) Use of the compound according to any of (1) to (4) or a pharmaceutically acceptable salt thereof, or a pharmaceutically acceptable solvate thereof for the manufacture of a medicament for prevention or treatment of one or more diseases or symptoms selected from the group consisting of hyperlipemia, arteriosclerosis, hypertension, fatty liver, and obesity.

Effects of the Invention

The present invention can provide a novel non-natural pharmaceutical compound having a different mechanism than statin drugs and having a selective inhibitory activity against ACAT2.

The objects, the constitutions, and the effects other than those described above are clarified with reference to the embodiments described below.

This description includes part or all of the content as disclosed in the description and/or drawings of Japanese Patent Application No. 2014-129126, which is a priority document of the present application.

EMBODIMENTS FOR CARRYING OUT THE INVENTION

Hereafter, preferable embodiments of the present invention are described in detail.
<1. Novel Compound>

The term "alkyl" used herein refers to a linear or branched saturated aliphatic hydrocarbon group having a particular number of carbon atoms. For example, the term "$C_1$ to $C_5$ alkyl" refers to a linear or branched saturated aliphatic hydrocarbon group having at least 1 and at most 5 carbon atoms. Preferable examples of alkyl include, but are not limited to, linear or branched $C_1$ to $C_5$ alkyl, such as methyl, ethyl, n-propyl, isopropyl, n-butyl, sec-butyl, isobutyl, tert-butyl, and n-pentyl.

The term "alkenyl" used herein refers to a group resulting from substitution of at least 1 C—C single bond of the alkyl with a double bond. Preferable examples of alkenyl include, but are not limited to, linear or branched $C_2$ to $C_5$ alkenyl, such as vinyl, 1-propenyl, allyl, 1-methylethenyl (isopropenyl), 1-butenyl, 2-butenyl, 3-butenyl, 1-methyl-2-propenyl, 2-methyl-2-propenyl, 1-methyl-1-propenyl, 2-methyl-1-propenyl, and 1-pentenyl.

The term "alkynyl" used herein refers to a group resulting from substitution of at least 1 C—C single bond of the alkyl with a triple bond. Preferable examples of alkynyl include, but are not limited to, linear or branched $C_2$ to $C_5$ alkynyl, such as ethynyl, 1-propynyl, 2-propynyl, 1-butynyl, 2-butynyl, 3-butynyl, 1-methyl-2-propynyl, and 1-pentynyl.

The term "cycloalkyl" used herein refers to alicyclic alkyl having a particular number of carbon atoms. For example, the term "$C_3$ to $C_6$ cycloalkyl" refers to a cyclic hydrocarbon group having at least 3 and at most 6 carbon atoms. Preferable examples of cycloalkyl include, but are not limited to, $C_3$ to $C_6$ cycloalkyl, such as cyclopropyl, cyclobutyl, cyclopentyl, and cyclohexyl.

The term "cycloalkenyl" used herein refers to a group resulting from substitution of at least 1 C—C single bond of the cycloalkyl with a double bond. Preferable examples of cycloalkenyl include, but are not limited to, $C_3$ to $C_6$ cycloalkenyl, such as cyclobutenyl, cyclopentenyl, and cyclohexenyl.

The term "cycloalkynyl" used herein refers to a group resulting from substitution of at least 1 C—C single bond of the cycloalkyl with a triple bond. Preferable examples of cycloalkynyl include, but are not limited to, $C_3$ to $C_6$ cycloalkynyl, such as cyclobutynyl, cyclopentynyl, and cyclohexynyl.

The term "heterocycloalkyl" used herein refers to a group resulting from independent substitution of one or more carbon atoms of the cycloalkyl, cycloalkenyl, or cycloalkynyl with a hetero atom selected from among nitrogen (N), sulfur (S), and oxygen (O). In this case, substitution with N or S encompasses substitution with N-oxide, S-oxide, and S-dioxide. Preferable examples of heterocycloalkyl include, but are not limited to, 3- to 6-membered heterocycloalkyl, such as pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, thiomorpholinyl, and piperadinyl.

The term "alkoxy" used herein refers to a group resulting from substitution of the hydrogen atom of hydroxyl with the alkyl, alkenyl, or alkynyl. Preferable examples of alkoxy include, but are not limited to, $C_1$ to $C_5$ alkoxy, such as methoxy, ethoxy, propoxy, butoxy, and pentoxy.

The term "cycloalkoxy" used herein refers to a group resulting from substitution of the hydrogen atom of hydroxyl with the cycloalkyl, cycloalkenyl, or cycloalkynyl. Preferable examples of cycloalkoxy include, but are not limited to, $C_3$ to $C_6$ cycloalkoxy, such as cyclopropoxy, cyclobutoxy, and cyclopentoxy.

The term "heterocycloalkoxy" used herein refers to a group resulting from substitution of the hydrogen atom of hydroxyl with the heterocycloalkyl.

The term "aryl" used herein refers to an aromatic ring group. Examples of preferably aryl include, but are not limited to, $C_6$ to $C_{15}$ aryl, such as phenyl, biphenyl, naphthyl, and anthracenyl.

The term "arylalkyl" used herein refers to a group resulting from substitution of a hydrogen atom of the alkyl with the aryl. Preferable examples of arylalkyl include, but are not limited to, $C_7$ to $C_{16}$ arylalkyl, such as benzyl, 1-phenethyl, and 2-phenethyl.

The term "arylalkenyl" used herein refers to a group resulting from substitution of a hydrogen atom of the alkenyl with the aryl. Preferable examples of arylalkenyl include, but are not limited to, $C_8$ to $C_{17}$ arylalkenyl, such as styryl.

The term "heteroaryl" used herein refers to a group resulting from substitution of each of one or more carbon atoms of the aryl with a hetero atom selected from among nitrogen (N), sulfur (S), and oxygen (O). In this case, substitution with N or S encompasses substitution with N-oxide, S-oxide, and S-dioxide. Preferable examples of heteroaryl include, but are not limited to, 5- to 15-membered heteroaryl, such as furanyl, thienyl (thiophenyl), pyrrolyl, imidazolyl, pyrazolyl, triazolyl, tetrazolyl, thiazolyl, oxazolyl, isooxazolyl, oxadiazolyl, thiadiazolyl, isothiazolyl, pyridyl, pyridazinyl, pyrazinyl, pyrimidinyl, quinolinyl, isoquinolinyl, and indolyl.

The term "heteroarylalkyl" used herein refers to a group resulting from substitution of a hydrogen atom of the alkyl with the heteroaryl. Preferable examples of heteroarylalkyl include, but are not limited to, pyridylmethyl.

The term "aryloxy" used herein refers to a group resulting from substitution of a hydrogen atom of hydroxyl with the aryl. Preferable examples of aryloxy include, but are not limited to, $C_6$ to $C_{15}$ aryloxy, such as phenoxy, biphenyloxy, naphthyloxy, and anthryloxy (anthracenyloxy).

The term "arylalkyloxy" used herein refers to a group resulting from substitution of a hydrogen atom of hydroxyl with the arylalkyl. Preferable examples of arylalkyloxy include, but are not limited to, $C_7$ to $C_{16}$ arylalkyloxy, such as benzyloxy, 1-phenethyloxy, and 2-phenethyloxy.

The term "arylalkenyloxy" used herein refers to a group resulting from substitution of a hydrogen atom of hydroxyl with the arylalkenyl. Preferable examples of arylalkenyloxy include, but are not limited to, $C_8$ to $C_{17}$ arylalkenyloxy, such as styryloxy.

The term "heteroaryloxy" used herein refers to a group resulting from substitution of a hydrogen atom of hydroxyl with the heteroaryl. Preferable examples of heteroaryloxy include, but are not limited to, 5- to 15-membered heteroaryloxy, such as furanyloxy, thienyl oxy (thiophenyloxy), pyrrolyloxy, imidazolyloxy, pyrazolyloxy, triazolyloxy, tetrazolyloxy, thiazolyloxy, oxazolyloxy, isooxazolyloxy, oxadiazolyloxy, thiadiazolyloxy, isothiazolyloxy, pyridyloxy, pyridazinyloxy, pyrazinyloxy, pyrimidinyloxy, quinolinyloxy, isoquinolinyloxy, and indolyloxy.

The term "heteroarylalkyloxy" used herein refers to a group resulting from substitution of a hydrogen atom of hydroxyl with the heteroarylalkyl.

The term "acyl" used herein refers to a group resulting from linking a monovalent group selected from among the groups described above to carbonyl. Preferable examples of acyl include, but are not limited to, $C_1$ to $C_5$ aliphatic acyl, such as formyl, acetyl, and propionyl, and $C_7$ to $C_{16}$ aromatic acyl, such as benzoyl.

The groups described above may independently be unsubstituted or substituted with one or more monovalent groups described above.

The term "halogen" or "halo" used herein refers to fluorine (F), chlorine (Cl), bromine (Br), or iodine (I).

The present invention relates to a compound represented by Formula (I):

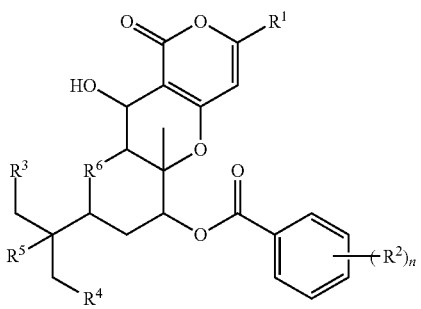

(I)

or a salt thereof, or a solvate thereof.

The present inventors have discovered the compound represented by Formula (I) as a compound having a high degree of selective inhibitory activity against ACAT2. The compound represented by Formula (I) has been designed on the basis of pyripyropene A as a lead compound by simplifying its chemical structure. The compound represented by Formula (I) has a skeleton structure such that an A ring portion of pyripyropene A has been omitted. Because of such simplified chemical structure, the compound represented by Formula (I) can be produced via synthetic means with high purity at low cost.

When developing a novel pharmaceutical compound by simplifying the chemical structure of a naturally occurring compound, in general, the resulting compound may exhibit a different structure-activity relationship than a naturally occurring lead compound as a result of such simplified chemical structure. The present inventors investigated the structure-activity relationship in relation to the inhibitory activity against ACAT2 of compounds each having a skeleton structure in which an A ring portion of pyripyropene A has been omitted. As a result, the present inventors have discovered that the compound represented by Formula (I) having a skeleton structure in which an A ring portion of pyripyropene A has been omitted and having a substituted or unsubstituted benzoyloxy group on a ring corresponding to a B ring of pyripyropene A would exhibit a significantly higher degree of inhibitory activity against ACAT2, compared with a compound having the same skeleton structure but a different group on a ring corresponding to a B ring of pyripyropene A. Because of such structural properties, the compound represented by Formula (I) according to the present invention can exert inhibitory activity on ACAT2 to an equivalent or greater degree than pyripyropene A.

In Formula (I), it is necessary for $R^1$ to represent substituted or unsubstituted cycloalkyl, substituted or unsubstituted aryl, substituted or unsubstituted heterocycloalkyl, or substituted or unsubstituted heteroaryl. $R^1$ preferably represents substituted or unsubstituted $C_3$ to $C_6$ cycloalkyl, substituted or unsubstituted $C_6$ to $C_{15}$ aryl, substituted or unsubstituted 3- to 6-membered heterocycloalkyl, in which case one or more carbon atoms of the heterocycloalkyl may be substituted with one or more heteroatoms selected from among nitrogen (N), sulfur (S), and oxygen (O), or substituted or unsubstituted 5- to 15-membered heteroaryl, in which case one or more carbon atoms of the heteroaryl may be substituted with one or more heteroatoms selected from among nitrogen (N), sulfur (S), and oxygen (O), more preferably substituted or unsubstituted aryl or substituted or unsubstituted heteroaryl, further preferably substituted or unsubstituted $C_6$ to $C_{15}$ aryl or substituted or unsubstituted 5- to 15-membered heteroaryl, in which case one or more carbon atoms of the heteroaryl may be substituted with one or more heteroatoms selected from among nitrogen (N), sulfur (S), and oxygen (O), particularly preferably substituted or unsubstituted phenyl or pyridyl, and most preferably phenyl or pyridin-3-yl.

In Formula (I), it is necessary that "n" to be an integer from 0 to 5, it is preferable that "n" be an integer from 0 to 3, and it is more preferable that "n" is the integer from 1.

In Formula (I), it is necessary for $R^2$ to represent halogen, cyano, nitro, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted aryl, substituted or unsubstituted arylalkyl, substituted or unsubstituted arylalkenyl, substituted or unsubstituted heteroaryl, substituted or unsubstituted heteroarylalkyl, substituted or unsubstituted alkoxy, substituted or unsubstituted cycloalkoxy, substituted or unsubstituted heterocycloalkoxy, substituted or unsubstituted aryloxy, substituted or unsubstituted arylalkyloxy, substituted or unsubstituted arylalkenyloxy, substituted or unsubstituted heteroaryloxy, substituted or unsubstituted heteroarylalkyloxy, substituted or unsubstituted acyl, or —$NR^{N1}R^{N2}$, provided that, when n is 2 or more, a plurality of $R^2$s may be the same or different. $R^2$ preferably represents halogen (fluorine, chlorine, bromine, or iodine), cyano, nitro, substituted or unsubstituted $C_1$ to $C_5$ alkyl, substituted or unsubstituted $C_2$ to $C_5$ alkenyl, substituted or unsubstituted $C_2$ to $C_5$ alkynyl, substituted or unsubstituted $C_3$ to $C_6$ cycloalkyl, substituted or unsubstituted $C_3$ to $C_6$ cycloalkenyl, substituted or unsubstituted $C_3$ to $C_6$ cycloalkynyl, substituted or unsubstituted 3- to 6-membered heterocycloalkyl, substituted or unsubstituted $C_6$ to $C_{15}$ aryl, substituted or unsubstituted $C_7$ to $C_{16}$ arylalkyl, substituted or unsubstituted $C_8$ to $C_{17}$ arylalkenyl, substituted or unsubstituted 5- to 15-membered heteroaryl, substituted or unsubstituted 5- to 15-membered heteroarylalkyl, substituted or unsubstituted $C_1$ to $C_5$ alkoxy, substituted or unsubstituted $C_3$ to $C_6$ cycloalkoxy, substituted or unsubstituted 3- to 6-membered heterocycloalkoxy, substituted or unsubstituted $C_6$ to $C_{15}$ aryloxy, substituted or unsubstituted $C_7$ to $C_{16}$ arylalkyloxy, substituted or unsubstituted $C_8$ to $C_{17}$ arylalkenyloxy, substituted or unsubstituted 5- to 15-membered heteroaryloxy, substituted or unsubstituted 5- to 15-membered heteroarylalkyloxy, substituted or unsubstituted acyl, or —$NR^NR^{N2}$, more preferably halogen, cyano, nitro, substituted or unsubstituted alkyl, substituted or unsubstituted alkenyl, or substituted or unsubstituted alkynyl, further preferably halogen (fluorine, chlorine, bromine, or iodine), cyano, nitro, substituted or unsubstituted $C_1$ to $C_5$ alkyl, substituted or unsubstituted $C_2$ to $C_5$ alkenyl, or substituted or unsubstituted $C_2$ to $C_5$ alkynyl, particularly preferably cyano, and most preferably 4-cyano.

In Formula (I), it is particularly preferable that n be 1 and $R^2$ represent 4-cyano. In this case, the compound represented by Formula (I) can have a particularly high degree of inhibitory activity against ACAT2.

In Formula (I), it is necessary for $R^{N1}$ and $R^{N2}$ to each independently represent a monovalent group selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted aryl, substituted or unsubstituted arylalkyl, substituted or unsubstituted arylalkenyl, substituted or unsubstituted heteroaryl, substituted or unsubstituted heteroarylalkyl, substituted or unsubstituted alkoxy, substituted or unsubstituted cycloalkoxy, substituted or unsubstituted heterocycloalkoxy, substituted or unsubstituted aryloxy, substituted or unsubstituted arylalkyloxy, substituted or unsubstituted arylalkenyloxy, substituted or unsubstituted heteroaryloxy, substituted or unsubstituted heteroarylalkyloxy, and substituted or unsubstituted acyl. It is more preferable that $R^{N1}$ and $R^{N2}$ each independently represent a monovalent group selected from the group consisting of hydrogen, substituted or unsubstituted $C_1$ to $C_5$ alkyl, substituted or unsubstituted $C_2$ to $C_5$ alkenyl, substituted or unsubstituted $C_2$ to $C_5$ alkynyl, substituted or unsubstituted $C_3$ to $C_6$ cycloalkyl, substituted or unsubstituted $C_3$ to $C_6$ cycloalkenyl, substituted or unsubstituted $C_3$ to $C_6$ cycloalkynyl, substituted or unsubstituted 3- to 6-membered heterocycloalkyl, substituted or unsubstituted $C_6$ to $C_{15}$ aryl, substituted or unsubstituted $C_7$ to $C_{16}$ arylalkyl, substituted or unsubstituted $C_8$ to $C_{17}$ arylalkenyl, substituted or unsubstituted 5- to 15-membered heteroaryl, substituted or unsubstituted 5- to 15-membered heteroarylalkyl, substituted or unsubstituted $C_3$ to $C_5$ alkoxy, substituted or unsubstituted $C_3$ to $C_6$ cycloalkoxy, substituted or unsubstituted 3- to 6-membered heterocycloalkoxy, substituted or unsubstituted $C_6$ to $C_{15}$ aryloxy, substituted or unsubstituted $C_3$ to $C_{16}$ arylalkyloxy, substituted or unsubstituted $C_8$ to $C_{17}$ arylalkenyloxy, substituted or unsubstituted 5- to 15-membered heteroaryloxy, substituted or unsubstituted 5- to 15-membered heteroarylalkyloxy, and substituted or unsubstituted acyl, and further preferably a monovalent group selected from the group consisting of hydrogen, substituted or unsubstituted $C_1$ to $C_5$ alkyl, substituted or unsubstituted $C_2$ to $C_5$ alkenyl, substituted or unsubstituted $C_2$ to $C_5$ alkynyl, substituted or unsubstituted $C_6$ to $C_{15}$ aryl, and acyl.

In Formula (I), it is necessary for $R^3$ and $R^4$ to each independently represent hydrogen, hydroxyl, substituted or unsubstituted alkylcarbonyloxy, substituted or unsubstituted arylcarbonyloxy, or substituted or unsubstituted alkoxy, or $R^3$ and $R^4$ together form —O—$CR^7R^8$—O—. It is preferable that $R^3$ and $R^4$ each independently represent hydrogen, hydroxyl, substituted or unsubstituted $C_1$ to $C_5$ alkylcarbonyloxy, substituted or unsubstituted $C_6$ to $C_{15}$ arylcarbonyloxy, or $C_1$ to $C_5$ alkoxy or $R^3$ and $R^4$ together form —O—$CR^7R^8$—O—. It is more preferable that $R^3$ and $R^4$ each independently represent hydrogen or substituted or unsubstituted $C_1$ to $C_5$ alkylcarbonyloxy or $R^3$ and $R^4$ together form —O—$CR^7R^8$—O—. It is further preferable that $R^3$ and $R^4$ each independently represent hydrogen or acetoxy or $R^3$ and $R^4$ together form —O—$CR^7R^8$—O—.

In Formula (I), it is necessary for $R^5$ to represent hydrogen, hydroxyl, substituted or unsubstituted alkylcarbonyloxy, substituted or unsubstituted arylcarbonyloxy, or substituted or unsubstituted alkoxy. $R^5$ preferably represents hydrogen, hydroxyl, substituted or unsubstituted $C_1$ to $C_5$ alkylcarbonyloxy, substituted or unsubstituted $C_6$ to $C_{15}$ arylcarbonyloxy, or $C_1$ to $C_5$ alkoxy, with hydrogen being more preferable.

In Formula (I), it is necessary for $R^6$ to represent —$C(CH_3)_2$— or —$CH_2$—.

In Formula (I), it is necessary for $R^7$ and $R^8$ to each independently represent hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted aryl, substituted or unsubstituted arylalkyl, substituted or unsubstituted arylalkenyl, substituted or unsubstituted heteroaryl, or substituted or unsubstituted heteroarylalkyl. It is preferable that $R^7$ and $R^8$ each independently represent hydrogen, substituted or unsubstituted $C_1$ to $C_5$ alkyl, substituted or unsubstituted $C_2$ to $C_5$ alkenyl, substituted or unsubstituted $C_2$ to $C_5$ alkynyl, substituted or unsubstituted $C_3$ to $C_6$ cycloalkyl, substituted or unsubstituted $C_3$ to $C_6$ cycloalkenyl, substituted or unsubstituted $C_3$ to $C_6$ cycloalkynyl, substituted or unsubstituted 3- to 6-membered heterocycloalkyl, substituted or unsubstituted $C_6$ to $C_{15}$ aryl, substituted or unsubstituted $C_7$ to $C_{16}$ arylalkyl, substituted or unsubstituted $C_8$ to $C_{17}$ arylalkenyl, substituted or unsubstituted 5- to 15-membered heteroaryl, or substituted or unsubstituted 5- to 15-membered heteroarylalkyl. It is more preferable that $R^7$ and $R^8$ each independently represent hydrogen, substituted or unsubstituted alkyl, substituted or unsubstituted alkenyl, substituted or unsubstituted alkynyl, or substituted or unsubstituted aryl. It is further preferable that $R^7$ and $R^8$ each independently represent hydrogen, substituted or unsubstituted $C_1$ to $C_5$ alkyl, substituted or unsubstituted $C_2$ to $C_5$ alkenyl, substituted or unsubstituted $C_2$ to $C_5$ alkynyl, or substituted or unsubstituted $C_6$ to $C_{15}$ aryl. It is still further preferable that $R^7$ represent hydrogen and $R^8$ represent hydrogen or substituted or unsubstituted $C_6$ to $C_{15}$ aryl. It is furthermore preferable that $R^7$ represent hydrogen and $R^8$ represent hydrogen or 2-methylphenyl. It is particularly preferable that $R^7$ represent hydrogen and $R^8$ represent 2-methylphenyl.

In Formula (I), when the aforementioned groups have been substituted, it is preferable that such substituents each independently represent a monovalent group selected from the group consisting of halogen (fluorine, chlorine, bromine, or iodine), cyano, nitro, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted amino, and substituted or unsubstituted alkoxy. It is more preferable that such substituents each independently represent a monovalent group selected from the group consisting of halogen (fluorine, chlorine, bromine, or iodine), cyano, nitro, substituted or unsubstituted $C_1$ to $C_5$ alkyl, substituted or unsubstituted $C_2$ to $C_5$ alkenyl, substituted or unsubstituted $C_2$ to $C_5$ alkynyl, substituted or unsubstituted $C_3$ to $C_6$ cycloalkyl, substituted or unsubstituted $C_3$ to $C_6$ cycloalkenyl, substituted or unsubstituted $C_3$ to $C_6$ cycloalkynyl, substituted or unsubstituted amino, and substituted or unsubstituted $C_1$ to $C_5$ alkoxy. It is further preferable that such substituents each independently represent a monovalent group selected from the group consisting of halogen (fluorine, chlorine, bromine, or iodine), cyano, nitro, unsubstituted $C_1$ to $C_5$ alkyl, unsubstituted $C_2$ to $C_5$ alkenyl, unsubstituted $C_2$ to $C_5$ alkynyl, unsubstituted $C_3$ to $C_6$ cycloalkyl, unsubstituted $C_3$ to $C_6$ cycloalkenyl, unsubstituted $C_3$ to $C_6$ cycloalkynyl, unsubstituted amino, and unsubstituted $C_1$ to $C_5$ alkoxy.

A particularly preferable compound is represented by Formula (I), wherein $R^1$ represents phenyl or pyridin-3-yl; n is 1; $R^2$ represents 4-cyano; $R^3$ and $R^4$ each independently represent hydrogen or acetoxy or together form —O—$CR^7R^8$—O—; $R^5$ represents hydrogen; $R^6$ represents —$C(CH_3)_2$— or —$CH_2$—; $R^7$ represents hydrogen; and $R^8$ represents 2-methylphenyl.

A particularly preferable compound represented by Formula (I) is selected from the group consisting of the following compounds:

(5aS,6S,8S,9aS,10R)-10-hydroxy-8-isopropyl-5a-methyl-1-oxo-3-(pyridin-3-yl)-1,5a,6,7,8,9,9a,10-octahydropyrano[4,3-b]chromen-6-yl 4-cyanobenzoate ((10R)-8) (PT005);

(5aS,6S,8S,9aS,10S)-1-hydroxy-8-isopropyl-5a-methyl-1-oxo-3-(pyridin-3-yl)-1.5a,6,7,8,9,9a,10-octahydropyrano[4,3-b]chromen-6-yl 4-cyanobenzoate ((10S)-8) (PT006);

(5aS,6S,8S,9aS,10R)-10-hydroxy-8-isopropyl-5a-methyl-1-oxo-3-phenyl-1,5a,6,7,8,9,9a,10-octahydropyrano[4,3-b]chromen-6-yl 4-cyanobenzoate (34) (PT007);

(5aS,6S,8S,9aS,10R)-10-hydroxy-8-isopropyl-5a,9,9-trimethyl-1-oxo-3-(pyridin-3-yl)-1,5a,6,7,8,9,9a,10-octahydropyrano[4,3-b]chromen-6-yl 4-cyanobenzoate (15) (PT009);

(5aS,6S,8S,9aS,10R)-10-hydroxy-5a,9,9-trimethyl-1-oxo-3-(pyridin-3-yl)-8-(2-(o-toluyl)-1,3-dioxan-5-yl)-1,5a,6,7,8,9,9a,10-octahydropyrano[4,3-b]chromen-6-yl 4-cyanobenzoate (PT017); and 2-((5aS,6S,8S,9aS,10R)-6-((4-cyanobenzoyl)oxy)-10-hydroxy-5a,9,9-trimethyl-1-oxo-3-(pyridin-3-yl)-1,5a,6,7,8,9,9a,10-octahydropyrano[4,3-b]chromen-8-yl)propane-1,3-diyl diacetate (PT022).

In the present invention, the compound represented by Formula (I) and compounds represented by Formulae (II) to (IX) described below also encompass salts thereof. Preferable examples of salts of the compound represented by Formula (I) according to the present invention include, but are not limited to, salts of inorganic acids, such as hydrochloric acid, hydrobromic acid, sulfuric acid, nitric acid, carbonic acid, and phosphoric acid, and salts of organic acid anions, such as formic acid, acetic acid, maleic acid, fumaric acid, benzoic acid, ascorbic acid, succinic acid, bismethylenesalicylic acid, methanesulfonic acid, ethanedisulfonic acid, propionic acid, tartaric acid, salicylic acid, citric acid, gluconic acid, aspartic acid, stearic acid, palmitin acid, itaconic acid, glycolic acid, p-aminobenzoic acid, glutamic acid, benzenesulfonic acid, cyclohexylsulfamic acid, methanesulfonic acid, ethanesulfonic acid, isethionic acid, p-toluenesulfonic acid, and naphthalenesulfonic acid. When the compound represented by Formula (I) is in the form of the salt, such compound can be used without substantially lowering the degree of inhibitory activity against ACAT2.

The compound represented by Formula (I) and the compounds represented by Formulae (II) to (IX) described below also encompass solvates of the compounds described above and below, as well as salts thereof. Preferable examples of solvents that are capable of forming solvates with such compounds and salts thereof include, but are not limited to, a lower alcohol. e.g. an alcohol having 1 to 6 carbon atoms, such as methanol, ethanol, or 2-propanol (isopropyl alcohol), a higher alcohol, e.g. an alcohol having 7 or more carbon atoms, such as 1-heptanol or 1-octanol, an organic solvent, such as dimethylsulfoxide (DMSO), acetic acid, ethanolamine, or ethyl acetate, and water. When the compound represented by Formula (I) or a salt thereof forms a solvate with the solvent, such compound can be used without substantially lowering the degree of inhibitory activity against ACAT2.

The compound represented by Formula (I) and the compounds represented by Formulae (II) to (IX) described below encompass protected forms of the compounds described above and below. The term "protected form" used herein refers to a form of a compound in which a protecting group has been introduced into one or a plurality of functional groups, e.g. a hydroxyl or carboxylic acid group. The term "protecting group" used herein refers to a group that is introduced into a certain functional group, so as to prevent undesirable reactions from proceeding. Such group is quantitatively removed under particular reaction conditions, and it is substantially stable, that is, inactive under other reaction conditions. Preferable examples of protecting groups capable of forming protected forms of the compounds include, but are not limited to, silyl such as t-butyldimethylsilyl (TBS), triisopropylsilyl (TIPS), and tert-butyldiphenylsilyl (TBDPS) in cases involving a protecting group for hydroxyl group, and alkyl ester such as methyl, ethyl, and isopropyl ester, and arylalkyl ester such as benzyl ester in cases involving a protecting group for carboxylic acid group. Compounds can be protected and deprotected with the aid of protecting groups under known reaction conditions. When the compound represented by Formula (I) is protected with a protecting group described above, such compound can be used without substantially lowering the degree of inhibitory activity against ACAT2.

When the compound represented by Formula (I) and the compounds represented by Formulae (II) to (IX) described below have 1 or a plurality of stereocenters (chiral centers), an individual enantiomer and a diastereomer of the compound(s) and a mixture thereof, such as a racemic compound, encompass the independent enantiomer and diastereomer of the compound or a mixture thereof.

Thus, the compound represented by Formula (I) having said features can exert a high degree of inhibitory activity on ACAT2.

<2. Method for Producing Novel Compound>

The present inventors have discovered that the compound represented by Formula (I) could be synthesized from a compound having a simple 2-cyclohexenone skeleton without the use of a naturally occurring starting material, i.e., pyripyropene A with reference to total-synthesis of pyripyropene A (Non-Patent Document 9). Accordingly, the present invention also relates to a method for producing the compound represented by Formula (I) according to the present invention.

It is necessary that the method for producing the compound represented by Formula (I) according to the present invention comprise: (a) a step of epoxidation; (b) a step of aldehyde group introduction; (c) a step of C ring introduction; (d) a step of D ring introduction; (e) a step of benzoyl group introduction; and (f) a step of reduction. In the present invention, the terms "A ring," "B ring," "C ring," and "D ring" refer to rings corresponding to A ring, B ring, C ring, and D ring of pyripyropene A in compounds represented by Formulae (I) to (IX) according to the present invention, respectively. Hereafter, the aforementioned steps are described in detail.

[2-1. Step of Epoxidation]

The method for producing the compound represented by Formula (I) according to the present invention comprises a step of epoxidation epoxidizing a compound represented by Formula (II):

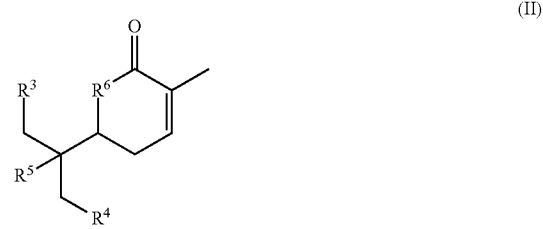

to obtain a compound represented by Formula (III).

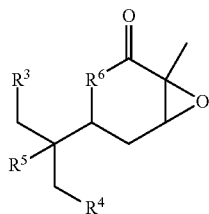
(III)

In Formulae (II) and (III), $R^3$, $R^4$, $R^5$, and $R^6$ are as defined above.

A compound represented by Formula (II) used in this step can be prepared with reference to the known method described in, for example, E. J. Sorensen et al., J. Am. Chem. Soc., Vol. 128, pp. 7025-7035, 2006 or A. Srikrishna et al., Chem. Commun., Vol. 11, pp. 1369-1370, 1996.

This step can be carried out by, for example, allowing a compound represented by Formula (II) to react with a halogenation reagent, forming a halohydrin derivative of the compound represented by Formula (II), and then allowing the halohydrin derivative to react with a base. Examples of such halogenation reagents include, but are not limited to, N-halosuccinimide, such as N-bromosuccinimide, and N-haloacetamide, such as N-bromoacetamide. Examples of such bases include, but are not limited to, diazabicycloundecene (DBU), potassium carbonate, sodium hydroxide, and potassium hydroxide. By performing this step via an epoxidation reaction, an epoxy compound represented by Formula (III) can be obtained.

[2-2. Step of Aldehyde Group Introduction]

The method for producing the compound represented by Formula (I) according to the present invention comprises a step of aldehyde group introduction introducing an aldehyde group into the compound represented by Formula (III) obtained by the step of epoxidation to obtain a compound represented by Formula (IV).

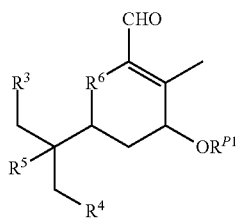
(IV)

In Formula (IV), $R^3$, $R^4$, $R^5$ and $R^6$ are as defined above.

In Formula (IV), $R^{P1}$ represents a hydroxyl protecting group. $R^{P1}$ preferably represents silyl, such as t-butyldimethylsilyl (TBS), triisopropylsilyl (TIPS), or tert-butyldiphenylsilyl (TBDPS).

This step can be performed by, for example, allowing a compound represented by Formula (III) to react with ylide and treating the resulting intermediate with an acid in the presence of water. The ylide is preferably $Ph_3PCH_2OMeCl$. The ylide can be prepared from a tetrahydrofuran solution comprising equivalent amounts of a relevant phosphonium salt and potassium t-butoxide at freezing temperature at the time of use. Examples of such acids include, but are not limited to, formic acid, acetic acid, and dilute hydrochloric acid. As a result of the reaction, a deprotected form of the compound represented by Formula (IV) can be obtained.

Alternatively, this step can be performed by, for example, allowing a compound represented by Formula (III) to react with an organosilicon-lithium compound and treating the resulting intermediate with a base. The organosilicon-lithium compound is preferably $TMSCH_2OMeLi$. The organosilicon-lithium compound can be prepared from a tetrahydrofuran solution comprising equivalent amounts of relevant alkylsilane and sec-butyl lithium at a low temperature, e.g., −50° C. to −10° C. at the time of use. The base is preferably potassium t-butoxide. As a result of the reaction, a deprotected form of the compound represented by Formula (IV) can be obtained.

In this step, subsequently, a deprotected form of the compound represented by Formula (IV) is allowed to react with a protecting reagent, so that a hydroxyl group at position 3 of the compound represented by Formula (IV) can be protected ($-OR^{P1}$). Examples of protecting reagents include, but are not limited to, t-butyldimethylsilyl chloride (TBSCl) and t-butyldimethylsilyl trifluoromethanesulfonate (TBSOTf). As a result of the reaction, a compound represented by Formula (IV) can be obtained.

[2-3. Step of C Ring Introduction]

The method for producing the compound represented by Formula (I) according to the present invention comprises a step of C ring introduction increasing the number of carbon atoms of the compound represented by Formula (IV) obtained in the step of aldehyde group introduction and subjecting it to cyclization, and obtaining a compound represented by Formula (V).

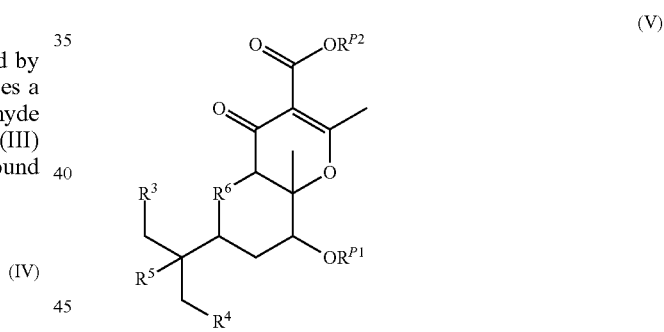
(V)

In Formula (V), $R^3$, $R^4$, $R^5$, $R^6$, and $R^{P1}$ are as defined above.

In Formula (V), $R^{P2}$ represents a carboxylic acid protecting group. $R^{P2}$ preferably represents alkyl ester such as methyl, ethyl or isopropyl ester, or arylalkyl ester such as benzyl ester.

In this step, the compound represented by Formula (IV) is allowed to react with enolate derived from acetic acid ester, and the resulting intermediate is treated with an oxidizing agent. Thus, an intermediate having the increased number of carbon atoms can be obtained. The acetic acid ester is preferably ethyl acetate or methyl acetate. The enolate derived from the acetic acid ester can be prepared from a tetrahydrofuran solution comprising the acetic acid ester and a small excess amount of lithium hexamethyldisilazide (LHMDS). The oxidizing agent is preferably 2-iodoxybenzoic acid (IBX) or Dess-Martin periodinane (DMP). Subsequently, the intermediate having the increased number of carbon atoms is allowed to react with acetyl chloride in the presence of a base such as pyridine, triethylamine or diazabicycloundecene (DBU). The resulting intermediate is then treated with a strong base to form a C ring, and a compound represented by Formula (V) can be thus obtained. The strong base is preferably diazabicycloundecene (DBU). As a result of the reaction, a compound represented by Formula (V) into which a C ring has been introduced can be obtained.

In this step, alternatively, a compound represented by Formula (IV) is allowed to react with an organic magnesium reagent, which hereafter may be referred to as a "Grignard reagent", and the resulting intermediate is oxidized to obtain an intermediate represented by Formula (IV-i).

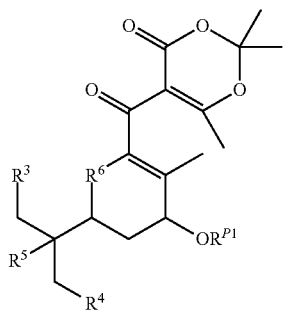

(IV-i)

In Formula (IV-i), $R^3$, $R^4$, $R^5$, $R^6$, and $R^{P1}$ are as defined above. Subsequently, the intermediate represented by Formula (IV-i) may be subjected to cyclization to obtain a compound represented by Formula (V). The organic magnesium reagent can be prepared from, for example, 5-halo-2,2,6-trimethyl-4H-1,3-dioxin-4-one and iPrMgCl at the time of use (P. Knochel et al., Tetrahedron Lett., Vol. 42, pp. 6847-6850, 2001). The oxidation reaction is aimed at conversion of an alcohol generated as a result of the reaction between the compound represented by Formula (IV) and the organic magnesium reagent into carbonyl. The oxidation reaction is preferably carried out with the use of a known oxidizing agent, such as Dess-Martin periodinane (DMP) or 2-iodoxybenzoic acid (IBX). The cyclization can be performed by, for example, allowing an intermediate represented by Formula (IV-i) to react with methanol to open the lactone ring and treating the resulting ring-opened intermediate with a strong base. The strong base is preferably diazabicycloundecene (DBU). As a result of the reaction, a compound represented by Formula (V) into which a C ring has been introduced can be obtained.

[2-4. Step of D Ring Introduction]

The method for producing the compound represented by Formula (I) according to the present invention comprises a step of D ring introduction subjecting the compound represented by Formula (V) obtained by the step of C ring introduction to cyclization, so as to obtain a compound represented by Formula (VII).

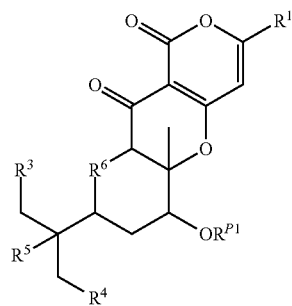

(VII)

In Formula (VII), $R^1$, $R^3$, $R^4$, $R^5$, $R^6$, and $R^{P1}$ are as defined above.

In this step, a compound represented by Formula (V) is allowed to react with a compound represented by Formula (VI):

$$R^1\text{—}COR^{L1} \qquad (VI)$$

in the presence of a base, and a compound represented by Formula (VII) can be obtained. In Formula (VI), $R^1$ is as defined above. $R^{L1}$ represents a carboxylic acid activation group. $R^{L1}$ preferably represents halogen, e.g. Cl, Br, or I, or benzotriazole. The base is preferably lithium hexamethyldisilazide (LHMDS) or lithium diisopropylamide (LDA). As a result of the reaction, a compound represented by Formula (VII) into which $R^1$ and a D ring have been introduced can be obtained.

[2-5. Step of Benzoyl Group Introduction]

The method for producing the compound represented by Formula (I) according to the present invention comprises a step of benzoyl group introduction allowing the compound represented by Formula (VII) obtained by the step of D ring introduction to react with a compound represented by Formula (VIII):

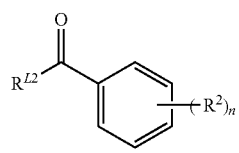

(VIII)

to obtain a compound represented by Formula (IX).

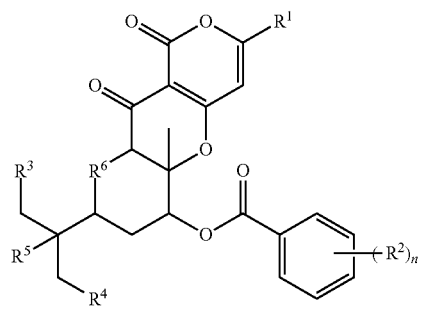

(IX)

In Formulae (VIII) and (IX), $R^1$, $R^2$, $R^3$, $R^4$, $R^5$, $R^6$, and n are as defined above. In Formula (VIII), $R^{L2}$ represents a carboxylic acid activation group. $R^{L2}$ preferably represents halogen, e.g. Cl, Br, or I. In this step, a compound represented by Formula (VIII) may be prepared in advance in the form of an activated form of a carboxylic acid having a structure represented by Formula (VIII). Alternatively, a relevant carboxylic acid may be allowed to react with a carboxylic acid condensation reagent, e.g. 1-ethyl-3-(3-dimethylaminopropyl)carbodiimide hydrochloride (EDCl) or dicyclohexylcarbodiimide (DCC)) to prepare a compound of interest in the reaction system at the time of use. As a result of the reaction, a compound represented by Formula (IX) into which a benzoyl group has been introduced can be obtained.

[2-6. Step of Reduction]

The method for producing the compound represented by Formula (I) according to the present invention comprises a step of reduction reducing a carbonyl group at position 10 of the compound represented by Formula (IX) obtained by the step of benzoyl group introduction to obtain the compound represented by Formula (I).

This step can be performed by allowing the compound represented by Formula (IX) to react with a reducing agent. The reducing agent is preferably sodium borohydride. As a result of the reaction, the compound represented by Formula (I) can be obtained.

For example, Compound 8, which is the compound represented by Formula (I) according to the present invention, wherein $R^1$ represents pyridin-3-yl, n is 1, $R^2$ represents 4-cyano, $R^3$, $R^4$, and $R^5$ each independently represent hydrogen, and $R^6$ represents —$CH_2$—, can be produced in accordance with Scheme 1 shown below.

Scheme 1

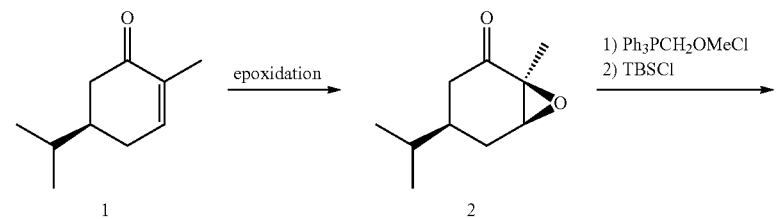

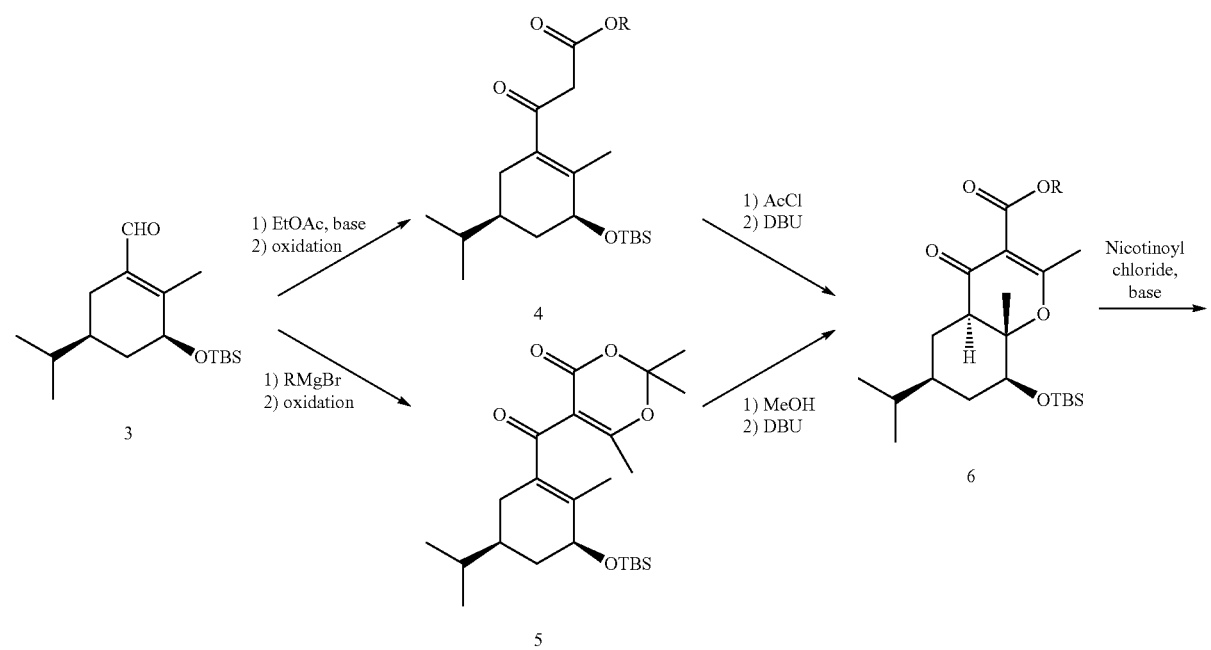

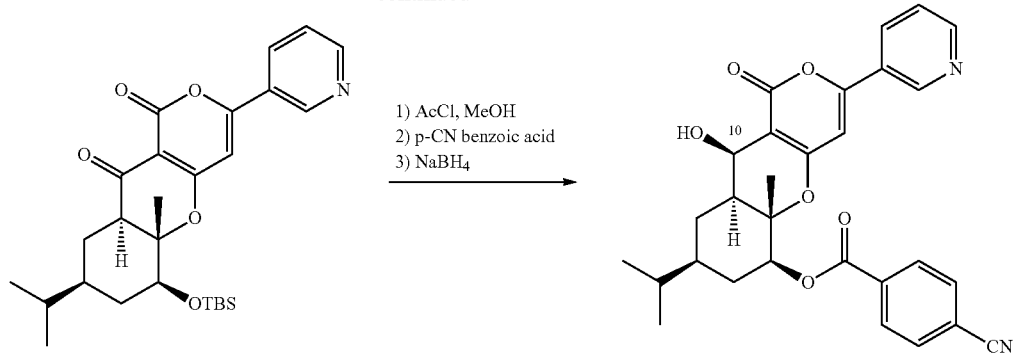

In Scheme 1, Compound 1 corresponding to the compound represented by Formula (II) as a starting compound can be prepared with reference to the known method described in, for example, E. J. Sorensen et al., J. Am. Chem. Soc., Vol. 128, pp. 7025-7035, 2006.

Compound 1 can be converted into Compound 2 by the step of epoxidation. For example, Compound 1 is subjected to reaction in the presence of 5 equivalents of a halogenation reagent, e.g. N-bromosuccinimide and 3 equivalents of 1 N perchloric acid in a hydrous dioxane solvent at freezing temperature for 4 hours, followed by general work-up. Thus, a corresponding bromohydrin derivative is obtained. The resulting bromohydrin derivative is subjected to reaction in the presence of 1 equivalent of a base, e.g. diazabicycloundecene (DBU) in a dichloromethane solvent at room temperature for 10 minutes and then subjected to general work-up. Thus, Compound 2 corresponding to the compound represented by Formula (III) can be obtained.

Compound 2 can be converted into Compound 3 by the step of aldehyde group introduction. For example, Compound 2 is subjected to reaction in the presence of 2.5 equivalents of ylide obtained by the known technique (the ylide is prepared from, for example, a tetrahydrofuran solution containing equivalent amounts of phosphonium salt and potassium t-butoxide at freezing temperature) in a tetrahydrofuran solvent at room temperature for 1.5 hours, a hydrous acid, e.g. hydrous formic acid is added thereto, and the resultant is subjected to reaction for 30 minutes, followed by general work-up. Thus, corresponding aldehyde is obtained. The resulting aldehyde is subjected to reaction in the presence of 3 equivalents of t-butyldimethylsilyl chloride (TBSCl), 6 equivalents of base, e.g. imidazole, and a catalytic amount of organic amine, e.g. dimethylaminopyridine in a dimethyl formamide solvent at 50° C. for 1 hour, followed by general work-up. Thus, Compound 3 corresponding to the compound represented by Formula (IV) can be obtained.

Compound 3 can be converted into Compound 6 by the step of C ring introduction. In this step, for example, Compound 3 can be first converted into Compound 4 or 5 and then into Compound 6.

Compound 3 can be converted into Compound 4 by the method described below. For example, Compound 3 is subjected to reaction in the presence of 1.5 equivalents of enolate derived from acetic acid ester obtained by a known method (with the enolate being prepared from, for example, a tetrahydrofuran solution comprising ethyl acetate and a small excess amount of lithium hexamethyldisilazide (LH-MDS) at −78° C.) in a tetrahydrofuran solvent at −78° C. for 5 minutes, followed by general work-up. Thus, a corresponding intermediate is obtained. The resulting intermediate is subjected to reaction in the presence of 2.5 equivalents of an oxidizing agent, e.g. 2-iodoxybenzoic acid (IBX) in a dimethylsulfoxide solvent at room temperature for 1 hour, followed by general work-up. Thus, Compound 4 corresponding to the intermediate having the increased number of carbon atoms can be obtained.

Compound 4 can be converted into Compound 6 by the method described below. For example, Compound 4 is subjected to reaction in the presence of 1.3 equivalents of magnesium chloride, 2.7 equivalents of a base, e.g. pyridine, and 1.3 equivalents of acetyl chloride in a dichloromethane solvent at −30° C. for 5 minutes, followed by general work-up. Thus, a corresponding intermediate is obtained. The resulting intermediate is subjected to reaction in the presence of 1 equivalent of a strong base, e.g. diazabicycloundecene (DBU) in a toluene solvent under reflux for 15 minutes, followed by general work-up. Thus, Compound 6 corresponding to the compound represented by Formula (V) can be obtained.

Compound 3 can be converted into Compound 5 by the method described below. For example. Compound 3 is subjected to reaction in the presence of 2 equivalents of a corresponding organic magnesium reagent obtained by a known method in a tetrahydrofuran solvent at room temperature for 15 minutes, followed by general work-up. Thus, a corresponding intermediate is obtained. The resulting intermediate is subjected to reaction in the presence of 1.5 equivalents of an oxidizing agent, e.g. Dess-Martin periodinane (DMP) in a dichloromethane solvent at 0° C. for 30 minutes, followed by general work-up. Thus, Compound 5 corresponding to the compound represented by Formula (IV-i) can be obtained.

Compound 5 can be converted into Compound 6 by the method described below. Specifically, Compound 5 is subjected to the reaction in a methanol/toluene solvent mixture at 80° C. for 5 hours, followed by general work-up. Thus, a lactone ring is opened, and a corresponding ring-opened intermediate is obtained. The resulting ring-opened intermediate is subjected to reaction in the presence of 1 equivalent of a strong base, e.g. diazabicycloundecene (DBU) in a toluene solvent at 100° C. for 12 hours, followed by general work-up. Thus, Compound 6 corresponding to the compound represented by Formula (V) can be obtained.

Compound 6 can be converted into Compound 7 by the step of D ring introduction. For example, Compound 6 is subjected to reaction in the presence of 5 equivalents of a base, e.g. lithium hexamethyldisilazide (LHMDS) in a tetrahydrofuran solvent at room temperature for 5 hours, 2 equivalents of the compound represented by Formula (VI), e.g. nicotinoyl chloride hydrochloride is added thereto, and the reaction is allowed to proceed at room temperature for 4 hours, followed by general work-up. Thus, Compound 7 corresponding to the compound represented by Formula (VII) can be obtained.

Compound 7 can be converted into Compound 8 by the step of benzoyl group introduction and the step of reduction. For example, Compound 7 is subjected to reaction in the presence of 2 equivalents of acetyl chloride in a methanol solvent at room temperature for 2 hours, followed by general work-up. Thus, a corresponding intermediate is obtained. The resulting intermediate is subjected to the reaction in a dichloromethane solvent at room temperature for 2.5 hours in the presence of 1.5 equivalents of carboxylic acid corresponding to the compound represented by Formula (VIII), e.g. p-cyanobenzoic acid, 2 equivalents of a condensation reagent, e.g. 1-ethyl-3-(3-dimethylaminopropyl)carbodiimide hydrochloride (EDCl), and a catalytic amount of dimethylaminopyridine. The compound represented by Formula (VIII) is prepared in the reaction system, and the resultant is then allowed to react with the intermediate, followed by general work-up. Thus, an intermediate corresponding to the compound represented by Formula (IX) is obtained. The resulting intermediate corresponding to the compound represented by Formula (IX) is subjected to reaction in the presence of 1.2 equivalents of a reducing agent, e.g. sodium borohydride in a methanol solvent at 0° C. for 15 minutes, followed by general work-up. Thus, a (10R) form of Compound 8 corresponding to the compound represented by Formula (I) can be obtained. This reaction is carried out with the addition of cerous chloride heptahydrate, followed by the work-up in the same manner. Thus, the (10R) form of Compound 8 corresponding to the compound represented by Formula (I) can be obtained.

For example, Compound 15, which is the compound represented by Formula (I) according to the present invention, wherein $R^1$ represents pyridin-3-yl, n is 1, $R^2$ represents 4-cyano, $R^3$, $R^4$, and $R^5$ each independently represent hydrogen, and $R^6$ represents —$C(CH_3)_2$—, can be produced in accordance with Scheme 2 shown below.

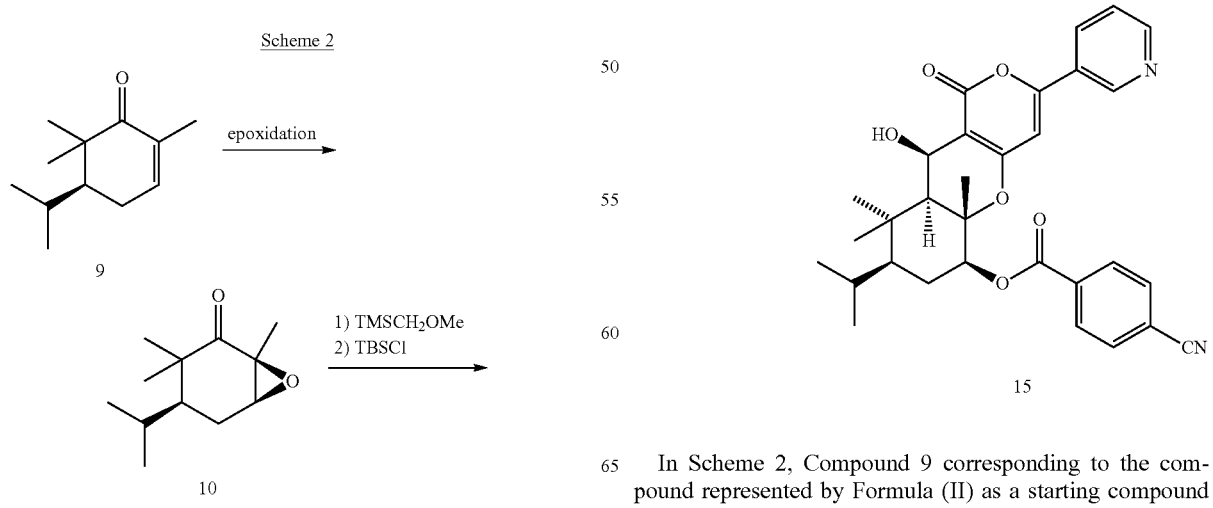

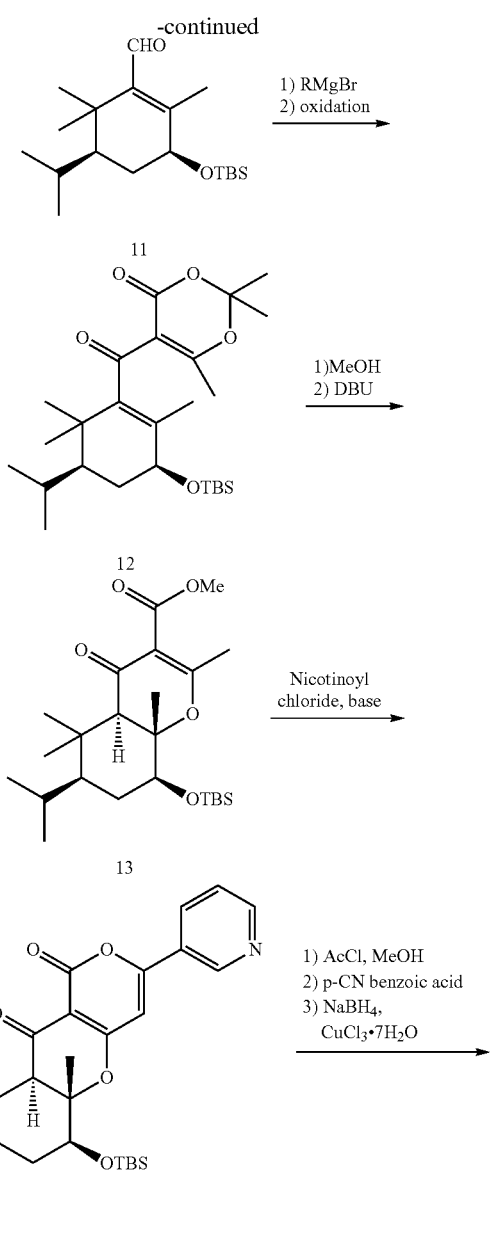

In Scheme 2, Compound 9 corresponding to the compound represented by Formula (II) as a starting compound can be prepared by, for example, introducing a methyl group into Compound 1 exemplified above with reference to the known method described in A. Srikrishna et al., Chem. Commun., Vol. 11, pp. 1369-1370, 1996.

Compound 9 can be converted into Compound 10 by the step of epoxidation. For example, Compound 9 can be converted into Compound 10 in the same manner as in the case of conversion of Compound 1 into Compound 2 shown in Scheme 1. Alternatively, Compound 9 is subjected to reaction in the presence of 3 equivalents of a halogenation reagent, e.g. N-bromoacetamide and 3 equivalents of silver acetate in an acetic acid solvent at room temperature for 4 hours, followed by general work-up. Thus, a corresponding bromohydrin intermediate is obtained. The resulting intermediate is subjected to reaction in the presence of 3 equivalents of a base, e.g. potassium carbonate in a methanol solvent at room temperature for 30 minutes, followed by general work-up. Thus, Compound 10 corresponding to the compound represented by Formula (III) can be obtained.

Compound 10 can be converted into Compound 11 by the step of aldehyde group introduction. For example, Compound 10 is subjected to reaction in the presence of 3 equivalents of an organosilicon-lithium compound obtained by a known method (such organosilicon-lithium compound is prepared from a tetrahydrofuran solution comprising equivalent amounts of relevant alkylsilane and sec-butyl-lithium at −23° C.) in a tetrahydrofuran solvent at −60° C. for 40 minutes, and the resultant is allowed to react with 4 equivalents of a base, e.g. potassium t-butoxide for 1 hour, followed by general work-up. Thus, corresponding aldehyde is obtained. The resulting aldehyde is subjected to reaction in the presence of 3 equivalents of t-butyldimethylsilyl chloride (TBSCl), 6 equivalents of a base, e.g. imidazole, and a catalytic amount of organic amine, e.g. dimethylaminopyridine in a dimethylformamide solvent at 50° C. for 1 hour, followed by general work-up. Thus, Compound 11 corresponding to the compound represented by Formula (IV) can be obtained.

Conversion of Compound 11 into Compound 12, that of Compound 12 into Compound 13, that of Compound 13 into Compound 14, and that of Compound 14 into Compound 15 can be performed in the same manner as shown in Scheme 1.

By the method described above, the compound represented by Formula (I) according to the present invention can be prepared from a compound having a simple 2-cyclohexenone skeleton without the use of a naturally occurring pyripyropene A as a starting compound. Accordingly, the present invention can provide the compound represented by Formula (I) according to the present invention that can serve as an active ingredient of a medicament or a wide variety of compounds derived from the compound according to the present invention via a synthetic means with high purity at low cost in a large quantity.

<3. Pharmaceutical Applications>

The compound represented by Formula (I) according to the present invention has a degree of inhibitory activity against ACAT2 that is equivalent to or greater than that of pyripyropene A. Accordingly, the present invention relates to an ACAT2 inhibitor comprising, as an active ingredient, the compound represented by Formula (I) according to the present invention or a salt thereof, or a solvate thereof. When the compound represented by Formula (I) according to the present invention is administered to a subject, a particular disease or symptom of the subject can be prevented or treated through the inhibitory activity against ACAT2. Accordingly, the present invention also relates to a medicament comprising, as an active ingredient, the compound represented by Formula (I) according to the present invention or a salt thereof, or a solvate thereof.

The degree of inhibitory activity of the compound represented by Formula (I) according to the present invention against ACAT2 can be determined, for example, but are not limited to, by quantitatively measuring the progress of an acyl group transfer reaction catalyzed by an enzyme source of an ACAT2 enzyme protein in the presence of the compound represented by Formula (I) according to the present invention, designating a microsome fraction prepared from the small intestine or the liver of a human or non-human mammalian animal, e.g. a warm blooded animal such as a pig, dog, cow, rat, mouse, guinea pig, rabbit, chicken, sheep, cat, monkey, sacred baboon, or chimpanzee as the enzyme source. Enzyme sources of ACAT2 enzyme proteins may be microsome fractions prepared from cultured cells expressing the human or non-human-mammalian-derived ACAT2 at high levels. Progress of the acyl group transfer reaction can be determined with the use of, for example, a radioisotope-labeled substrate (oleoyl coenzyme A).

When the compound represented by Formula (I) according to the present invention is used for pharmaceutical applications, the compound represented by Formula (I) also encompasses pharmaceutically acceptable salts thereof, and pharmaceutically acceptable solvates thereof. Preferable examples of pharmaceutically acceptable salts of the compound represented by Formula (I) according to the present invention and pharmaceutically acceptable solvates thereof include, but are not limited to, salts and solvates exemplified above. When the compound represented by Formula (I) is in the form of a salt or solvate, such compound can be used for a pharmaceutical application of interest without substantially lowering the degree of inhibitory activity against ACAT2.

When the compound represented by Formula (I) according to the present invention is used for pharmaceutical applications, such compound may be used alone or in combination with one or more pharmaceutically acceptable ingredients. The medicament according to the present invention can be formulated into a wide variety of dosage forms that are generally used in the art in accordance with an administration route of interest. Therefore, the medicament according to the present invention can be provided in the form of a pharmaceutical composition comprising the compound represented by Formula (I) according to the present invention or a salt thereof, or a solvate thereof, and one or more pharmaceutically acceptable carriers. The pharmaceutical composition according to the present invention may comprise, in addition to the components described above, one or more pharmaceutically acceptable media, e.g. a solvent such as sterile water or a solution such as physiological saline, an excipient, a binder, a vehicle, a solubilizer, a preservative, a stabilizer, a swelling agent, a lubricant, a surfactant, an emulsifier, oil water, e.g. vegetable oil, a suspending agent, a buffer, a soothing agent, an antioxidant, a sweetening agent, a flavoring agent, and the like.

The dosage form of the medicament comprising, as an active ingredient, the compound represented by Formula (I) according to the present invention or a pharmaceutically acceptable salt thereof, or a pharmaceutically acceptable solvate thereof is not particularly limited. Such medicament may be a parenteral formulation or an oral formulation. The medicament according to the present invention may be in single-unit dosage form or multiple-unit dosage form. Examples of pharmaceutical formulations used for parenteral administration include an injection preparation of an aseptic solution or a suspension comprising water or other pharmaceutically acceptable media. Examples of miscible components for injection preparations include, but are not limited to: vehicles such as isotonic solutions containing physiological saline, glucose, or another adjuvant. e.g. D-sorbitol. D-mannitol, D-mannose, or sodium chloride; solubilizers, such as alcohol, e.g. ethanol or benzyl alcohol, polyalcohol, e.g. propylene glycol or proethylene glycol, or ester, e.g. benzoic acid benzyl; nonionic surfactants, such as Polysorbate 80™ or polyoxyethylene hydrogenated castor oil; oil water, such as sesame oil or soybean oil; buffers, such as a phosphate buffer or sodium acetate buffer; soothing agents, such as benzalkonium chloride or procaine hydrochloride; stabilizers, such as human serum albumin or polyethylene glycol; preservatives; and antioxidants. Injection preparations are usually introduced into adequate vials, e.g. ampules, and stored within adequate environments before use.

Examples of oral formulations include tablets, pills, powders, capsules, microcapsules, elixirs, liquids, syrups, slurries, and suspensions. According to need, tablets may be prepared in the form of sugar-coated tablets comprising a sugar coat or soluble coat, gelatin-coated tablets, enteric-coated tablets, or film-coated tablets. Alternatively, tablets may be in the form of double-coated tablets or multiple-coated tablets.

Examples of miscible components for tablets or capsules include, but are not limited to: binders, such as water, ethanol, propanol, simple syrup, glucose liquid, carboxymethyl cellulose, shellac, methyl cellulose, potassium phosphate, polyvinyl pyrrolidone, gelatin, corn starch, gum tragacanth, and gum Arabic; excipients, such as crystalline cellulose, lactose, saccharose, sodium chloride, glucose, urea, starch, calcium carbonate, kaolin, and silicic acid; disintegrators, such as dry starch, sodium alginate, agar powder, laminaran powder, sodium bicarbonate, calcium carbonate, polyoxyethylene sorbitan fatty acid ester, sodium lauryl sulfate, stearic acid monoglyceride, starch, and lactose; disintegration inhibitors, such as saccharose, stearin cacao butter, and hydrogenated oil; absorption accelerators, such as quaternary ammonium salt and sodium lauryl sulfate; humectants, such as glycerin and starch; absorbents, such as starch, lactose, kaolin, bentonite, and colloidal silicic acid; lubricants, such as purified talc, stearate, e.g. magnesium stearate, boric acid powder, and polyethylene glycol; sweetening agents, such as sucrose, lactose, and saccharin; and flavoring agents, such as peppermint, *Gaultheria adenothrix* (Akamono) oil, and cherry. A capsule formulation may further contain an oil carrier, such as fat.

A medicament comprising, as an active ingredient, the compound represented by Formula (I) according to the present invention or a pharmaceutically acceptable salt thereof, or a pharmaceutically acceptable solvate thereof can be prepared in the form of a depot preparation. In such a case, the medicament according to the present invention in the form of a depot preparation can be administered via, for example, hypodermic or intramuscular implantation or intramuscular injection. By adopting the form of a depot formulation to the medicament according to the present invention, inhibitory activity of the compound represented by Formula (I) according to the present invention against ACAT2 can be continuously exerted for a long period of time.

A medicament comprising, as an active ingredient, the compound represented by Formula (I) according to the present invention or a pharmaceutically acceptable salt thereof, or a pharmaceutically acceptable solvate thereof can be used in combination with one or more other drugs that are useful for a medicament. Examples of other drugs that can be used in combination with the compound represented by Formula (I) according to the present invention include, but are not limited to, statin drugs, e.g. Atorvastatin. In such cases, the medicament according to the present invention is in the form of a "combined medicament" comprising the compound represented by Formula (I) according to the present invention or a pharmaceutically acceptable salt thereof, or a pharmaceutically acceptable solvate thereof in combination with one or more drugs described above. The combined medicament may be in the form of a pharmaceutical composition comprising the compound represented by Formula (I) according to the present invention or a pharmaceutically acceptable salt thereof, or a pharmaceutically acceptable solvate thereof in combination with one or more other drugs described above. Alternatively, the combined medicament may be in the form of a pharmaceutical composition comprising the compound represented by Formula (I) according to the present invention or a pharmaceutically acceptable salt thereof, or a pharmaceutically acceptable solvate thereof that is used in combination with one or more drugs described above. When the medicament according to the present invention is in the form of a combined medicament as described above, it may be provided in the form of a single formulation comprising the compound represented by Formula (I) according to the present invention or a pharmaceutically acceptable salt thereof, or a pharmaceutically acceptable solvate thereof and one or more other drugs. Alternatively, it may be provided in the form of a combination medicament or kit comprising a plurality of formulations prepared separately. In the case of a combination medicament or kit, one or more formulations can be administered simultaneously or separately, e.g. continuously.

A medicament comprising, as an active ingredient, the compound represented by Formula (I) according to the present invention or a pharmaceutically acceptable salt thereof, or a pharmaceutically acceptable solvate thereof also enables prevention or treatment of various diseases, symptoms, and/or disorders associated with ACAT2. Examples of such diseases, symptoms, and/or disorders include, but are not limited to, hyperlipemia, arteriosclerosis, hypertension, fatty liver, and obesity. Such diseases, symptoms, and/or disorders are preferably one or more diseases or symptoms selected from the group consisting of hyperlipemia, arteriosclerosis, hypertension, fatty liver, and obesity. The diseases or symptoms can be prevented or treated by administering the medicament according to the present invention to a subject in need of prevention or treatment of the diseases or symptoms.

A medicament comprising, as an active ingredient, the compound represented by Formula (I) according to the present invention or a pharmaceutically acceptable salt thereof, or a pharmaceutically acceptable solvate thereof can be administered to a wide variety of subjects in need of prevention or treatment of symptoms, diseases, and/or disorders. Such subjects are preferably human or nonhuman mammalian subjects or patients, e.g. warm blooded animals, such as pigs, dogs, cows, rats, mice, guinea pigs, rabbits, chickens, sheep, cats, monkeys, sacred baboons, or chimpanzees. Through administration of the medicament according to the present invention to the subjects, a wide variety of diseases, symptoms, and/or disorders experienced by such subjects can be prevented or treated.

The term "prevention" used herein refers to substantial inhibition of the development (crisis or onset) of symptoms, diseases, and/or disorders. The term "treatment" used herein refers to inhibition, e.g. inhibition of advancement, remission, healing, and/or cure of previously developed symptoms, diseases, and/or disorders.

The compound represented by Formula (I) according to the present invention can be used to a subject who has any of the symptoms, diseases, and/or disorders described above, e.g. hyperlipemia, arteriosclerosis, hypertension, fatty liver, or obesity in prevention or treatment thereof. Thus, the medicament according to the present invention is preferably for use in prevention or treatment of the symptoms, diseases, and/or disorders described above. It is more preferably for use in prevention or treatment of one or more diseases or symptoms selected from the group consisting of hyperlipemia, arteriosclerosis, hypertension, fatty liver, and obesity. The use of the medicament according to the present invention in prevention or treatment of the symptoms, diseases, and/or disorders associated with ACAT2 enables prevention or treatment of such symptoms, diseases, and/or disorders through the inhibitory activity of the compound represented by Formula (I) according to the present invention against ACAT2.

The compound represented by Formula (I) according to the present invention can be used to a subject who has any of the symptoms, diseases, and/or disorders described above, e.g. hyperlipemia, arteriosclerosis, hypertension, fatty liver, or obesity in prevention or treatment thereof. Accordingly, an aspect of the present invention concerns a method for prevention or treatment of the diseases or symptoms described above comprising administering an effective amount of the compound represented by Formula (I) according to the present invention or a pharmaceutically acceptable salt thereof, or a pharmaceutically acceptable solvate thereof to a subject in need of prevention or treatment of any of such symptoms, diseases, and/or disorders. The aforementioned symptoms, diseases, and/or disorders are preferably one or more diseases or symptoms selected from the group consisting of hyperlipemia, arteriosclerosis, hypertension, fatty liver, and obesity. Administration of the compound represented by Formula (I) according to the present invention to a subject in need of prevention or treatment of any of the symptoms, diseases, and/or disorders associated with ACAT2 enables prevention or treatment of such symptoms, diseases, and/or disorders.

Another aspect of the present invention concerns the compound represented by Formula (I) according to the present invention or a pharmaceutically acceptable salt thereof, or a pharmaceutically acceptable solvate thereof for use in prevention or treatment of the symptoms, diseases, and/or disorders described above. Another aspect of the present invention concerns the use of the compound represented by Formula (I) according to the present invention or a pharmaceutically acceptable salt thereof, or a pharmaceutically acceptable solvate thereof for the manufacture of a medicament for prevention or treatment of the symptoms, diseases, and/or disorders described above. The symptoms, diseases, and/or disorders are preferably one or more diseases or symptoms selected from the group consisting of hyperlipemia, arteriosclerosis, hypertension, fatty liver, and obesity. The use of the medicament according to the present invention for prevention or treatment of the symptoms, diseases, and/or disorders associated with ACAT2 enables prevention or treatment of such symptoms, diseases, and/or disorders due to the inhibitory activity of the compound represented by Formula (I) according to the present invention against ACAT2.

When administering a medicament comprising, as an active ingredient, the compound represented by Formula (I) according to the present invention or a pharmaceutically acceptable salt thereof, or a pharmaceutically acceptable solvate thereof to a subject, in particular a human patient, a primary doctor should make a final decision concerning precise dose and dosage, e.g. the amount to be administered, the frequency of administration, and/or the route of administration by considering a therapeutically effective dose, the frequency of administration, the route of administration, and other conditions on the basis of many factors, such as the age and sexuality of the subject, accurate conditions, e.g. severity of symptoms, diseases, and/or disorders to be prevented or treated, and the route of administration. Accordingly, the compound represented by Formula (I), which is an active ingredient of the medicament according to the present invention, is administered to a subject in a therapeutically effective amount and frequency. When administering the medicament according to the present invention to a human patient, for example, a dose of the compound represented by Formula (I) as an active ingredient is generally 0.001 to 100 mg/kg (body weight), typically 0.01 to 10 mg/kg (body weight), and specifically 0.1 to 10 mg/kg (body weight). The medicament according to the present invention can be administered once or a plurality of separate times per day or once every several days, for example. The medicament according to the present invention can be administered via any route without particular limitation. The medicament may be administered orally or parenterally, e.g. intrarectal, transmucosal, intestinal, intramuscular, hypodermic, intramedullary, intrathecal, direct intraventricular, intravascular, intravitreous, intraperitoneal, intranasal, or intraocular administration may be employed, in a single instance or a plurality of separate instances. The use of the medicament according to the present invention in the dose and the dosage described above enables prevention or treatment of the symptoms, diseases, and/or disorders associated with ACAT2 due to the inhibitory activity of the compound represented by Formula (I) according to the present invention against ACAT2.

EXAMPLES

Hereafter, the present invention is described in greater detail with reference to the examples, although the technical scope of the present invention is not limited to these examples.

1. Preparation of Novel Compound

Example 1

Production of (5aS,6S,8S,9aS,10R)-10-hydroxy-8-isopropyl-5a-methyl-1-oxo-3-(pyridin-3-yl)-1,5a,6,7,8,9,9a,10-octahydropyrano[4,3-b]chromen-6-yl acetate (10R)-29 (PT001)

1) Synthesis of (1 S,4R,6S)-4-isopropyl-1-methyl-7-oxabicyclo[4.1.0]heptan-2-one (2)

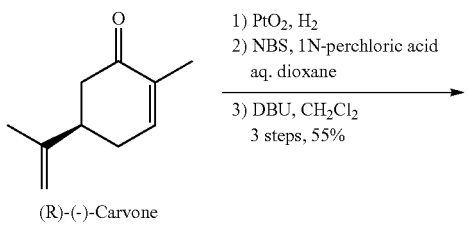

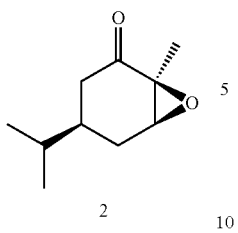

PtO$_2$ (6.0 mg, 26.3 μmol) was added to (R)-(−)-carvone (4.13 ml, 26.3 mmol), and the mixture was vigorously agitated under a hydrogen atmosphere for 14 hours. Thereafter, the resultant was filtered through Celite and the filtrate was concentrated under a reduced pressure.

To a hydrous dioxane solution (10%, 220 ml) of a crude product of Compound (1), NBS (23.4 g, 132 mmol) and 1 N perchloric acid (78.9 ml, 78.9 mmol) were added, and the mixture was agitated at 0° C. for 4 hours. The reaction was terminated with the addition of a saturated sodium thiosulfate aqueous solution and a saturated sodium bicarbonate aqueous solution, and the reaction solution was subjected to extraction with EtOAc. The combined organic phases were dried over Na$_2$SO$_4$ and then concentrated under a reduced pressure. The resulting crude product was dissolved in CH$_2$Cl$_2$ (88 ml), DBU (3.90 ml, 26.3 mmol) was added thereto, and the mixture was agitated at room temperature for 10 minutes. The reaction solution was diluted with EtOAc, and the organic phase was washed three times with water. The resulting organic phase was dried over Na$_2$SO$_4$ and then concentrated under a reduced pressure. The resulting crude product was purified via column chromatography (silica gel:200 g; hexane:EtOAc=80:1), and Compound (2) was obtained as a colorless oil product (2.44 g, 3-step process, 55%).

$^1$H-NMR (400 MHz, CDCl$_3$) δ 3.43 (d, 1H, J=4.8 Hz, CH$_2$C[H](O)), 2.56 (t, 1H, J=13.2 Hz, ½COC[H$_2$]), 2.11-2.03 (m, 2H, ½COC[H$_2$], ½C[H$_2$]CH(O)), 1.89-1.81 (m, 2H, ½C[H$_2$]CH(O), (CH$_3$)$_2$CHC[H]), 1.55-1.48 (m, 1H, (CH$_3$)$_2$C[H]CH), 1.39 (s, 3H, Me), 0.90 (d, 3H, J=6.8 Hz, (C[H$_3$])$_2$CHCH), 0.87 (d, 3H, J=6.8 Hz, (C[H$_3$])$_2$CHCH);

HRMS (EI) [M]$^+$ calcd for C$_{10}$H$_{16}$O$_2$: 168.1150; found: 168.1148.

In this description, "[H]" in the NMR assignment data indicates an atom corresponding to a chemical shift shown in such assignment data.

2) Synthesis of (3S,5S)-3-hydroxy-5-isopropyl-2-methylcyclohex-1-ene carbaldehyde (27)

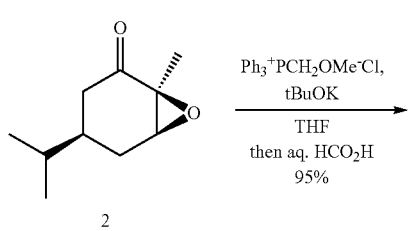

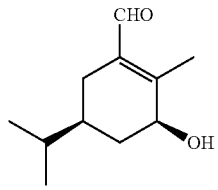

Under a nitrogen atmosphere, tBuOK (799 mg, 7.12 mmol) was added to 5.0 ml of a solution of MeOCH$_2$PPh$_3$Cl (2.44 g, 7.12 mmol) in THF, the mixture was agitated at 0° C. for 1 hour, a solution of Compound (2) (479 mg, 2.85 mmol) in THF (5.0 ml) was added dropwise thereto, the mixture was agitated at room temperature for 1.5 hours, H$_2$O (0.500 ml) and HCOOH (1.32 ml) were further added thereto, and the resultant was agitated at room temperature for 30 minutes. The reaction was terminated with the addition of a saturated K$_2$CO$_3$ aqueous solution, and the reaction product was subjected to extraction with CH$_2$Cl$_2$. The combined organic phases were dried over Na$_2$SO$_4$ and then concentrated. The resulting crude product was purified via column chromatography (silica gel; 200 g; hexane:EtOAc=3:1), and a colorless oil product (27) was obtained (493 mg, 95%).

[α]$^{27}_D$+960.1 (c, 0.1, CHCl$_3$);

IR (KBr) 3020, 2401, 1665, 1423, 1216, 756, 670, 472, 445, 405 cm$^{-1}$;

$^1$H-NMR (400 MHz, CDCl$_3$) δ 10.13 (s, 1H, C[H]O), 4.29-4.24 (m, 1H, C(CH$_3$)C[H](OH)CH$_2$), 2.39 (d, 1H, J=16.6 Hz, ½C[H$_2$]CCHO), 2.22-2.21 (m, 3H, C[H$_3$]CCH(OH)), 2.18-2.12 (m, 1H, ½C[H$_2$]CH(OH), 1.76-1.67 (m, 1H, ½C[H$_2$]CCHO), 1.58-1.50 (m, 1H, (CH$_3$)$_2$C[H]CH), 1.40-1.30 (m, 1H, (CH$_3$)$_2$CHC[H]), 1.25-1.16 (m, 1H, ½C[H$_2$]CH(OH)), 0.89 (d, 6H, J=6.8 Hz, (C[H$_3$])$_2$CHCH);

$^{13}$C-NMR (100 MHz, CDCl$_3$) δ 192.6, 156.3, 134.5, 72.9, 38.3, 36.5, 32.5, 26.7, 19.9, 19.6, 13.2;

HRMS (EI) [M]$^+$ calcd for C$_{11}$H$_{18}$O$_2$: 182.1307; found: 182.1311.

3) Synthesis of (3S,5S)-3-(tert-butyldimethylsilyloxy)-5-isopropyl-2-methylcyclohex-1-ene carbaldehyde (3)

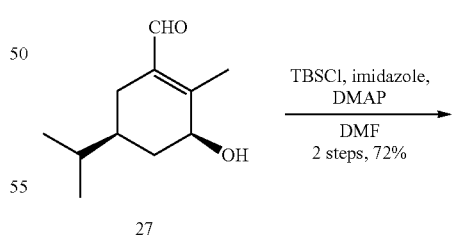

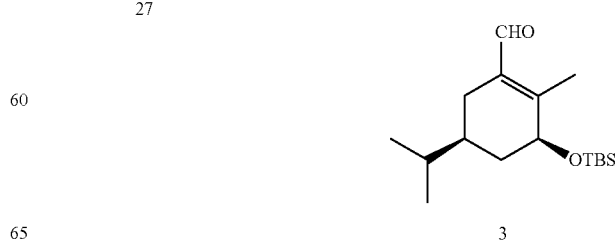

Under a nitrogen atmosphere, imidazole (1.03 g, 15.1 mmol), DMAP (N,N-dimethyl-4-aminopyridine) (37.8 mg, 0.252 mmol), and TBSCl (1.14 g, 7.57 mmol) were added to 25 ml of a solution of Compound (27) (460 mg, 2.54 mmol) in DMF, and the mixture was agitated at 50° C. for 1 hour. The reaction was terminated with the addition of a $H_2O$. EtOAc was added, and the organic phase was washed with 2N HCl and water. The organic phase was dried over $Na_2SO_4$ and then concentrated. The resulting crude product was purified via column chromatography (silica gel: 20 g; hexane:EtOAc=40:1), and Compound (3) was obtained as a colorless oil product (679 mg, 76%).

$[\alpha]^{27}_D$+53.5 (c, 1.0, $CHCl_3$);

IR (KBr) 3054, 2959, 2934, 1710, 1680, 1423, 1265, 839, 732, 707 cm$^{-1}$;

$^1$H-NMR (400 MHz, $CDCl_3$) δ 10.15 (s, 1H, C[H]O), 4.27 (br s, 1H, $CH_2$C[H](OTBS)), 2.41-2.35 (m, 1H, ½C[$H_2$]CCHO), 2.14 (s, 3H, C=C(C[$H_3$])$_2$), 2.04-1.96 (m, 1H, ½C[$H_2$]CH(OTBS), 1.78-1.68 (m, 1H, ½C[$H_2$]CCHO), 1.61-1.49 (m, 1H, $(CH_3)_2$C[H]CH), 1.33-1.24 (m, 1H, $(CH_3)_2$CHC[H]), 1.26 (dd, 1H, J=11.2, 10.0 Hz, ½C[$H_2$]CH(OTBS)), 0.92 (s, 9H, $Si(CH_3)_2C(C[H_3])_3$) 0.90 (dd, 6H, J=6.6, 1.8 Hz, $(C[H_3])_2$CHCH), 0.12 (d, 6H, J=4.2 Hz, $Si(C[H_3])_2C(CH_3)_3$);

$^{13}$C-NMR (100 MHz, $CDCl_3$) δ 192.5, 157.2, 134.3, 73.7, 38.2, 36.7, 32.5, 26.4, 26.1, 20.0, 19.5, 18.4, 13.7, −3.6, −4.6;

HRMS (FAB, PEG400) [M+Na]$^+$ calcd for $C_{17}H_{32}NaO_2Si$: 319.2069; found: 319.2064.

4) Synthesis of ethyl 3-((3S,5S)-3-(tert-butyldimethylsilyloxy)-5-isopropyl-2-methylcyclohex-1-enyl)-3-oxopropanoate (4a)

was subjected to extraction with $CH_2C_2$. The combined organic phase was dried over $Na_2SO_4$ and then concentrated.

IBX (1.37 g, 4.90 mmol) was added to a 20 ml of a solution of the residue obtained above in DMSO, and the mixture was agitated at room temperature for 1 hour. The reaction was terminated with the addition of a saturated $Na_2S_2O_3$ aqueous solution, EtOAc was added thereto, and the reaction product was washed with water. The combined organic phases were dried over $Na_2SO_4$ and then concentrated. The resulting crude product was purified via column chromatography (silica gel: 12.9 g; hexane:EtOAc=80:1), and Compound (4a) was obtained as a colorless oil product (622 mg, 2-step process, 83%).

$[\alpha]^{27}_D$+134.9 (c, 1.0, $CHCl_3$);

IR (KBr) 3054, 2958, 2933, 2859, 1736, 1617, 1417, 1265, 1218, 1079, 1041, 836, 741 cm$^{-1}$;

$^1$H-NMR (400 MHz, $CDCl_3$) δ 4.23-4.14 (m, 3H, $CH_2$C[H](OTBS), $CO_2$C[$H_2$]$CH_3$), 3.57 (s, 2H, J=3.6 Hz, $COC[H_2]CO_2$Et), 2.21-2.15 (m, 1H, ½C[$H_2$]CCOCH$_2$CO$_2$Et), 2.02-1.85 (m, 2H, ½C[$H_2$]CH(OTBS), ½C[$H_2$]COCH$_2$CO$_2$Et), 1.82 (s, 3H, C=C(C[$H_3$])), 1.59-1.48 (m, 1H, $(CH)_2$C[H]CH), 1.47-1.41 (m, 1H, $(CH_3)_2$CHC[H]), 1.27 (t, 3H, J=7.2 Hz, $CO_2CH_2C[H_3]$), 1.27-1.21 (m, 1H, ½C[$H_2$]CH(OTBS)), 0.95-0.85 (m, 15H, $Si(CH_3)_2C(C[H_3])_3$, $(C[H_3])_2$CHCH), 0.10 (s, 3H, $Si(C[H_3])_2C(CH_3)_3$), 0.08 (s, 3H, $Si(C[H_3])_2C(CH_3)_3$);

$^{13}$C-NMR (100 MHz, $CDCl_3$) δ 175.7, 168.0, 139.6, 129.1, 91.3, 73.1, 61.6, 49.1, 39.0, 36.6, 32.4, 31.6, 30.6, 26.2, 19.5, 18.5, 17.2, 16.7, 14.6, −3.7, −4.5;

HRMS (ESI, TFANa) [M+Na]$^+$ calcd for $C_{21}H_{38}NaO_4Si$: 405.2437; found: 405.2434.

5) Synthesis of 8-((tert-butyldimethylsilyl)oxy)-6-isopropyl-2,8a-dimethyl-4-oxo-4a,5,6,7,8,8a-hexahedron-4H-chromene-3-carboxylic acid.(4aR,6S,8S,8aS)-ethyl (6a)

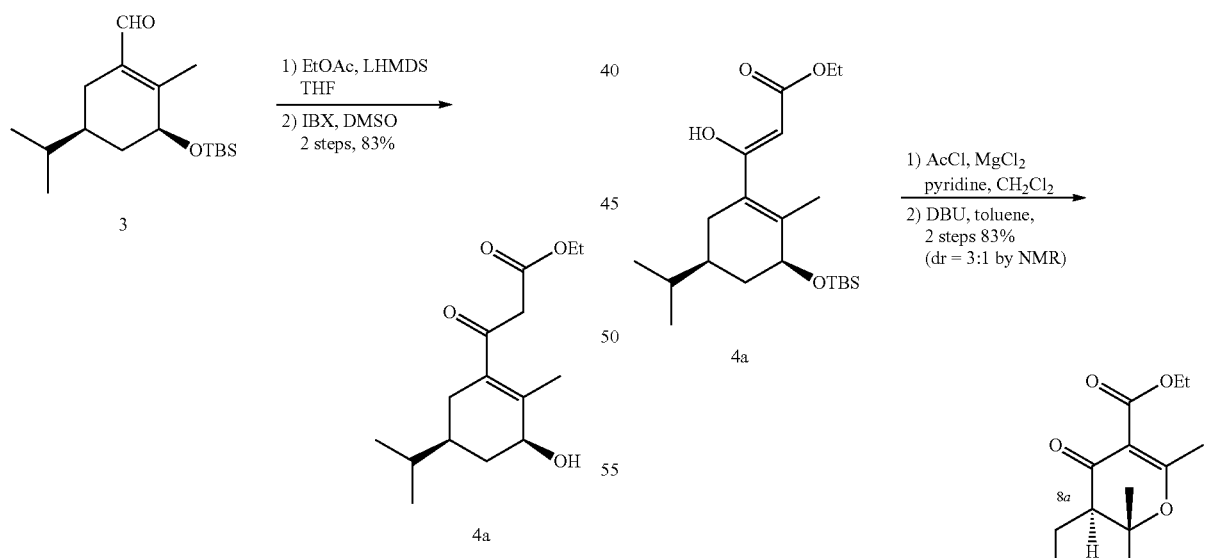

Under an argon atmosphere at −78° C., LHMDS (a 1.06 M THF solution, 2.96 ml, 3.14 mmol) was added dropwise to 10 ml of a solution of ethyl acetate (300 μl, 2.93 mmol) in THF, the mixture was agitated for 30 minutes, a solution of Compound (3) (580 mg, 1.96 mmol) in THF (10 ml) was added dropwise thereto, and the mixture was agitated for 5 minutes. The reaction was terminated with the addition of a saturated $NH_4Cl$ aqueous solution, and the reaction product Under a nitrogen atmosphere, $MgCl_2$ (22.6 mg, 240 μmol) and pyridine (38 μl, 480 μmol) were added to 2.0 ml of a solution of Compound 4a (69.9 mg, 180 μmol) in $CH_2Cl_2$, the mixture was agitated at 0° C. for 10 minutes, acetyl chloride (17 ILL, 240 µmol) was added thereto, and the mixture was agitated at room temperature for 5 minutes. The reaction was terminated with the addition of 1120, and the reaction product was subjected to extraction with $CHF_2Cl_2$. The combined organic phases were dried over $Na_2SO_4$ and then concentrated.

Under a nitrogen atmosphere, DBU (22 µl, 150 µmol) was added to 2.0 ml of a solution of the residue obtained above in toluene, and the mixture was agitated under reflux for 15 minutes. The reaction was terminated with the addition of $H_2O$, EtOAc was added thereto, and the reaction product was washed with water. The organic phase was dried over $Na_2SO_4$ and then concentrated. The resulting crude product was purified via column chromatography (silica gel: 1.02 g; hexane:EtOAc=60:1), and a yellow oil product 6a was obtained as a 3:1 diastereomer mixture at position 8a (64.5 mg, 2-step process, 83%).

$[\alpha]^{27}_D$+27.1 (c, 1.0, $CHCl_3$);

IR (KBr) 3055, 2983, 2958, 2934, 1725, 1681, 1393, 1265, 1112, 835, 733, and 706 $cm^{-1}$;

$^1$H-NMR (400 MHz, $CDCl_3$) δ 4.23 (q, 2H, J=4.4 Hz, $CO_2C[H_2]CH_3$), 3.83 (dd, 1H, J=11.2, 5.2 Hz, C[H]OTBS), 2.44 (dd, 1H, J=12.4, 4.0 Hz, $CH_2C[H]CO$), 2.17 (s, 3H, C=CC[$H_3$]), 2.07 (ddd, 1H, J=17.6, 9.2, 3.2 Hz, ½COCHC[$H_2$]), 1.74-1.66 (m, 1H, ½C[$H_2$]CH(OTBS)), 1.52-1.44 (m, 1H, $(CH_3)_2$C[H]CH), 1.43-1.38 (m, 1H, $(CH_3)_2$CHC[H]), 1.28 (t, 3H, J=7.2 Hz, $CO_2CH_2C[H_3]$), 1.16 (s, 3H, C(C[$H_3$])CH(OTBS)), 1.13 (dd, 1H, J=12.4, 1.6 Hz, ½C[$H_2$]CH(OTBS)), 0.91 (dd, 1H, J=14.0, 1.6 Hz, ½C[$H_2$]CHCO), 0.90 (s, 9H, $Si(CH_3)_2C(C[H_3])_3$), 0.87 (d, 6H, J=3.6 Hz, $(C[H_3])_2$CHCH), 0.09 (s, 3H, ½ $Si(C[H_3])_2C(CH_3)_3$), 0.07 (s, 3H, ½ $Si(C[H_3])_2C(CH_3)_3$);

$^{13}$C-NMR (100 MHz, $CDCl_3$) δ 189.7, 174.9, 165.9, 110.9, 87.2, 76.2, 60.9, 49.9, 40.5, 36.0, 32.2, 25.9, 24.0, 20.8, 20.1, 19.7, 18.3, 14.4, 10.2, −4.4;

HRMS (ESI, TFANa) [M+Na]$^+$ calcd for $C_{23}H_{40}NaO_5Si$: 447.2543; found: 447.2533.

6) Synthesis of 5-((3S,5S)-3-((tert-butyldimethylsilyl)oxy)-5-isopropyl-2-methyl-cyclohex-1-enecarbonyl)-2,2,6-trimethyl-4H-1,3-dioxin-4-one (5)

Under an argon atmosphere at −30° C., iPrMgCl (a 2.0M THF solution, 1.71 ml, 3.41 mmol) was added dropwise to 13 ml of a solution of 5-iodo-2,2,6-trimethyl-4H-1,3-dioxin-4-one (Tetrahedron Lett., 2001, Vol. 42, pp. 6847-6850) (914 mg, 3.41 mmol) in THF, the mixture was agitated for 5 minutes, 4.0 ml of a solution of Compound (3) (505 mg, 1.71 mmol) in THF was added dropwise thereto, and the mixture was agitated at −30° C. for 15 minutes. The reaction was terminated with the addition of a saturated $NH_4Cl$ aqueous solution, and the reaction product was subjected to extraction with $CH_2Cl_2$. The combined organic phases were dried over $Na_2SO_4$ and then concentrated.

Under a nitrogen atmosphere at 0° C., DMP (1.08 g, 2.56 mmol) was added to 10 ml of a solution of the residue obtained above in $CH_2Cl_2$, and the mixture was agitated for 30 minutes. The reaction was terminated with the addition of a saturated $Na_2S_2O_3$ aqueous solution and a saturated $NaHCO_3$ aqueous solution, EtOAc was added thereto, and an organic phase was washed with a saturated $NaHCO_3$ aqueous solution and water. The organic phase was dried over $Na_2SO_4$ and then concentrated. The resulting crude product was purified via column chromatography (silica gel: 50 g; hexane:EtOAc=20:1), and Compound (5) was obtained as a colorless oil product (508 mg, 2-step process, 68%).

$^1$H-NMR (400 MHz, $CDCl_3$) δ 4.21 (bs, 1H, $CH_2C[H]OSi$), 2.27 (s, 3H, $C[H_3]COC(CH_3)_2$), 2.15-2.08 (m, 1H, ½CHC[$H_2$]CHOSi), 1.96-1.90 (m, 2H, ½CHC[$H_2$]COSi, ½CHC[$H_2$]C=CCH$_3$), 1.70 (bs, 9H, C[$H_3$]CCHOSi, C(O)OC(C[$H_3$])$_2$), 1.53-1.46 (m, 2H, C[H]CH(C)$_3$)$_2$, ½CHC[$H_2$]C=CCH$_3$), 1.34-1.28 (m, 1H, CHC[H](CH$_3$)$_2$), 0.87 (bs, 15H, CHCH(C[$H_3$])$_2$, $Si(CH_3)_2C(C[H_3])_3$), 0.06 (s, 6H, $Si(C[H_3])_2C(CH_3)_3$);

$^{13}$C-NMR (100 MHz, $CDCl_3$) δ 196.8, 175.4, 158.8, 138.5, 136.1, 109.8, 106.6, 73.0, 39.1, 36.7, 32.4, 31.3, 31.1, 26.2, 25.8, 25.7, 20.2, 19.9, 19.7, 18.5, 16.5, −3.7, −4.5;

HRMS (ESI, TFANa) [M+Na]$^+$ calcd for $C_{24}H_{40}NaO_5Si$: 459.2543; found: 459.2526.

7) Synthesis of 8-((tert-butyldimethylsilyl)oxy)-6-isopropyl-2,8a-dimethyl-4-oxo-4a,5,6,7,8,8a-hexahydro-4H-chromene-3-carboxylic acid.(4aR,6S,8S,8aS)-methyl (6b)

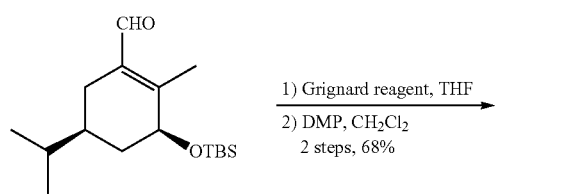

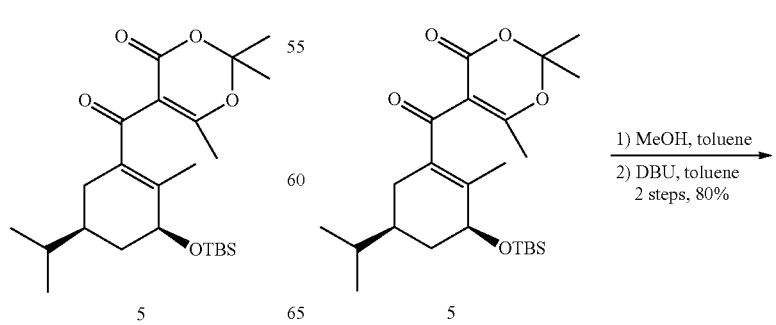

39

-continued

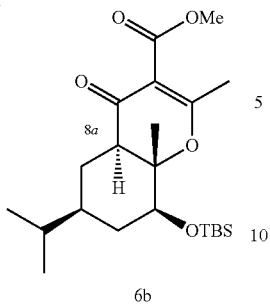

6b

Toluene (0.8 ml) and MeOH (0.2 ml) were added to Compound (5) (43.7 mg, 0.100 mmol), and the mixture was agitated at 90° C. for 12 hours, followed by concentration.

DBU (15.0 μl, 0.100 mmol) was added to 1.0 ml of a solution of the residue obtained above in toluene, and the mixture was agitated at 100° C. for 12 hours. The reaction solution was diluted with EtOAc, and the resultant was washed with H$_2$O. The organic phase was dried over Na$_2$SO$_4$ and then concentrated. The resulting crude product was purified via column chromatography (silica gel: 5 g; hexane:EtOAc=20:1), and Compound (6b) was obtained as a 4:1 diastereomer mixture at position 8a in the form of a colorless oil product (43.7 mg, 2-step process, 80%).

$^1$H-NMR (400 MHz, CDCl$_3$) δ 3.87-3.82 (m, 1H, C[H]OTBS), 3.79 (s, 3H, CO$_2$C[H$_3$]), 2.47 (dd, 1H, J=16.0, 4.0 Hz, CH$_2$C[H]CO), 2.22 (s, 3H, C=CC[H$_3$]), 2.15-2.07 (m, 1H, ½COCHC[H$_2$]), 1.77-1.71 (m, 1H, ½C[H$_2$]CH(OTBS)), 1.57-1.47 (m, 2H, (CH$_3$)$_2$C[H]CH, (CH$_3$)CHC[H])), 1.19 (s, 3H, C(C[H$_3$])CH(OTBS)), 1.30-1.25 (m, 1H, ½COCHC[H$_2$]), 1.00-0.84 (m, 16H, ½C[H$_2$]CH(OTBS), Si(CH$_3$)$_2$C(C[H$_3$])$_3$, (C[H$_3$])$_2$CHCH), 0.11 (d, 6H, J=9.2 Hz, Si(C[H$_3$])$_2$C(CH$_3$)$_3$);

$^{13}$C-NMR (100 MHz, CDCl$_3$) δ 189.4, 175.3, 166.0, 110.3, 87.5, 76.3, 69.0, 52.2, 50.1, 40.6, 36.1, 32.4, 25.4, 23.6, 20.6, 19.7, 19.4, 17.9, 9.8, −4.8, −5.3;

HRMS (ESI, TFANa) [M+Na]$^+$ calcd for C$_{22}$H$_{38}$NaO$_5$Si: 433.2386; found: 433.2403.

8) Synthesis of (5aS,6S,8S,9aR)-6-((tert-butyldimethylsilyl)oxy)-8-isopropyl-5a-methyl-3-(pyridin-3-yl)-5a,6,7,8,9,9a-hexahydropyrano[4,3-b]chromene-1,10-dione (7)

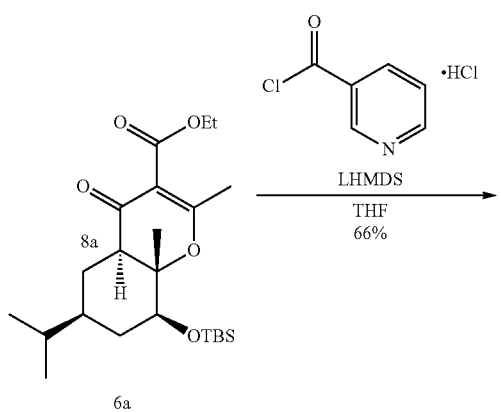

40

-continued

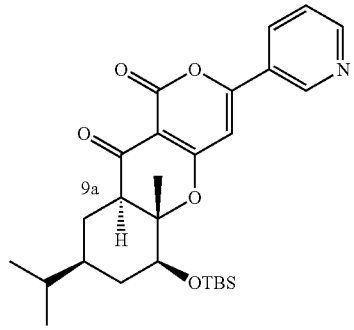

7

(dr = 3:1 from NMR)

Under an argon atmosphere at −78° C., 2.5 ml of a solution of Compound (6a) (212 mg, 500 μmol) in THF was added dropwise to LHMDS (a 1.06 M THF solution, 2.5 ml, 2.50 mmol), the mixture was agitated at room temperature for 5 hours, 2.5 ml of a solution of nicotinoyl chloride hydrochloride (178 mg, 1.00 mmol) in THF was added dropwise thereto at −78° C., and the mixture was agitated at room temperature for 4 hours. The reaction was terminated with the addition of AcOH, EtOAc was added thereto, and the resultant was washed with 2N HCl. The organic phase was dried over Na$_2$SO$_4$ and then concentrated. The resulting crude product was purified via column chromatography (silica gel: 51 g; hexane:EtOAc=5:1), and Compound (7) was obtained as a 3:1 diastereomer mixture at position 9a in the form of a yellow solid material (159 mg, 66%).

[α]$^{27}_D$+11.1 (c, 1.0, CHCl$_3$);

IR (KBr) 3055, 2982, 2307, 1758, 1429, 1265, 738 cm$^{-1}$;

$^1$H-NMR (400 MHz, CDCl$_3$) δ 9.06 (d, 1H, J=2.4 Hz, Py), 8.75 (dd, 1H, J=4.8, 1.6 Hz, Py), 8.19 (dt, 1H, J=8.0, 2.0 Hz, Py), 7.46 (ddd, 1H, J=8.0, 4.8, 2.0 Hz, Py), 6.43 (s, 1H, PyC=C[H]), 3.97 (dd, 1H, J=11.2, 5.3 Hz, C[H](OTBS)), 2.63 (dd, 1H, J=12.0, 4.0 Hz, CH$_2$C[H]CO), 2.20 (dd, 1H, J=14.0, 2.0 Hz, ½C[H$_2$]CHCO), 1.81 (dt, 1H, J=13.2, 2.4 Hz, ½C[H$_2$]CH(OTBS)), 1.56 (dd, 1H, J=12.4, 6.8 Hz, (CH$_3$)$_2$C[H]CH), 1.48-1.40 (m, 1H, (CH$_3$)$_2$CHC[H]), 1.30 (s, 3H, C(C[H$_3$])CCH(OTBS)), 1.22-1.21 (m, 1H, ½C[H$_2$]CHOSi(CH$_3$)$_2$C(CH$_3$)$_3$), 1.11-1.05 (m, 1H, ½C[H$_2$]CH(OTBS)), 0.96 (s, 9H, Si(CH$_3$)$_2$C(C[H$_3$])$_3$), 0.92 (dd, 6H, J=6.8, 2.4 Hz, (C[H$_3$])$_2$CHCH), 0.19 (s, 3H, ½ Si(C[H$_3$])$_2$C(C[H$_3$])$_3$), 0.15 (s, 3H, ½ Si(C[H$_3$])$_2$C(CH$_3$)$_3$);

$^{13}$C-NMR (100 MHz, CDCl$_3$) δ 188.0, 173.5, 162.7, 157.0, 152.8, 147.8, 134.1, 127.0, 134.1, 127.0, 124.1, 98.3, 89.9, 76.1, 51.6, 40.4, 36.0, 32.3, 30.0, 26.1, 24.3, 20.1, 19.0, 11.1, −4.1, −4.2;

HRMS (ESI, TFANa) [M+Na]$^+$ calcd for C$_{27}$H$_{37}$NNaO$_5$Si: 506.2339; found: 506.2345.

9) Synthesis of (5aS,6S,8S,9aR)-6-(acetoxy)-8-isopropyl-5a-methyl-3-(phenyl)-5a,6,7,8,9,9a-hexahydropyrano[4,3-b]chromene-1,10-dione ((9aR)-28) and (5aS,6S,8S,9aS)-6-(acetoxy)-8-isopropyl-5a-methyl-3-(phenyl)-5a,6,7,8,9,9a-hexahydropyrano[4,3-b]chromene-1,10-dione ((9aS)-28)

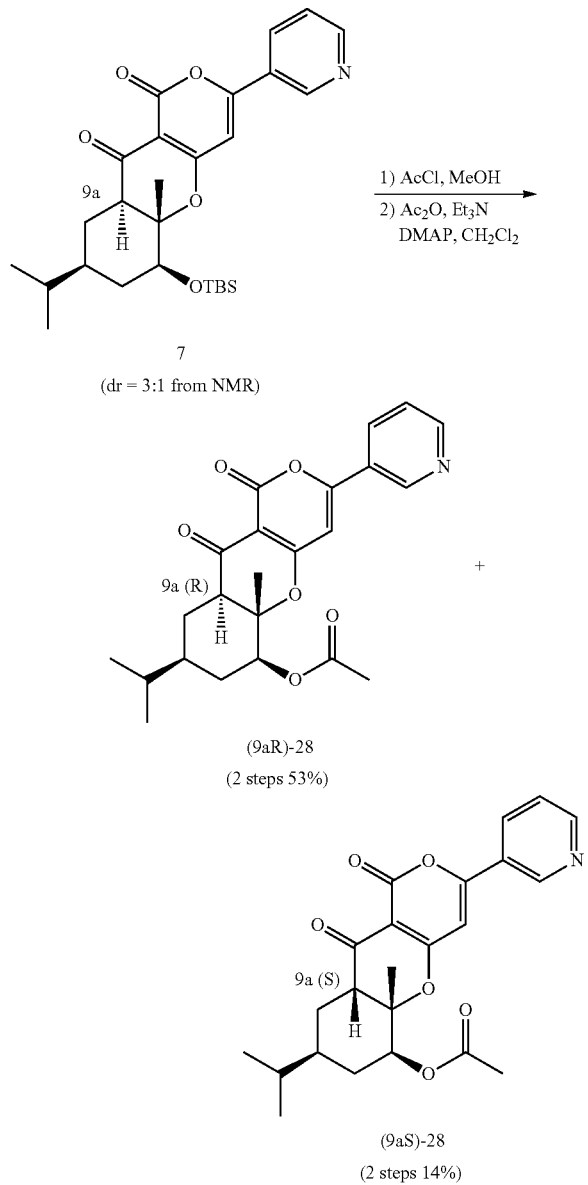

phases were dried over $Na_2SO_4$ and then concentrated. The resulting crude product was purified via preparative TLC (hexane:EtOAc=1:20), and yellow solid materials; i.e., Compound ((9aR)-28) (99.0 mg, 2-step process, 53%) and Compound ((9aS)-28) (24.5 mg, 2-step process, 14%), were obtained separately as a single diastereomer.

Identification Data for Compound ((9aR)-28)

$[\alpha]^{27}_D$+10.2 (c, 1.0, $CHCl_3$);

IR (KBr) 2930, 1757, 1628, 1536, 1431, 1262, 738 $cm^{-1}$;

$^1$H-NMR (300 MHz, $CDCl_3$) δ 9.06 (dd, 1H, J=2.1, 0.6 Hz, Py), 8.74 (dd, 1H, J=4.8, 1.5 Hz, Py), 8.18 (ddd, 1H, J=8.4, 2.4, 1.8 Hz, Py), 7.44 (dd, 1H, J=8.1, 0.6 Hz, Py), 6.54 (s, 1H, PyC=C[H]), 5.26 (dd, 1H, J=11.7, 5.1 Hz, C[H](OAc)), 2.75 (dd, 1H, J=12.3, 3.6 Hz, $CH_2$C[H]CO), 2.27 (ddd, 1H, J=14.4, 5.7, 3.9 Hz, ½C[$H_2$]CHCO), 2.19 (s, 3H, COCHC(C[$H_3$])), 2.06-1.98 (m, 1H, ½C[$H_2$]CH(OAc)), 1.64-1.53 (m, 1H, $(CH_3)_2$C[H]CH), 1.39 (s, 3H, CH(OAc)C(C[$H_3$])), 1.40-1.29 (m, 1H, $(CH_3)_2$C[H]C[H]), 1.18-1.05 (m, 1H, ½C[$H_2$]CHCO), 0.87-0.81 (m, 1H, ½C[$H_2$]CH(OAc)), 0.92 (d, 6H, J=6.3 Hz, (C[$H_3$])$_2$CHCH);

$^{13}$C-NMR (100 MHz, $CDCl_3$) δ 187.0, 173.2, 170.5, 162.9, 156.9, 153.0, 147.9, 134.1, 126.9, 124.1, 100.5, 98.5, 87.4, 76.1, 51.6, 40.4, 32.3, 32.0, 24.5, 21.6, 20.2, 20.0, 12.0;

HRMS (ESI, TFANa) [M+Na]$^+$ calcd for $C_{23}H_{25}NNaO_6$: 434.1580; found: 434.1565.

Identification Data for Compound ((9aS)-28)

$[\alpha]^{27}_D$+63.5 (c, 1.0, $CHCl_3$);

IR (KBr) 2930, 1757, 1628, 1536, 1431, 1262, 737 $cm^{-1}$;

$^1$H-NMR (300 MHz, $CDCl_3$) δ 9.08-9.06 (m, 1H, Py), 8.75-8.72 (m, 1H, Py), 8.22 (dd, 1H, J=7.2, 1.5 Hz, Py), 7.65 (dd, 1H, J=6.9, 5.1 Hz, Py), 6.41 (s, 1H, PyC=C[H]), 5.38 (dd, 1H, J=11.7, 5.1 Hz, C[H](OAc)), 2.94 (dd, 1H, J=4.2, 3.0 Hz, $CH_2$C[H]CO), 2.67 (dd, 1H, J=13.2, 2.1 Hz, ½C[$H_2$]CHCO), 2.09 (s, 3H, COCHC(C[H])), 1.91-1.85 (m, 1H, ½$CH_2$C[H]CO), 1.67 (s, 3H, CH(OAc)C(C[$H_3$])), 1.54-1.35 (m, 2H, $(CH_3)_2$C[H]CH, $(CH_3)_2$CHC[H]), 1.35-1.09 (m, 2H, ½C[$H_2$]CHCO, ½C[$H_2$]CH(OAc)), 0.90 (d, 6H, J=5.1 Hz, (C[$H_3$])$_2$CHCH);

$^{13}$C-NMR (75 MHz, $CDCl_3$) δ 186.7, 173.6, 170.3, 162.8, 157.0, 152.4, 147.5, 134.6, 129.1, 124.3, 100.2, 98.7, 88.0, 70.0, 51.6, 37.7, 33.0, 32.4, 30.0, 25.7, 21.6, 21.4, 20.7;

HRMS (ESI, TFANa) [M+Na]$^+$ calcd for $C_{23}H_{25}NNaO_6$: 434.1588; found: 434.1565.

10) Synthesis of (5aS,6S,8S,9aS,10R)-10-hydroxy-8-isopropyl-5a-methyl-1-oxo-3-(pyridin-3-yl)-1,5a,6,7,8,9,9a,10-octahydropyrano[4,3-b]chromen-6-yl acetate ((10R)-29) (PT001)

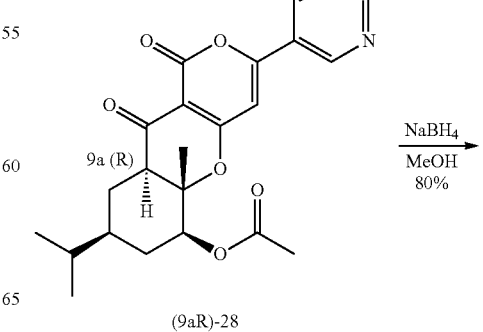

Under a nitrogen atmosphere, 4.5 ml of a solution of AcCl (65 μl, 912 μmol) in MeOH was added dropwise to 4.5 ml of a solution of Compound (7) (221 mg, 463 μmol) in MeOH, and the mixture was agitated at room temperature for 2 hours, followed by concentration.

Under a nitrogen atmosphere, DMAP (6.1 mg, 52.1 μmol), Et$_3$N (254 μl, 1.82 mmol), and Ac$_2$O (86 μl, 911 μmol) were added to 4.5 ml of a solution of the residue obtained above in $CH_2Cl_2$, and the mixture was agitated at room temperature for 30 minutes. The reaction was terminated with the addition of $H_2O$, and the reaction product was subjected to extraction with $CH_2Cl_2$. The combined organic

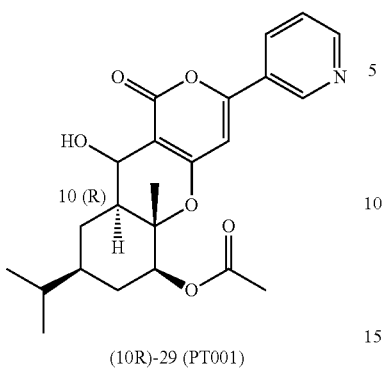

(10R)-29 (PT001)

Under a nitrogen atmosphere. NaBH$_4$ (8.1 mg, 29.5 μmol) was added to 0.2 ml of a solution of Compound ((9aR)-28) (10.1 mg, 24.6 μmol) in MeOH, and the mixture was agitated at 0° C. for 15 minutes. The reaction was terminated with the addition of acetone, EtOAc was added thereto, and the reaction product was washed with water. The combined organic phases were dried over Na$_2$SO$_4$ and then concentrated. The resulting crude product was purified via preparative TLC (hexane:EtOAc=1:20), and Compound ((10R)-29) (PT001) was obtained as a white solid material (8.0 mg, 80%).

$[\alpha]^{27}_D$ +17.8 (c, 1.0, CHCl$_3$);

IR (KBr) 3055, 2929, 2309, 1708, 1428, 1264, 897, 735 cm$^{-1}$;

$^1$H-NMR (300 MHz, CDCl$_3$) δ 9.03 (d, 1H, J=4.8 Hz, Py), 8.70 (d, 1H, J=4.5 Hz, Py), 8.15 (d, 1H, J=5.1 Hz, Py), 7.44 (dd, 1H, J=4.8, 3.0 Hz, Py), 6.50 (s, 1H, PyC=C[H]), 5.02 (dd, 1H, J=11.7, 4.8 Hz, C[H](OAc)), 4.64 (d, 1H, J=4.2 Hz, CHC[H](OH)), 2.21 (s, 3H, OCHC(C[H$_3$])), 2.01-1.95 (m, 1H, ½C[H$_2$]CH(OAc)), 1.90-1.81 (m, 2H, ½C[H$_2$]CHCH(OH), CH$_2$C[H]CH(OH)), 1.65-1.42 (m, 3H, ½C[H$_2$]CHCH(OH), (CH$_3$)$_2$C[H]CH, (CH$_3$)$_2$CHC[H]), 1.50 (s, 3H, CC(C[H$_3$])O), 1.37-1.29 (m, 1H, ½C[H$_2$]CH(OAc)) 0.95 (d, 3H, J=4.5 Hz, (C[H$_3$])$_2$CHCH), 0.93 (d, 3H, J=4.5 Hz, (C[H$_3$])$_2$CHCH);

$^{13}$C-NMR (75 MHz, CDCl$_3$) δ 170.8, 164.4, 163.4, 157.7, 151.9, 147.2, 133.4, 103.6, 99.9, 83.0, 62.0, 43.7, 41.4, 32.6, 30.1, 27.8, 23.0, 21.7, 20.2, 20.1, 14.5, 13.0;

HRMS (ESI, TFANa) [M+Na]$^+$ calcd for C$_{23}$H$_{27}$NNaO$_6$: 436.1736; found: 436.1723.

Example 2

Production of (5aS,6S,8S,9aS,10S)-10-hydroxy-8-isopropyl-5a-methyl-1-oxo-3-(pyridin-3-yl)-1,5a,6,7,8,9,9a,10-octahydropyrano[4,3-b]chromen-6-yl acetate ((10S)-29) (PT002)

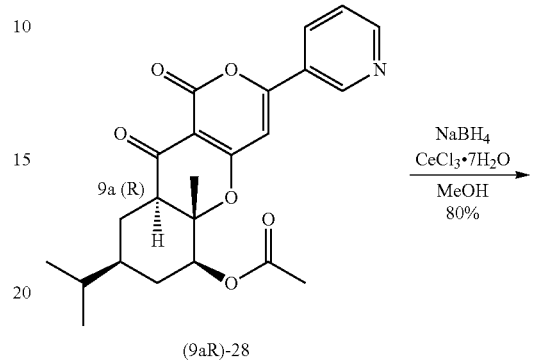

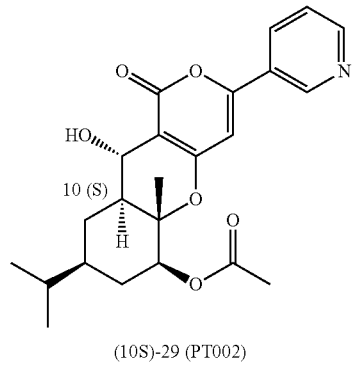

(10S)-29 (PT002)

Under a nitrogen atmosphere, CeCl$_3$.7H$_2$O (11.0 mg, 29.5 μmol) and NaBH$_4$ (1.1 mg, 29.5 μmol) were added to 0.2 ml of a solution of Compound ((9aR)-28) (10.0 m, 24.6 μmol) obtained in Example 1 in MeOH, and the mixture was agitated at 0° C. for 15 minutes. The reaction was terminated with the addition of acetone, EtOAc was added thereto, and the reaction product was washed with water. The combined organic phases were dried over Na$_2$SO$_4$ and then concentrated. The resulting crude product was purified via preparative TLC (hexane:EtOAc=1:2), and Compound ((10S)-29) (PT002) was obtained as a white solid material (7.3 mg, 74%).

$[\alpha]^{27}_D$ +27.1 (c, 1.0, CHCl$_3$);

IR (KBr) 2928, 2859, 1715, 1261, 735 cm$^{-1}$;

$^1$H-NMR (400 MHz, CDCl$_3$) δ 9.01 (d, 1H, J=2.0 Hz, Py), 8.69 (dd, 1H, J=4.8, 1.6 Hz, Py), 8.10 (ddd, 1H, J=8.0, 2.4, 1.6 Hz, Py), 7.40 (ddd, 1H, J=8.4, 5.2, 0.8 Hz, Py), 6.49 (s, 1H, PyC=C[H]), 5.06 (dd, 1H, J=12.0, 4.8 Hz, C[H](OAc)), 4.45 (d, 1H, J=10.0 Hz, CHC[H](OH)), 2.33-2.27 (m, 1H, ½C[H$_2$]CHCH(OH), 2.18 (s, 3H, C[H$_3$]CO), 2.01-1.95 (m, 1H, ½C[H$_2$]CH(OAc)), 1.86 (ddd, 1H, J=12.4, 10.0, 3.6 Hz, CH$_2$C[H]CH(OH)), 1.59-1.43 (m, 2H, (CH$_3$)$_2$C[H]CH, (CH$_3$)$_2$CHC[H]), 1.28 (s, 3H, CC(C[H$_3$])O), 1.37-1.20 (m, 1H, ½C[H$_2$]CH(OAc)), 1.02-0.87 (m, 1H, ½C[H$_2$]CHCH(OH)), 0.93 (d, 3H, J=4.8 Hz, (C[H$_3$])$_2$CHCH), 0.91 (d, 3H, J=4.8 Hz, (C[H$_3$])$_2$CHCH);

$^{13}$C-NMR (100 MHz, CDCl$_3$) δ 170.6, 164.0, 163.4, 157.6, 151.2, 146.8, 133.7, 121.0, 100.0, 83.9, 64.5, 63.6, 45.0, 40.9, 32.4, 30.0, 28.9, 23.0, 21.7, 20.2, 20.1, 14.5, 12.3;

HRMS (ESI, TFANa) [M+Na]$^+$ calcd for $C_{23}H_{27}NNaO_5$: 436.1736; found: 436.1734.

Example 3

Production of (5aS,6S,8S,9aS,10R)-10-hydroxy-8-isopropyl-5a-methyl-1-oxo-3-(pyridin-3-yl)-1,5a,6,7,8,9,9a,10-octahydropyrano[4,3-b]chromen-6-yl 4-cyanobenzoate ((10R)-8) (PT005)

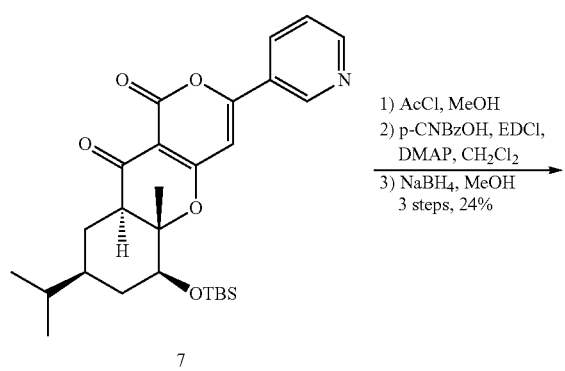

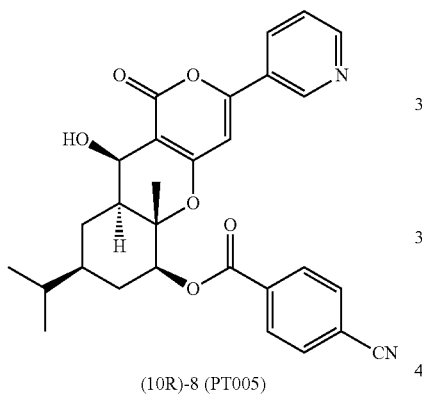

(10R)-8 (PT005)

AcCl (48 μl, 0.0681 mmol) was added to 800 μl of a solution of Compound (7) (32.9 mg, 0.0681 mmol) obtained in Example 1 in MeOH at 0° C., the mixture was agitated for 1 hour, and the reaction product was subjected to extraction with CH$_2$Cl$_2$. The combined organic phases were dried over Na$_2$SO$_4$ and then concentrated. Under a nitrogen atmosphere, EDCl (23.5 mg, 0.122 mmol), DMAP (1.0 mg, 0.0122 mmol), and p-cyanobenzoic acid (p-CNBzOH) (15.0 mg, 0.102 mmol) were added to 0.800 ml of a solution of the resulting crude product in CH$_2$Cl$_2$, and the mixture was agitated at room temperature for 2.5 hours. The reaction was terminated with the addition of water, and the reaction product was subjected to extraction with CH$_2$Cl$_2$. Thereafter, the organic phase was dried over Na$_2$SO$_4$ and then concentrated. NaBH$_4$ (3.3 mg, 0.0868 mmol) was added to 0.800 ml of a solution of the resulting crude product in MeOH at 0° C., and the mixture was agitated at 0° C. for 1 hour. The reaction was terminated with the addition of acetone, and the resultant was washed with EtOAc. The organic phase was dried over Na$_2$SO$_4$ and then concentrated. The resulting crude product was purified via preparative TLC (EtOAc), and Compound ((10R)-8) (PT005) was obtained as a white solid material (8.20 mg, 3-step process, 24%).

[α]$^{27}_D$+55.3 (c, 0.1, CHCl$_3$);
IR (KBr) 3442, 3020, 2400, 2360, 1635, 1215, 1105, 784, 753, 669, 603, 468, 445, 421, 406 cm$^{-1}$;
$^1$H-NMR (300 MHz, CDCl$_3$) δ 9.11 (s, 1H, Py), 8.76 (s, 1H, Py), 8.52 (s, 1H, Py), 8.21 (d, 2H, J=8.4 Hz, Ph), 7.80 (d, 3H, J=8.4 Hz, Ph, Py), 6.54 (s, 1H, PyC=C[H]), 5.31 (dd, 1H, J=11.1, 5.1 Hz, C[H]OC(O)PhCN), 4.69 (d, 1H, J=4.2 Hz, C[H](OH)CH), 2.12 (d, 1H, J=5.1 Hz, ½C[H$_2$]CHCH(OH)), 1.95 (m, 1H, ½CHC[H$_2$]CHOC(O)PhCN), 1.88 (s, 1H, C[H]CH(OH)), 1.72-1.54 (m, 1H, C[H](CH$_3$)$_2$), 1.51-1.49 (m, 1H, C[H]CH(Cl$_3$)$_2$), 1.31-1.22 (m, 2H, ½CHC[H$_2$]CHOC(O)PhCN, ½C[H$_2$]CHCH(OH), 1.25 (s, 9H, (C[H$_3$])$_2$CHCH, C[H$_3$]COC=C);
$^{13}$C-NMR (75 MHz, CDCl$_3$) δ 164.3, 162.1, 134.0, 132.5, 130.4, 129.4, 118.0, 116.9, 105.7, 83.6, 77.9, 77.3, 61.4, 43.5, 41.3, 32.4, 32.1, 29.8, 29.7, 29.5, 22.8, 20.0, 19.9, 14.2, 13.2;
HRMS (ESI) [M+Na]$^+$ calcd for $C_{29}H_{28}N_2NaO_6$: 523.1845; found: 523.1843.

Example 4

Production of (5aS,6S,8S,9aS,10S)-10-hydroxy-8-isopropyl-5a-methyl-1-oxo-3-(pyridin-3-yl)-1,5a,6,7,8,9,9a,10-octahydropyrano[4,3-b]chromen-6-yl 4-cyanobenzoate ((10S)-8) (PT006)

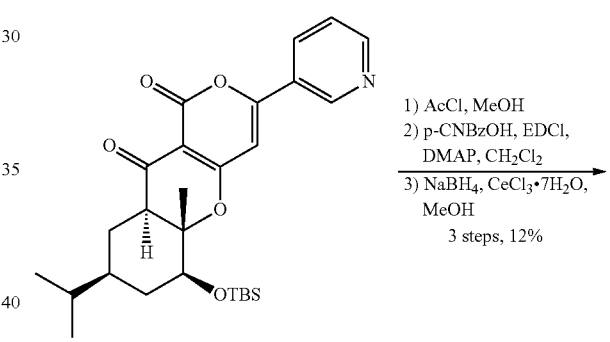

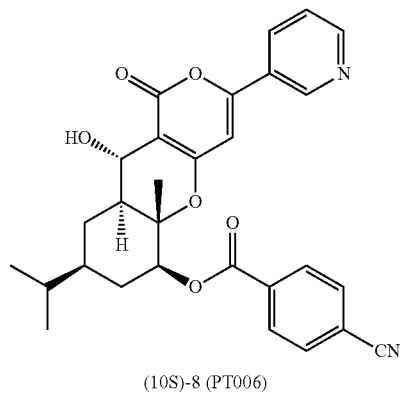

(10S)-8 (PT006)

AcCl (0.048 ml, 0.673 mmol) was added to 1.3 ml of a solution of Compound (7) (65.1 mg, 0.135 mmol) obtained in Example 1 in MeOH at 0° C., the mixture was agitated for 1 hour, and the reaction product was subjected to extraction with CH$_2$Cl$_2$. The combined organic phases were dried over Na$_2$SO$_4$ and then concentrated.

Under a nitrogen atmosphere, EDCl (46.4 mg, 0.242 mmol), DMAP (1.6 mg, 0.0135 mmol), and p-CNBzOH (29.7 mg, 0.202 mmol) were added to 1.3 ml of a solution of the resulting crude product in CH$_2$C$_2$ at room temperature, and the mixture was agitated at room temperature for 2.5 hours. The reaction was terminated with the addition of water, and the reaction product was subjected to extraction with CH$_2$C$_2$. The organic phase was dried over Na$_2$SO$_4$ and then concentrated. NaBH$_4$ (6.62 mg, 0.175 mmol) and CeCl$_3$.7H$_2$O (65.2 mg, 0.175 mmol) were added to 1.3 ml of a solution of the resulting crude product in MeOH at 0° C. and the mixture was agitated at 0° C. for 1 hour. The reaction was terminated with the addition of acetone, and the reaction product was diluted with EtOAc, followed by washing with water. The organic phase was dried over Na$_2$SO$_4$ and then concentrated. The resulting crude product was purified via preparative TLC (EtOAc), and Compound ((10R)-8) (PT006) was obtained as a white solid material (8.2 mg, 3-step process, 12%).

$^1$H-NMR (600 MHz, CDCl$_3$) δ 8.98 (bs, 1H, Py), 8.69 (bs, 1H, Py), 8.20 (d, 2H, J=8.4 Hz, Ph), 8.14 (dd, 1H, J=11.1, 8.7 Hz, Py), 7.80 (d, 2H, J=8.4 Hz, Ph), 7.46 (dd, 1H, J=8.1, 5.1 Hz, Py), 6.44 (s, 1H, C[H]=CPy), 5.35 (dd, 1H, J=12.0, 5.0 Hz, C[H]OC(O)PhCN), 4.50 (d, 1H, J=9.6 Hz, C[H](OH)CHCH$_2$), 2.37 (ddd, 1H, J=12.5, 3.5, 2.0 Hz, ½C[H$_2$]CHCH(OH)), 2.15 (ddd, 1H, J=12.0, 10.0, 3.5, ½ CHC[H$_2$]CHOC(O)PhCN), 1.67 (s, 1H, CH$_2$C[H]CH(OH)), 1.63-1.53 (m, 1H, CHC[H](CH$_3$)$_2$), 1.46-1.37 (m, 1H, C[H]CH(CH$_3$)$_2$), 1.25-1.20 (m, 2H, ½CHC[H$_2$]CHOC(O)PhCN, ½C[H$_2$]CHCH(OH), 0.96-0.94 (m, 9H, (C[H$_3$])$_2$CHCH, C[H$_3$]COC=C);

$^{13}$C-NMR (150 MHz, CDCl$_1$) δ 164.0, 163.4, 162.8, 156.9, 150.4, 145.7, 134.0, 132.3, 130.2, 127.5, 124.1, 117.8, 116.7, 103.1, 99.8, 83.6, 77.7, 63.1, 44.7, 40.6, 32.2, 29.7, 28.6, 19.8, 19.7, 12.3;

HRMS (ESI) [M+Na]$^+$ calcd for C$_2$H$_{28}$N$_2$NaO$_6$: 523.1845; found: 523.1847.

Example 5

Production of (5aS,6S,8S,9aS,10R)-10-hydroxy-8-isopropyl-5a-methyl-1-oxo-3-phenyl-1,5a,6,7,8,9,9a,10-octahydropyrano[4,3-b]chromen-6-yl acetate (10R)-33 (PT003)

1) Synthesis of (5aS,6S,8S,9aR)-6-((tert-butyldimethylsilyl)oxy)-8-isopropyl-5a-methyl-3-(phenyl)-5a,6,7,8,9,9a-hexahydropyrano[4,3-b]chromene-1,10-dione (31)

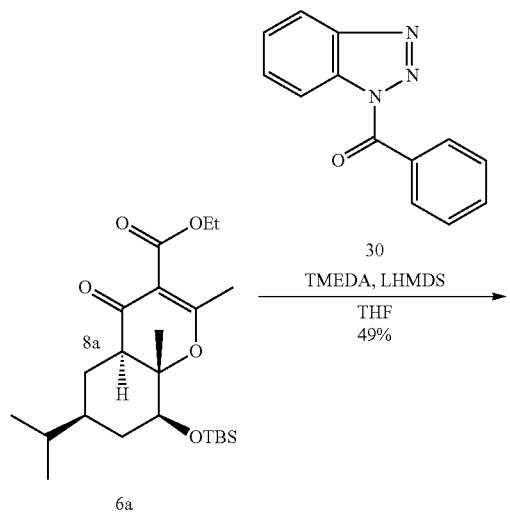

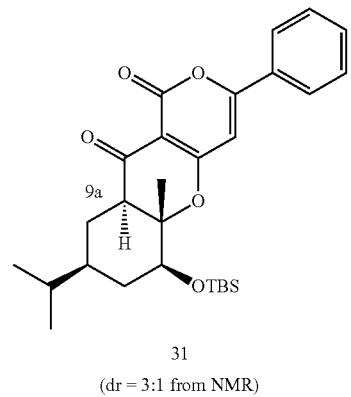

31
(dr = 3:1 from NMR)

Under an argon atmosphere at −78° C., 4.7 ml of a solution of Compound (6a) (400 mg, 940 μmol) and TMEDA (tetramethylethylenediamine) (560 μl, 3.76 mmol) in THF was added dropwise to LHMDS (a 1.06 M THF solution, 4.7 ml, 4.71 mmol), and the mixture was agitated at room temperature for 5 hours. Thereafter, 4.7 ml of a solution of Compound (30) (178 mg, 1.00 mmol) in THF was added dropwise thereto at −78° C., and the mixture was agitated at room temperature for 4 hours. The reaction was terminated with the addition of AcOH, EtOAc was added thereto, and the resultant was washed with a 2N HCl aqueous solution. The organic phase was dried over Na$_2$SO$_4$ and then concentrated. The resulting crude product was purified via column chromatography (silica gel: 51 g; hexane:EtOAc=5:1), and Compound (31) was obtained as a 3:1 diastereomer mixture at position 9a in the form of a yellow solid material (159 mg, 49%).

[α]$^{27}$$_D$+10.2 (c, 1.0, CHCl$_3$);

IR (KBr) 3056, 2957, 1755, 1531, 1428, 1264, 739 cm$^{-1}$;

$^1$H-NMR (400 MHz, CDCl$_3$) 7.85 (d, 2H, J=0.8 Hz, Ph), 7.54-7.46 (m, 3H, Ph), 6.38 (s, 1H, C=C[H](Ph)), 3.97 (dd, 1H, J=11.2, 5.2 Hz, C[H](OTBS)), 2.63 (dd, 1H, J=12.0, 3.6 Hz, CH$_2$C[H]CO), 2.20 (dd, 1H, J=14.4, 2.0 Hz, ½C[H$_2$]CHCO), 1.83-1.78 (m, 1H, ½C[H$_2$]CH(OTBS)), 1.56 (dd, 1H, J=12.4, 6.8 Hz, (CH$_3$)$_2$C[H]CH), 1.49-1.40 (m, 1H, (CH)$_2$CHC[H]), 1.29 (s, 3H, C(C[H$_3$])CH(OTBS)), 1.22-1.21 (m, 1H, ½C[H$_2$CHOSi(CH$_3$)$_2$(CH$_3$)$_3$), 1.11-1.01 (m, 1H, ½C[H$_2$]CH(OTBS)), 0.96 (s, 9H, Si(CH$_3$)$_2$C(C[H$_3$])$_3$), 0.92 (dd, 6H, J=6.8, 2.4 Hz, (C[H$_3$])CHCH), 0.20 (s, 3H, ½ Si(C[H$_3$])$_2$C(Cl$_3$)$_3$), 0.15 (s, 3H, ½ Si(C[H$_3$])$_2$C(CH$_3$)$_3$);

$^{13}$C-NMR (100 MHz, CDCl$_3$) δ 188.1, 173.9, 165.2, 157.6, 132.8, 129.5, 126.8, 100.0, 97.2, 89.5, 76.2, 51.6, 40.5, 36.0, 32.3, 30.0, 26.1, 24.4, 20.1, 18.5, 11.2, −4.1, −4.5;

HRMS (ESI, TFANa) [M+Na]$^+$ calcd for C$_{28}$H$_{38}$NaO$_5$Si: 505.2386; found: 505.2367.

2) Synthesis of (5aS,6S,8S,9aS,10R)-6,10-dihydroxy-8-isopropyl-5a-methyl-3-phenyl-6,7,8,9,9a,10-hexahydropyrano[4,3-b]chromen-1(5aH)-one ((9aS,10R)-32) and (5aS,6S,8S,9aS,10S)-6, 0-dihydroxy-8-isopropyl-5a-methyl-3-phenyl-6,7,8,9,9a 10-hexahydropyrano[4,3-b]chromen-1(5aH)-one ((9aS,10S)-32)

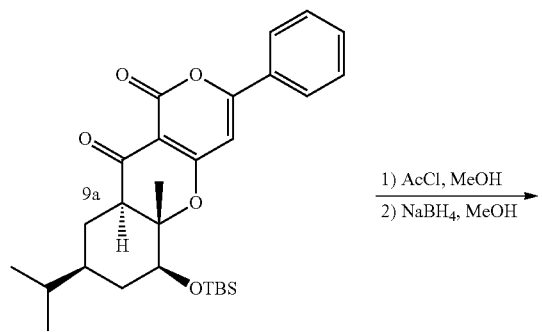

31
(dr = 3:1 from NMR)

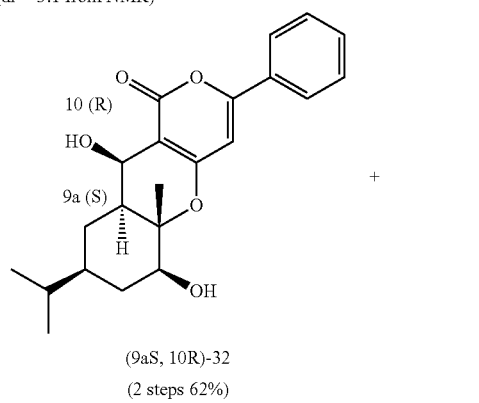

(9aS, 10R)-32
(2 steps 62%)

+

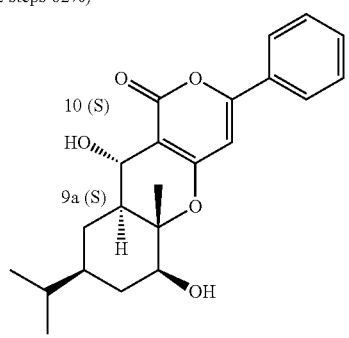

(9aS, 10S)-32
(2 steps 13%)

Under a nitrogen atmosphere, 0.3 ml of a solution of AcCl (7 μl, 100 μmol) in MeOH was added dropwise to 0.3 ml of a solution of Compound (31) (24.0 mg, 49.8 μmol) in MeOH, and the mixture was agitated at room temperature for 2 hours, followed by concentration.

NaBH₄ (2.2 mg, 60.0 μmol) was added to 0.5 ml of a solution of the residue obtained above in MeOH, and the mixture was agitated at 0° C. for 15 minutes. The reaction was terminated with the addition of acetone, EtOAc was added thereto, and the reaction product was washed with water. The combined organic phases were dried over Na₂SO₄ and then concentrated. The resulting crude product was purified via preparative TLC (hexane:EtOAc=1:2), and Compound ((9aS,10R)-32) (11.4 mg, 62%) and Compound ((9aS,10S)-32 (2.4 mg, 13%)) were obtained separately as white solid materials. Identification data for Compound ((9aS,10R)-32)

$[\alpha]^{27}_D$+27.0 (c, 1.0, CHCl₃);

IR (KBr) 3055, 2984, 2307, 1674, 1563, 1427, 1265, 745 cm⁻¹;

¹H-NMR (400 MHz, CDCl₃) δ 7.81-7.79 (m, 2H, Ph), 7.48-7.44 (m, 3H, Ph), 6.48 (s, 1H, PhC=C[H]), 4.65 (d, 1H, J=4.0 Hz, CHC[H](OH)), 3.80 (dd, 1H, J=11.6, 4.8 Hz, CH₂C[H](OH)), 2.00-1.95 (m, 1H, ½C[H₂]CH(OH)), 1.83-1.76 (m, 2H, ½C[H₂]CHCH(OH)), CH₂C[H]CH(OH)), 1.62-1.52 (m, 3H, ½C[H₂]CHCH(OH), (CH₃)₂C[H]CH, (CH₃)₂CHC[H]), 1.44 (s, 3H, CC(C[H₃])O), 1.34-1.21 (m, 1H, ½C[H₂]CH(OH)), 0.96 (d, 3H, J=4.4 Hz, (C[H₃])₂CHCH), 0.93 (d, 3H, J=4.4 Hz, (C[H₃])₂CHCH);

¹³C-NMR (100 MHz, CDCl₃) δ 164.9, 163.8, 160.4, 131.4, 129.3, 126.0, 103.0, 98.6, 84.9, 76.4, 62.1, 43.4, 41.6, 34.3, 32.6, 30.4, 28.1, 23.0, 20.4, 20.2, 14.5, 12.0;

HRMS (ESI, TFANa) [M+Na]⁺ calcd for C₂₂H₂₆NaO₅: 393.1678; found: 393.1670.

Identification Data for Compound ((9aS,10S)-32)

$[\alpha]^{27}_D$+39.7 (c, 1.0, CHCl₃);

IR (KBr) 3054, 2369, 2342, 1693, 1265, 745 cm⁻¹;

¹H-NMR (400 MHz, CDCl₃) δ 7.80-7.76 (m, 2H, Ph), 7.47-7.43 (m, 3H, Ph), 6.48 (s, 1H, PhC=C[H]), 4.46 (d, 1H, J=10.0 Hz, CHC[H](OH)), 3.85 (dd, 1H, J=11.6, 4.8 Hz, CH₂C[H](OH)), 2.31-2.25 (m, 1H, ½C[H₂]CHCH(OH)), 2.00-1.95 (m, 1H, ½C[H₂]CH(OH)), 1.78 (ddd, 1H, J=14.0, 10.0, 4.0 Hz, CH₂C[H]CH(OH)), 1.59-1.52 (m, 1H, (C[H₃])₂ C[H]CH)), 1.42-1.36 (m, 1H, (CH₃)₂CHC[H])), 1.29-1.19 (m, 1H, ½C[H₂]CH(OH)), 1.23 (s, 3H, CC(C[H₃])O), 1.01-0.95 (m, 1H, ½C[H₂]CHCH(OH)), 0.95 (d, 3H, J=3.6 Hz, (C[H₃])₂CHCH), 0.92 (d, 3H, J=3.6 Hz, (C[H₃])₂CHCH):

¹³C-NMR (100 MHz, CDCl₃) δ 164.6, 164.0, 163.9, 131.5, 129.3, 126.0, 102.5, 98.6, 86.0, 75.9, 63.8, 44.7, 41.0, 34.2, 32.6, 30.0, 29.3, 23.0, 20.3, 20.2, 11.3;

HRMS (ESI, TFANa) [M+Na]⁺ calcd for C₂₂H₂₆NaO₅: 393.1678; found: 393.1690.

3) Synthesis of (5aS,6S,8S,9aS,10R)-10-hydroxy-8-isopropyl-5a-methyl-1-oxo-3-phenyl-1,5a,6,7,8,9,9a,10-octahydropyrano[4,3-b]chromen-6-yl acetate ((10R)-33) (PT003)

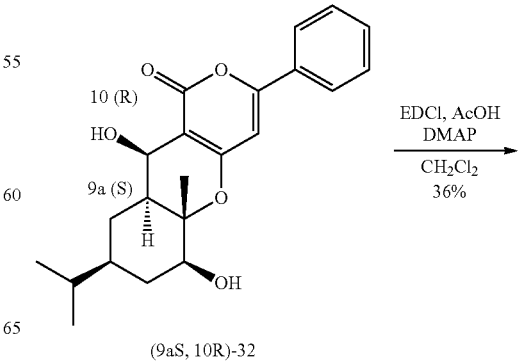

(9aS, 10R)-32

-continued

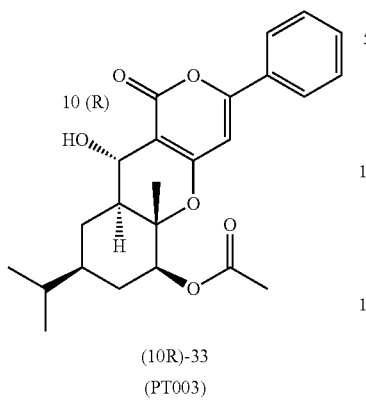

(10R)-33
(PT003)

Under a nitrogen atmosphere, DMAP (2.0 mg, 11.3 µmol), EDCl (2.3 mg, 13.5 µmol), and AcOH (1 µl, 13.5 µmol) were added to 0.1 ml of a solution of Compound ((9aS,10R)-32) (4.2 mg, 11.3 µmol) in $CH_2Cl_2$, and the mixture was agitated at 0° C. for 1 hour. The reaction was terminated with the addition of $H_2O$, and the reaction product was subjected to extraction with $CH_2Cl_2$. The combined organic phases were dried over $Na_2SO_4$ and then concentrated. The resulting crude product was purified via preparative TLC (hexane:EtOAc=1:1), and Compound ((10R)-33) (PT003) was obtained as a white solid material (1.9 mg, 36%).

$[\alpha]^{27}_D$ +21.8 (c, 0.1, $CHCl_3$);

IR (KBr) 2927, 1736, 1689, 1636, 1571, 1424, 1381, 1258, 733 $cm^{-1}$;

$^1$H-NMR (300 MHz, $CDCl_3$) δ 7.81-7.79 (m, 2H, Ph), 7.47-7.43 (m, 3H, Ph), 6.43 (s, 1H, PhC=C[H]), 5.02 (dd, 1H, J=11.7, 4.8 Hz, C[H](OAc)), 4.64 (d, 1H, J=4.5 Hz, CHC[H](OH)), 2.21 (s, 3H, OCHC(C[H$_3$])), 2.01-1.95 (m, 1H, ½C[H$_2$]CH(OAc)), 1.90-1.80 (m, 2H, ½C[H$_2$]CHCH (OH), CH$_2$C[H]CH(OH)), 1.65-1.42 (m, 3H, ½ C[H$_2$] CHCH(OH), (CH$_3$)$_2$C[H]CH, (CH$_3$)$_2$CHC[H]), 1.48 (s, 3H, CC(C[H$_3$])O), 1.37-1.29 (m, 1H, ½C[H$_2$]CH(OAc)), 0.95 (d, 3H, J=4.5 Hz, (C[H$_3$])$_2$CHCH), 0.93 (d, 3H, J=4.5 Hz, (C[H$_3$])$_2$CHCH);

$^{13}$C-NMR (75 MHz, $CDCl_3$) δ 170.7, 164.5, 163.8, 160.3, 131.4, 129.3, 126.0, 102.8, 82.6, 62.1, 43.7, 41.5, 32.6, 32.5, 30.1, 27.8, 21.7, 20.2, 20.1, 13.0;

HRMS (ESI, TFANa) [M+Na]$^+$ calcd for $C_{24}H_{28}NaO_6$: 435.1784; found: 435.1773.

Example 61

Production of (5aS,6S,8S,9aS,10S)-0-hydroxy-8-isopropyl-5a-methyl-1-oxo-3-phenyl-1,5a,6,7,8,9,9a, 10-octahydropyrano[4,3-b]chromen-6-yl acetate ((10S)-33) (PT004)

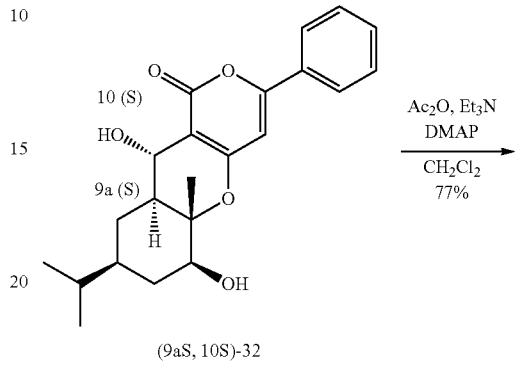

DMAP (3.7 mg, 3.27 µmol), Et$_3$N (10 µl, 71.9 µmol), and Ac$_2$O (4 µl, 3.59 µmol) were added to 0.3 ml of a solution of Compound ((9aS,10S)-32) (12.1 mg, 32.7 µmol) obtained in Example 5 in $CH_2Cl_2$, and, under a nitrogen atmosphere, the mixture was agitated at −10° C. for 30 minutes. The reaction was terminated with the addition of $H_2O$, and the reaction product was subjected to extraction with $CH_2Cl_2$. The combined organic phases were dried over $Na_2SO_4$ and then concentrated. The resulting crude product was purified via preparative TLC (hexane:EtOAc=1:20), and Compound ((10S)-33) (PT004) was obtained as a white solid material (9.5 mg, 77%).

$[\alpha]^{27}_D$ +37.5 (c, 1.0, $CHCl_3$);

IR (KBr) 2927, 1736, 1689, 1263, 740 $cm^{-1}$;

$^1$H-NMR (300 MHz, $CDCl_3$) δ 7.81-7.77 (m, 2H, Ph), 7.47-7.26 (m, 3H, Ph), 6.42 (s, 1H, PhC=C[H]), 5.05 (dd, 1H, J=11.7, 4.8 Hz, C[H](OAc)), 4.45 (d, 1H, J=10.2 Hz, CHC[H](OH)), 2.34-2.23 (m, 1H, ½C[H$_2$]CHCH(OH)), 2.18 (s, 3H, C[H$_3$]CO$_2$), 2.04-1.94 (m, 1H, ½C[H$_2$]CH(OAc)), 1.86 (ddd, 1H, J=12.3, 10.2, 3.6 Hz, CH$_2$C[H]CH(OH)), 1.59-1.43 (n, 2H, (CH$_3$)$_2$C[H]CH, (CH$_3$)$_2$CHC[H]), 1.33-1.27 (m, 1H, ½C[H$_2$]CH(OAc)), 1.28 (s, 3H, CC(C[H$_3$])O), 1.02-0.87 (m, 1H, ½C[H$_2$]CHCH(OH)), 0.93 (d, 3H, J=4.8 Hz, (C[H$_3$])$_2$CHCH), 0.91 (d, 3H, J=4.8 Hz, (C[H$_3$])$_2$ CHCH);

$^{13}$C-NMR (100 MHz, $CDCl_3$) δ 170.7, 164.2, 163.5, 160.3, 131.4, 129.3, 126.0, 102.8, 83.2, 76.3, 63.3, 44.7, 41.5, 32.6, 32.5, 32.2, 30.1, 27.8, 21.7, 20.2, 20.1, 12.0;

HRMS (ESI, TFANa) [M+Na]⁺ calcd for $C_{24}H_{28}NaO_6$: 435.1784; found: 435.1775.

Example 7

Production of (5aS,6S,8S,9aS,10R)-10-hydroxy-8-isopropyl-5a-methyl-1-oxo-3-phenyl-1,5a,6,7,8,9,9a,10-octahydropyrano[4,3-b]chromen-6-yl 4-cyanobenzoate (34) (PT007)

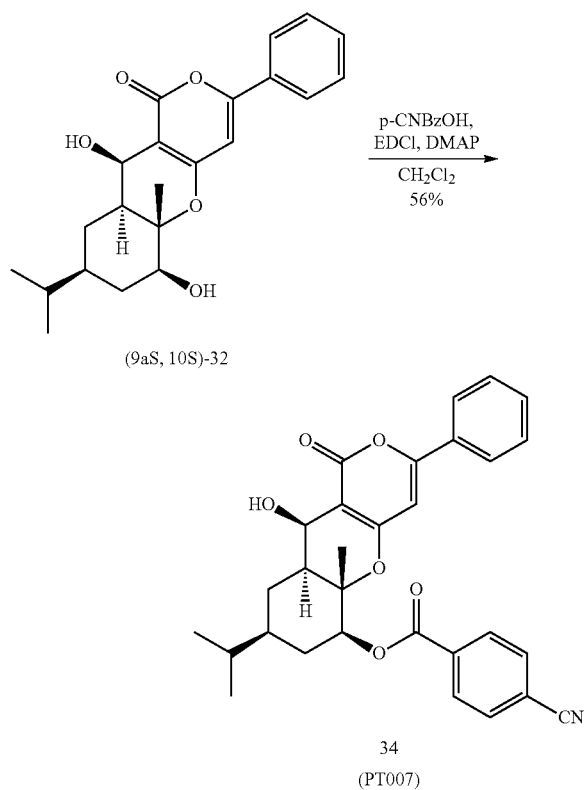

Under a nitrogen atmosphere, EDCl (14.2 mg, 0.074 mmol), DMAP (8.4 mg, 0.069 mmol), and p-CNBzOH (9.0 mg, 0.055 mmol) were added to 0.5 ml of a solution of Compound ((9aS,10S)-32) (17.0 mg, 0.046 mmol) in $CH_2Cl_2$ at room temperature, and the mixture was agitated at room temperature for 2.5 hours. The reaction was terminated with the addition of MeOH, and the reaction product was subjected to extraction with $Cl_2Cl_2$. Thereafter, the organic phase was dried over $Na_2SO_4$ and then concentrated. The resulting crude product was purified via preparative TLC (hexane:EtOAc=3:1), and Compound (34) (PT007) was obtained as a white solid material (12.8 mg, 56%).

$[\alpha]^{27}_D$+68.6 (c, 1.0, $CHCl_3$);

IR (KBr) 3436, 2958, 2230, 1723, 1637, 1575, 1415, 1269, 1209, 1100, 757, 472 cm⁻¹;

¹H-NMR (400 MHz, $CDCl_3$) δ 8.24-8.21 (m, 1H, Ph), 8.16-8.13 (m, 1H, Ph), 7.83-7.80 (m, 2H, Ph), 7.78-7.73 (m, 3H, Ph, C(O)[Ph]CN), 7.46-7.40 (m, 2H, C(O)[Ph]CN), 6.39-6.34 (m, 1H, PhC=C[H]), 5.37-5.33 (m, 1H, C[H]OC(O)PhCN), 4.14-4.10 (m, 1H, CHC[H](OH)), 2.27-2.23 (m, 1H, ½C[H₂]CHCH(OH)), 2.16-2.13 (m, 1H, ½CHC[H₂]CHOC(O)PhCN), 2.05 (s, 1H, C[H]CH(OH)), 1.71-1.74 (bs, 31, C[H₃]COC=C), 1.55-1.15 (m, 4H, C[H](CH₃)₂, C[H]CH(CH₃)₂, C[H₂]CHCH(OH)), 0.84 (m, 6H, (C[H₃])₂CHCH);

¹³C-NMR (150 MHz, $CDCl_3$) δ 164.2, 163.5, 160.1, 131.1, 131.0, 129.0, 125.6, 102.1, 98.2, 85.6, 75.5, 65.7, 65.6, 63.4, 44.4, 40.7, 33.9, 32.2, 31.9, 29.7, 29.3, 29.0, 28.5, 25.8, 24.7, 22.7, 20.0, 19.8, 14.1, 10.9;

HRMS (ESI) [M+Na]⁺ calcd for $C_{30}H_{29}NNaO_6$: 522.1893; found: 522.1915.

Example 8

Production of (5aS,6S,8S,9aS,10R)-10-hydroxy-8-isopropyl-5a,9,9-trimethyl-1-oxo-3-(pyridin-3-yl)-1,5a,6,7,8,9,9a,10-octahydropyrano[4,3-b]chromen-6-yl acetate (35) (PT008)

1) Synthesis of (S,4S,6S)-4-isopropyl-1,3,3-trimethyl-7-oxabicyclo[4.1.0]heptan-2-one (10)

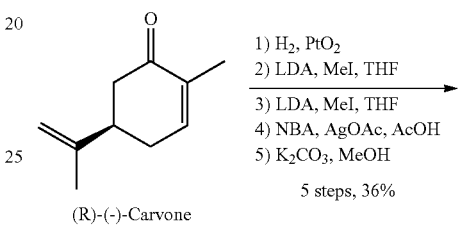

$PtO_2$ (21.7 mg, 0.096 mmol) was added to (R)-(−)-carvone (15.0 ml, 95.5 mmol), and, under a hydrogen atmosphere, the mixture was agitated at room temperature for 23 hours. The reaction solution was filtered through Celite, and the resulting crude product was subjected to the subsequent reaction in an unpurified state.

Under an argon atmosphere, n-BuLi (53.3 ml, 143 mmol) was added to 280 ml of a solution of i-Pr₂NH (20.2 ml, 143 mmol) in THF, and the mixture was agitated at 0° C. for 1 hour. Thereafter, 20 ml of a solution of the crude product in THF was added, and the mixture was agitated for 3 hours. MeI (20.8 ml, 334 mmol) was added, and the mixture was agitated for 12 hours. After the reaction was terminated with the addition of NH₄Cl, the resultant was diluted with EtOAc, and the organic phase was washed with water, followed by drying over Na₂SO₄. The resultant was concentrated, the resulting crude product was roughly purified via column chromatography (silica gel: 460 g; 100:1 hexane/EtOAc), and a fraction containing a product was concentrated to obtain a crude product.

Under an argon atmosphere, n-BuLi (88.7 ml, 239 mmol) was added to 280 ml of a solution of iPr₂NH (33.7 ml, 239 mmol) in THF, and the mixture was agitated at 0° C. for 1 hour. Thereafter, 20 ml of a solution of the crude product in THF was added, the mixture was agitated at room temperature for 6 hours, MeI (20.8 ml, 334 mmol) was added thereto, and the mixture was agitated for an additional 12 hours. After the reaction was terminated with the addition of a saturated NH₄Cl aqueous solution, the resultant was diluted with EtOAc, and the organic phase was washed with water, followed by drying over $Na_2SO_4$. The resultant was concentrated, the resulting crude product was roughly purified via column chromatography (silica gel: 400 g; 100:1 hexane/EtOAc), and a fraction containing a product was concentrated to obtain a crude product.

NBA (26.3 g, 191 mmol) and AgOAc (31.9 g, 191 mmol) were added to 318 ml of a solution of the resulting crude product in AcOH, and the mixture was agitated at room temperature for 4 hours. The reaction solution was filtered through Celite, a saturated $NaHCO_3$ aqueous solution was added thereto, and the reaction product was subjected to extraction with EtOAc. The organic phase was dried over $Na_2SO_4$ and then concentrated. The resulting crude product was roughly purified via column chromatography (silica gel:1120 g; hexane:EtOAc=20:1), and a fraction containing a product was concentrated to obtain a crude product.

$K_2CO_3$ (39.6 g, 286 mmol) was added to 318 ml of a solution of the resulting crude product in MeOH, and the mixture was agitated at room temperature for 30 minutes. The reaction solution was diluted with EtOAc, and the organic phase was washed with $1H_2O$, followed by drying over $Na_2SO_4$ and concentration. The resulting crude product was purified via column chromatography (silica gel: 1120 g; hexane:EtOAc=50:1), and Compound (10) was obtained as a yellow oil product (11.7 g, 5-step process, 62%).

$[\alpha]^{27}_D$ −102.7 (c, 1.0, $CHCl_3$);

IR (KBr) 2855, 2363, 2343, 1075, 857, 773, 466 $cm^{-1}$;

$^1$H-NMR (400 MHz, $CDCl_3$) δ 3.42 (d, 1H, J=4.8 Hz, C[H](O)C), 2.15 (dd, 1H, J=15.6, 10.4 Hz, ½C[$H_2$]CH(O)C), 2.02 (ddd, 1H, J=15.6, 6.4, 4.8 Hz, ½C[$H_2$]CH(O)C), 1.96-1.89 (m, 1H, C[H]($CH_3$)$_2$), 1.58-1.53 (m, 1H, C[H]CH($CH_3$)$_2$), 1.38 (s, 3H, C[$H_3$]COCH), 1.16 (s, 3H, C[$H_3$]CCH$_3$), 1.12 (s, 3H, $CH_3$CC[$H_3$]), 0.93 (d, 3H, J=6.8 Hz, CH(C[$H_3$])$_2$), 0.87 (d, 3H, J=7.2 Hz, CH(C[$H_3$])$_2$);

$^{13}$C-NMR (100 MHz, $CDCl_3$) δ 210.5, 63.3, 57.1, 49.9, 47.5, 27.6, 24.8, 24.4, 20.9, 20.8, 18.9, 16.7;

HRMS (EI) [M]$^+$ calcd for $C_{12}H_{20}O_2$: 196.1463; found: 196.1451.

2) Synthesis of 5-((3S,5S)-3-((tert-butyldimethylsilyl)oxy)-5-isopropyl-2,6,6-trimethylcyclohex-1-enecarbonyl)-2,2,6-trimethyl-4H-1,3-dioxin-4-one (12)

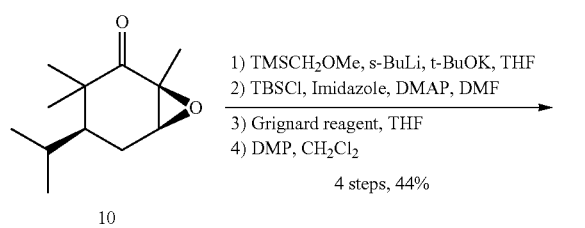

10

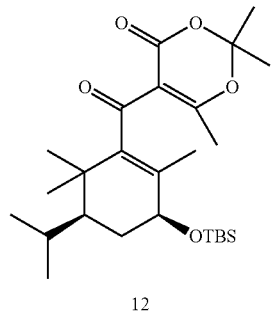

12

Under an argon atmosphere, s-BuLi (a 1.1 M THF solution, 4.46 ml, 4.73 mmol) was added dropwise to 10 ml of a solution of $TMSCH_2OMe$ (0.738 ml, 4.73 mmol) in THF at −23° C., the mixture was agitated at room temperature for 30 minutes, 5.8 ml of a solution of Compound (10) (310 mg, 1.58 mmol) in THF was added dropwise thereto at −78° C., and the mixture was agitated at −60° C. for 40 minutes. Thereafter, the temperature was gradually raised to room temperature with the addition of t-BuOK (708 mg, 6.31 mmol), and the mixture was agitated at room temperature for 1 hour. A saturated $NH_4Cl$ aqueous solution was added thereto, the mixture was agitated for 15 minutes to terminate the reaction. $CH_2Cl_2$ was added thereto, and the organic phase was washed with a 2 N HCl solution, followed by drying over $Na_2SO_4$ and concentration.

Imidazole (430 mg, 6.31 mmol), DMAP (19.3 mg, 0.158 mmol), and TBSCl (713 mg, 4.73 mmol) were added to 16 ml of a solution of the residue obtained above in DMF, and, under a nitrogen atmosphere, the mixture was agitated at 50° C. for 1 hour. The reaction was terminated with the addition of $H_2O$, EtOAc was added, and the organic phase was washed with water. The organic phase was dried over $Na_2SO_4$ and then concentrated. The resulting crude product was roughly purified via column chromatography (silica gel: 51 g; hexane:EtOAc=100:1), and a fraction containing a product was concentrated to obtain a crude product.

Under an argon atmosphere at −30° C., iPrMgCl (a 2.0 M THF solution, 2.37 ml, 4.73 mmol) was added dropwise to 10 ml of a solution of 5-iodo-2,2,6-trimethyl-4H-1,3-dioxin-4-one (Tetrahedron Lett., 2001, Vol. 42, pp. 6847-6850) (845 mg, 3.16 mmol) in THF, the mixture was agitated for 30 minutes, 5.8 ml of a solution of the crude product obtained above in THF was added dropwise thereto, and the mixture was agitated at room temperature for 15 minutes. The reaction was terminated with the addition of a saturated $NH_4Cl$ aqueous solution, and the reaction product was subjected to extraction with $CH_2Cl_2$. The combined organic phases were dried over $Na_2SO_4$ and then concentrated.

Under a nitrogen atmosphere at 0° C., DMP (1.00 g, 2.37 mmol) was added to 16 ml of a solution of the residue obtained above in $CH_2Cl_2$, and the mixture was agitated for 15 minutes. The reaction was terminated with the addition of a saturated $Na_2S_2O_3$ aqueous solution and a saturated $NaHCO_3$ aqueous solution, and the reaction product was subjected to extraction with $CH_2Cl_2$. The organic phase was dried over $Na_2SO_4$ and then concentrated. The resulting crude product was purified via column chromatography (silica gel: 73 g; hexane:EtOAc=10:1), and Compound (12) was obtained as a yellow oil product (321 mg, 4-step process, 44%).

$[\alpha]^{27}_D$+27.7 (c, 1.0, $CHCl_3$);

IR (KBr) 3474, 2957, 2858, 1744, 1656, 1545, 1468, 1377, 1346, 1253, 1198, 1088, 1050, 867, 836 $cm^{-1}$;

$^1$H-NMR (300 MHz, $CDCl_3$) δ 4.18-4.13 (m, 1H, C[H]OTBS), 2.45 (s, 3H, C[$H_3$]COC($CH_3$)$_2$), 1.98-1.89 (m, 1H, C[H]($CH_3$)$_2$), 1.79-1.71 (m, 1H, C[H]CH($CH_3$)$_2$), 1.70 (s, 3H, C[$H_3$]COC=O), 1.69 (s, 3H, C[$H_3$]COC=O), 1.60-1.55 (m, 2H, C[$H_2$]CHOTBS), 1.55 (s, 3H, C[$H_3$]CCHOTBS), 1.13 (s, 3H, C[$H_3$]C($CH_3$)C), 0.95 (s, 3H, C[$H_3$]CH($CH_3$)CH), 0.93 (d, 3H, J=6.9 Hz, C[$H_3$]CH($CH_3$)CH), 0.89 (s, 9H, (C[$H_3$])$_3$CSi), 0.84 (d, 3H, J=6.9 Hz, C[$H_3$]CH($CH_3$)CH), 0.10 (s, 3H, ½ (C[$H_3$])$_2$Si), 0.07 (s, 3H, ½ (C[$H_3$])$_2$Si);

$^{13}$C-NMR (75 MHz, $CDCl_3$) δ 197.6, 179.1, 158.2, 143.4, 132.4, 110.3, 105.8, 77.4, 72.6, 47.3, 39.5, 29.7, 26.0, 25.6, 25.3, 25.3, 25.2, 24.8, 24.6, 23.7, 21.8, 18.8, 18.3, 16.5, −3.8, −4.7;

HRMS (ESI, TFANa) [M+Na]+ calcd for $C_{26}H_{44}NaO_5Si$: 487.2856; found: 487.2841.

3) Synthesis of (4aR,6S,8S,8aS)-methyl-8-((tert-butyldimethylsilyl)oxy)-6-isopropyl-2,5,5,8a-tetramethyl-4-oxo-4a,5,6,7,8,8a-hexahydro-4H-chromene-3-carboxylic acid (13)

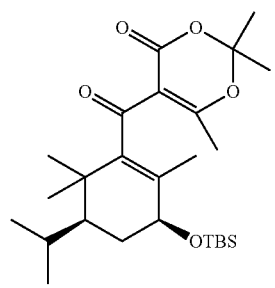

12

1) MeOH, toluene
2) DBU, toluene 4 steps, 69%

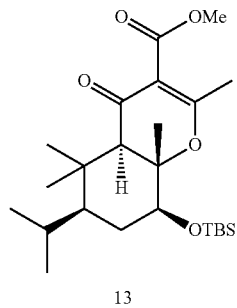

13

Toluene (11 ml) and MeOH (2.7 mil) were added to Compound (12) (622 mg, 1.34 mmol), and the mixture was agitated at 90° C. for 3 hours, followed by concentration.

DBU (0.200 ml, 1.34 mmol) was added to 13 ml of a solution of the residue obtained above in toluene, and the mixture was agitated at 100° C. for 4 hours. The reaction was terminated with the addition of $H_2O$, and the reaction product was subjected to extraction with $CH_2Cl_2$. The organic phase was dried over $Na_2SO_4$ and then concentrated. The resulting crude product was purified via column chromatography (silica gel: 59 g; hexane:EtOAc=25:1), and Compound (13) was obtained as a yellow oil product (407 mg, 69%).

$[\alpha]^{27}_D$+19.9 (c, 0.1, $CHCl_3$);

IR (KBr) 2371, 2345, 1060, 773, 618, 476 $cm^{-1}$;

$^1$H-NMR (400 MHz, $CDCl_3$) δ 3.82 (dd, 1H, J=11.6, 4.8 Hz, CHOTBS), 3.78 (s, 3H, C[$H_3$]OC=O), 2.39 (s, 1H, C[H]C=O), 2.13 (s, 3H, C[$H_3$]C=C), 2.02-1.97 (m, 1H, C[H](CH$_3$)$_2$), 1.52 (ddd, 1H, J=13.2, 4.8, 3.2 Hz, ½C[$H_2$]CHOTBS), 1.39-1.29 (m, 1H, ½C[$H_2$]CHOTBS), 1.31 (s, 3H, C[$H_3$]CCHOTBS), 1.25 (s, 31-1H, C[$H_3$]CCH$_3$), 1.04-1.00 (m, 1H, C[H]CH(CH$_3$)$_2$), 1.03 (s, 3H, C[$H_3$]CCH$_3$), 0.90 (d, 3H, J=6.8 Hz, C[$H_3$]CH(CH$_3$)CH), 0.91 (s, 9H, (C[$H_3$])CSi), 0.79 (d, 3H, J=6.8 Hz, C[$H_3$]CH(CH$_3$)CH), 0.10 (s, 3H, ½ (C[$H_3$])$_2$Si), 0.10 (s, 3H, ½ (C[$H_3$])$_2$Si);

$^{13}$C-NMR (100 MHz, $CDCl_3$) δ 189.3, 174.0, 166.6, 111.5, 87.9, 77.2, 58.9, 52.0, 51.3, 37.8, 29.4, 28.9, 25.9, 25.2, 24.6, 20.6, 19.0, 18.3, 16.9, 13.5, -4.4, -4.4;

HRMS (ESI, TFANa) [M+Na]+ calcd for $C_{24}H_{42}NaO_5Si$: 461.2699; found: 461.2697.

4) Synthesis of (5aS,6S,8S,9aR)-6-((tert-butyldimethylsilyl)oxy)-8-isopropyl-5a,9,9-trimethyl-3-(pyridin-3-yl)-5a,6,7,8,9,9a-hexahydropyrano[4,3-b]chromene-1,10-dione (14)

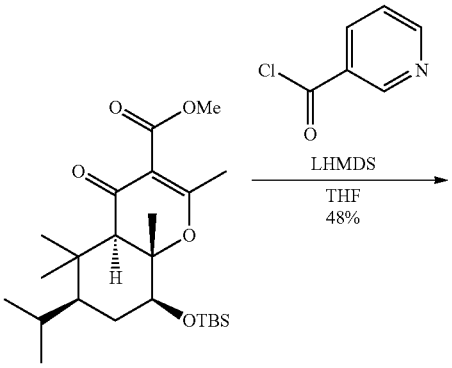

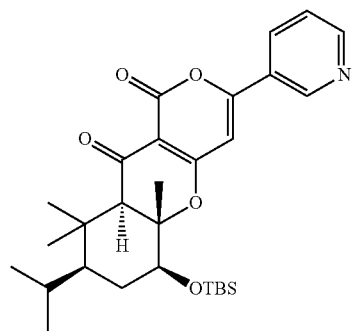

14

Under an argon atmosphere, 1.2 ml of a solution of Compound (13) (93.0 mg, 0.212 mmol) in THF was added dropwise to 1.0 ml of a solution of LHMDS (a 1.06 M THF solution, 2.12 ml, 0.212 mmol) in THF at -78° C., and the mixture was agitated at room temperature for 4 hours. Thereafter, nicotinoyl chloride hydrochloride (113 mg, 0.637 mmol) was added at -78° C., the mixture was agitated at 0° C. for 15 minutes, and the mixture was then agitated at room temperature for 2 hours. After the reaction was terminated with the addition of AcOH, 3 g of silica gel was added to concentrate the reaction product, the resultant was purified via column chromatography (silica gel: 7.8 g; hexane:EtOAc=5:1), and Compound (14) was obtained as a yellow oil product (52.0 mg, 48%).

IR (KBr) 2965, 2361, 2343, 1262, 1075, 750, 669, 647, 483, 468, 428 $cm^{-1}$;

$^1$H-NMR (400 MHz, $CDCl_3$) δ 9.04 (br s, 1H, Py), 8.75 (br s, 1H, Py), 8.17 (d, 1H, J=8.0 Hz, Py), 7.47-7.46 (m, 1H, Py), 6.38 (s, 1H, C[H]=C), 3.94 (dd, 1H, J=11.6, 4.8 Hz, C[H]OTBS), 2.54 (s, 1H, C[H]C=O=O), 2.08-1.99 (m, 1H, C[H](CH$_3$)$_2$), 1.62-1.56 (m, 2H, C[$H_2$]CHOTBS), 1.30 (s, 3H, C[$H_3$]CCHOTBS), 1.24 (s, 3H, C[$H_3$]CCH$_3$), 1.11 (s, 3H, C[$H_3$]CCH$_3$), 1.11-1.06 (m, 1H, C[H]CH(CH$_3$)$_2$), 0.95 (s, 9H, (C[$H_3$])$_3$CSi), 0.93 (d, 3H, J=7.2 Hz, C[$H_3$]CH(CH$_3$)CH), 0.80 (d, 3H, J=6.4 Hz, C[$H_3$]CH(CH$_3$)CH), 0.18 (s, 3H, ½ (C[$H_3$])$_2$Si), 0.15 (s, 3H, ½ (C[$H_3$])$_2$Si);

$^{13}$C-NMR (100 MHz, $CDCl_3$) δ 187.5, 172.4, 161.9, 157.1, 151.9, 146.9, 134.5, 100.9, 98.1, 90.8, 90.5, 77.4, 76.9, 60.4, 51.1, 38.2, 29.8, 29.4, 28.8, 25.9, 25.2, 24.6, 22.8, 18.9, 18.3, 16.8, 14.2, -4.2, -4.3;

HRMS (ESI, TFANa) [M+Na]⁺ calcd for $C_{29}H_{41}NNaO_5$: 534.2652; found: 534.2658.

5) Synthesis of (5aS,6S,8S,9aS,10R)-10-hydroxy-8-isopropyl-5a,9,9-trimethyl-1-oxo-3-(pyridin-3-yl)-1,5a,6,7,8,9,9a,10-octahydropyrano[4,3-b]chromen-6-yl acetate (35) (PT008)

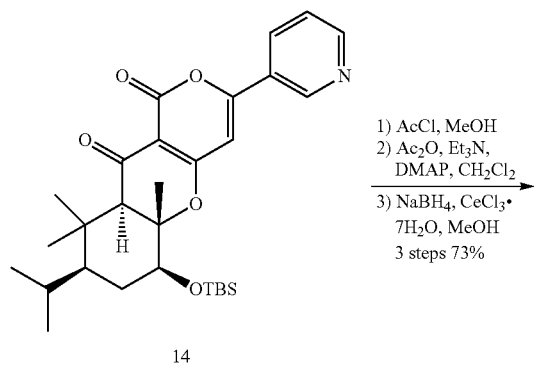

Compound (14) (20.0 mg, 0.0391 mmol) was dissolved in a solvent mixture of MeOH (0.6 ml) and THF (0.2 ml), AcCl (0.028 ml, 0.391 mmol) was added at 0° C., and the mixture was agitated for 1 hour, followed by concentration.

Under a nitrogen atmosphere, Et₃N (0.038 ml, 0.274 mmol), a catalytic amount of DMAP, and Ac₂O (0.013 ml, 0.137 mmol) were added to 0.8 ml of a solution of the residue obtained above in CH₂Cl₂ at room temperature, and the mixture was agitated at room temperature for 1 hour. The reaction was terminated with the addition of MeOH, a solution supplemented with water was subjected to extraction with CH₂Cl₂, and the combined organic phases were dried over Na₂SO₄, followed by concentration.

The residue obtained above was dissolved in 0.6 ml of MeOH and 0.2 ml of THF, CeCl₃·7H₂O (18.9 mg, 0.0510 mmol) and NaBH₄ (1.9 mg, 0.0510 mmol) were added thereto at −78° C., and the mixture was agitated at 0° C. for 30 minutes. The reaction was terminated with the addition of acetone, and a solution supplemented with water was subjected to extraction with CH₂Cl₂. The combined organic phases were dried over Na₂SO₄ and then concentrated. The resulting crude product was purified via preparative TLC (hexane:EtOAc=1:2), and Compound (35) (PT008) was obtained as a white solid material (12.6 mg, 3-step process, 73%).

$[\alpha]^{27}_D$+58.3 (1.0, CHCl₃);
IR (KBr) 3433, 2361, 1638, 1241, 1041, 804, 669, 535, 418 cm⁻¹;

¹H-NMR (400 MHz, CDCl₃) δ 9.03 (br s, 1H, Py), 8.70 (br s, 1H, Py), 8.13 (d, 1H, J=8.4 Hz, Py), 7.44 (bs, 1H, Py), 6.47 (s, 1H, C[H]=C), 5.05 (d, 1H, J=4.0 Hz, C[H](OH)CH), 5.00 (dd, 1H, J=12.0, 4.8 Hz, C[H]OAc), 2.82 (bs, 1H, [H]OCH), 2.18 (s, 3H, C[H₃]C(O)OCH), 2.06-1.99 (m, 1H, C[H](CH₃)₂), 1.79 (ddd, 1H, J=13.2, 4.8, 3.2 Hz, ½C[H₂]CHOAc), 1.67 (s, 3H, C[H₃]CCHOAc), 1.54 (m, 2H, C[H]CH(OH), C[H]CH(CH₃)₂), 1.32 (m, 1H, ½C[H₂]CHOAc), 1.28 (s, 3H, C[H]C(CH₃)CH), 1.23 (s, 3H, C[H₃]C(CH₃)CH), 0.96 (d, 3H, J=6.8 Hz, C[H₃]CHCH₃), 0.85 (d, 3H, J=6.8 Hz, C[H₃]CHCH₃);
¹³C-NMR (75 MHz, CDCl₃) 170.5, 161.7, 126.5, 105.0, 102.2, 84.3, 78.0, 77.4, 60.6, 53.0, 51.5, 39.8, 29.9, 27.8, 26.3, 25.6, 25.4, 21.6, 19.1, 19.1, 15.9, 15.8;
HRMS (ESI) [M+Na]⁺ calcd for $C_{25}H_{31}NNaO_6$: 464.2049; found: 464.2048.

Example 9

Production of (5aS,6S,8S,9aS,10R)-10-hydroxy-8-isopropyl-5a,9,9-trimethyl-1-oxo-3-(pyridin-3-yl)-1,5a,6,7,8,9,9a,10-octahydropyrano[4,3-b]chromen-6-yl 4-cyanobenzoate (15) (PT009)

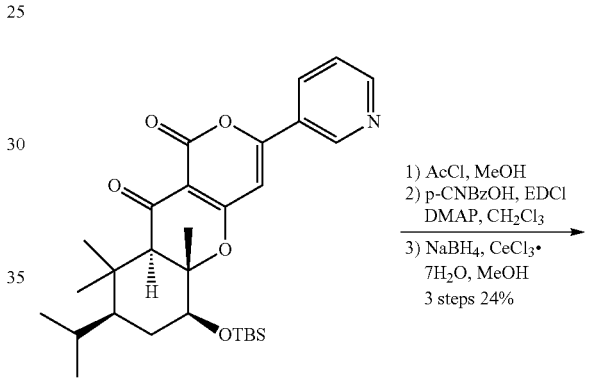

Compound (14) (40.0 mg, 0.078 mmol) obtained in Example 8 was dissolved in a solvent mixture of MeOH (0.6 ml) and THF (0.2 ml), AcCl (0.056 ml, 0.782 mmol) was added thereto at 0° C., and the mixture was agitated for 1 hour, followed by concentration.

Under a nitrogen atmosphere, EDCl (27.0 mg, 0.141 mmol), a catalytic amount of DMAP, and p-CNBzOH (17.3 mg, 0.117 mmol) were added to 1.6 ml of a solution of the residue obtained above in CH₂Cl at room temperature, and the mixture was agitated at room temperature for 30 minutes. The reaction was terminated with the addition of H₂O, CH$_2$Cl$_2$ was added, and the organic phase was washed with 1 N HCl and a saturated NaHCO$_3$ aqueous solution. The resulting organic phase was dried over Na$_2$SO$_4$ and then concentrated.

The residue obtained above was dissolved in a solvent mixture of MeOH (1.3 ml) and THF (0.3 ml), CeCl$_3$.7H$_2$O (37.8 mg, 0.106 mmol) and NaBH$_4$ (3.8 mg, 0.106 mmol) were added thereto at −78° C., and the mixture was agitated at 0° C. for 30 minutes. The reaction was terminated with the addition of acetone, and a solution supplemented with water was subjected to extraction with Cl$_2$Cl$_2$. The combined organic phases were dried over Na$_2$SO$_4$ and then concentrated. The resulting crude product was purified via preparative TLC (hexane:EtOAc=1:2), and Compound (15) (PT009) was obtained as a white solid material (10.0 mg, 3-step process, 240/o).

[α]$^{27}_D$+88.3 (c, 0.1, CHCl$_3$);
IR (KBr) 3433, 3020, 2360, 2341, 1637, 1216, 772, 669 cm$^{-1}$;
$^1$H-NMR (400 MHz, CDCl$_3$) δ 8.99 (br s, 1H, Py), 8.68 (br s, 1H, Py), 8.23 (d, 2H, J=8.4 Hz, p-CN[Bz]), 8.14 (br s, 1H, Py), 7.80 (d, 2H, J=8.0 Hz, p-CN[Bz]), 7.45 (br s, 1H, Py), 6.41 (s, 1H, C[H]=C), 5.28 (dd, 1H, J=12.2, 5.0 Hz, C[H]Op-CNBz), 5.09 (d, 1H, J=3.6 Hz, C[H](OH)CH), 2.85 (br s, 1H, [H]OCH), 2.10-2.04 (m, 1H, C[H](CH$_3$)$_2$), 1.92 (ddd, 1H, J=13.0, 4.8, 3.2 Hz, ½C[H$_2$]CHOp-CNBz), 1.82 (s, 3H, C[H$_3$]CCHOp-CNBz), 1.70 (m, 1H, C[H]CH(CH$_3$)$_2$), 1.62 (d, 1H, J=4.0 Hz, C[H]CH(OH)), 1.28 (s, 3H, C[H$_3$]C(CH$_3$)CH), 1.25 (m, 4H, C[H$_3$]C(CH$_3$)CH, C[H$_2$]CHOp-CNBz), 0.98 (d, 3H, J=6.8 Hz, C[H$_3$]CHCH$_3$), 0.86 (d, 3H, J=6.4 Hz, C[H$_3$]CHCH$_3$);
HRMS (ESI, TFANa) [M+Na]$^+$ calcd for C$_{31}$H$_{32}$N$_2$NaO$_6$: 551.2158; found: 511.2171.

Example 10

Production of 2-((5aS,6S,8S,9aS,10R)-6-acetoxy-10-hydroxy-5a,9,9-trimethyl-1-oxo-3-(pyridin-2-yl)-1,5a,6,7,8,9,9a,10-octahydropyrano[4,3-b]chromen-8-yl)propane-1,3-diyl diacetate (26) (PT010)

1) Synthesis of (R)-5-(3-chloroprop-1-en-2-yl)-2,6,6-trimethylcyclohex-2-enone (17)

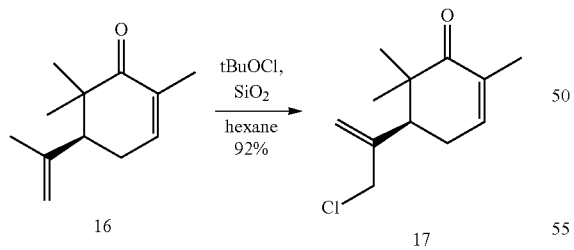

Silica gel (4.8 g) was added to 38 ml of a solution of α,α-dimethylcarvone (16) (1.71 g, 9.59 mmol) (Srikrishna, A. et al., Chem. Commun., 1996, Vol. 11, pp. 1369-1370) in hexane, t-BuOCl (1.19 ml, 10.5 mmol) was added dropwise thereto at −30° C., and the mixture was agitated at room temperature for 40 minutes. The reaction was terminated with the addition of a saturated Na$_2$S$_2$O$_3$ aqueous solution, the reaction product was filtered through Celite, EtOAc was added thereto, and the organic phase was then washed with water. The organic phase was dried over Na$_2$SO$_4$ and then concentrated. The resulting crude product was purified via column chromatography (silica gel: 36.8 g; hexane:EtOAc=80:1), and Compound (17) was obtained as a yellow oil product (1.76 g, 93%).

$^1$H-NMR (300 MHz, CDCl$_3$) S 6.61 (m, 1H, C[H]=CCH$_3$), 5.37 (s, 1H, ½C[H$_2$]=C), 5.08 (s, 1H, ½C[H$_2$]=C), 4.04 (m, 2H, C[H$_2$]Cl), 2.72 (t, 1H, J=7.2 Hz, C[H]C(Cl$_3$)$_2$), 2.45 (m, 2H, C[H$_2$]CH), 1.78 (m, 3H, C[H$_3$]C=CH), 1.10 (s, 3H, C[H$_3$]CCH$_3$), 1.02 (s, 3H, C[H$_3$]CCH$_3$);
HRMS (EI) [M]$^+$ calcd for C$_2$H$_{17}$ClO: 212.0968; found: 212.0976.

2) Synthesis of (S)-5-(3-hydroxypropyl-en-2-yl)-2,6,6-trimethylcyclohex-2-enone (36)

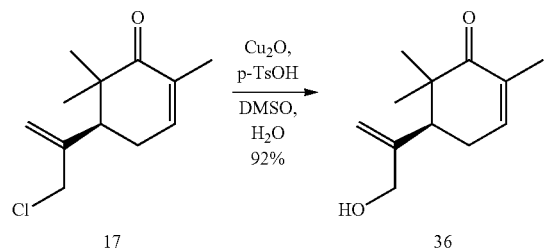

Under a nitrogen atmosphere, Cu$_2$O (1.43 g, 10.0 mmol) and p-TsOH (1.46 g, 8.47 mmol) were added to a solution of Compound (17) (1.53 g, 7.70 mmol) in DMSO/H$_2$O (1:2, 12 ml), and the mixture was agitated at room temperature for 2 hours. A 1% H$_3$PO$_4$ solution and EtOAc were added, the mixture was agitated for 30 minutes to terminate the reaction, the reaction product was filtered through Celite, and the resultant was then subjected to extraction with EtOAc. The combined organic phases were dried over Na$_2$SO$_4$ and then concentrated. The resulting crude product was purified via column chromatography (silica gel: 32.9 g; hexane:EtOAc=5:1), and Compound (36) was obtained as a yellow oil product (1.28 g, 92%).

$^1$H-NMR (400 MHz, CDCl$_3$) δ 6.62 (m, 1H, C[H]=CCH$_3$), 5.27 (s, 1H, ½C[H$_2$]=C), 5.00 (s, 1H, ½C[H$_2$]=C), 4.05 (m, 2H, C[H$_2$]OH), 2.53 (m, 1H, C[H]C(CH$_3$)$_2$), 2.44 (m, 2H, C[H$_2$]CH), 1.79 (m, 3H, C[H$_3$]C=CH), 1.11 (s, 3H, C[H$_3$]CCH$_3$), 1.04 (s, 3H, C[H$_3$]CCH$_3$);
HRMS (EI) [M]$^+$ calcd for C$_{12}$H$_{18}$O$_2$: 194.1307; found: 194.1306.

3) Synthesis of (R)-5-((S)-2-(hydroxymethyl)oxiran-2-yl)-2,6,6-trimethylcyclohex-2-enone (37)

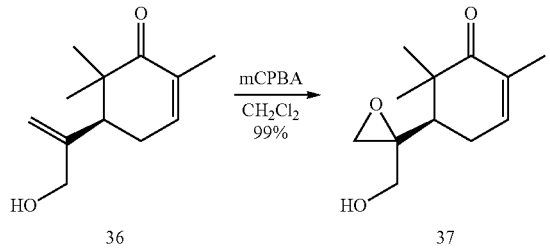

Under a nitrogen atmosphere at 0° C., mCPBA (m-chloroperbenzoic acid) (2.95 g, 11.1 mmol) was added to 111 ml of a solution of Compound (36) (2.00 g, 11.1 mmol) in CH$_2$Cl$_2$, and the mixture was agitated at room temperature for 2 hours and 40 minutes. The reaction was terminated with the addition of a saturated Na$_2$S$_2$O$_3$ aqueous solution at 0° C., a saturated NaHCO$_3$ aqueous solution was added thereto, and the reaction product was subjected to extraction with CH$_2$Cl$_2$. The combined organic phases were dried over Na$_2$SO$_4$ and then concentrated. The resulting crude product was purified via column chromatography (silica gel: 43.0 g; hexane:EtOAc=3:1), and Compound (37) was obtained as a diastereomer mixture in the form of a yellow oil product (2.16 g, 99%).

$^1$H-NMR (300 MHz, CDCl$_3$) δ 6.60 (m, 1H, C[H]=CCH$_3$), 3.60 (m, 2H, C[H$_2$]OH), 3.12 (d, 1H, J=4.5 Hz, ½C[H$_2$]OC), 2.70 (m, 1H, ½C[H$_2$]C), 2.66 (d, 1H, J=4.8 Hz, ½C[H$_2$]OC), 2.50 (m, 1H, ½C[H$_2$]CH), 1.78 (s, 3H, C[H$_2$]C=CH), 1.75 (t, 1H, J=5.1 Hz, C[H]C(CH$_3$)$_2$), 1.21 (s, 3H, C[H$_3$]CCH$_3$), 1.17 (s, 3H, C[H$_3$]CCH$_3$);

HRMS (EI) [M]$^+$ calcd for C$_{12}$H$_{3}$O$_3$: 210.1256; found: 210.1253.

4) Synthesis of (R)-5-((R)-2-(((tert-butyldimethylsilyl)oxy)methyl)oxiran-2-yl)-2,6,6-trimethylcyclohex-2-enone (18)

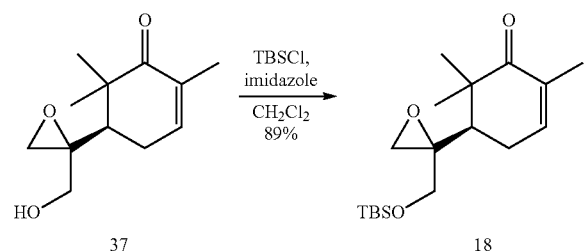 [SMILES: CC1=CC[C@@H](C2(CO)CO2)C(C)(C)C1=O ; CC1=CC[C@@H](C2(CO[Si](C)(C)C(C)(C)C)CO2)C(C)(C)C1=O]

Under a nitrogen atmosphere, imidazole (529 mg, 7.77 mmol) and TBSCl (586 mg, 3.89 mmol) were added to 26 ml of a solution of Compound (37) (509 mg, 2.59 mmol) in CH$_2$Cl$_2$, and the mixture was agitated at room temperature for 30 minutes. The reaction was terminated with the addition of H$_2$O, EtOAc was added thereto, and the organic phase was washed with water. The organic phase was dried over Na$_2$SO$_4$ and then concentrated. The resulting crude product was purified via column chromatography (silica gel: 10.9 g; hexane:EtOAc=50:1), and Compound (18) was obtained as a diastereomer mixture in the form of a colorless oil product (750 mg, 89%).

$^1$H-NMR (300 MHz, CDCl$_3$) δ 6.58 (t, 1H, J=2.4 Hz, C[H]=CCH$_3$), 3.60 (m, 2H, C[H$_2$]OTBS), 2.94 (d, 1H, J=5.4 Hz, ½C[H$_2$]OC), 2.61 (m, 1H, ½C[H$_2$]CH), 2.61 (d, 1H, J=2.7 Hz, ½C[H$_2$]OC), 2.44 (m, 1H, ½C[H$_2$]CH), 1.93 (dd, 1H, J=5.1, 6.0 Hz, C[H]C(CH$_3$)$_2$), 1.76 (s, 3H, C[H$_3$]C=CH), 1.21 (s, 3H, C[H$_3$]CCH$_3$), 1.19 (s, 3H, C[H$_3$]CCH$_3$), 0.86 (m, 9H, (C[H$_3$])$_3$CSi), 0.01 (m, 6H, (C[H$_3$])$_2$Si);

HRMS (ESI, TFANa) [M+Na]$^+$ calcd for C$_{18}$H$_{32}$NaO$_3$Si: 347.2018; found: 347.2021.

5) Synthesis of (S)-5-((S)-1-((tert-butyldimethylsilyl)oxy)-3-hydroxypropan-2-yl)-2,6,6-trimethylcyclohex-2-enone (19)

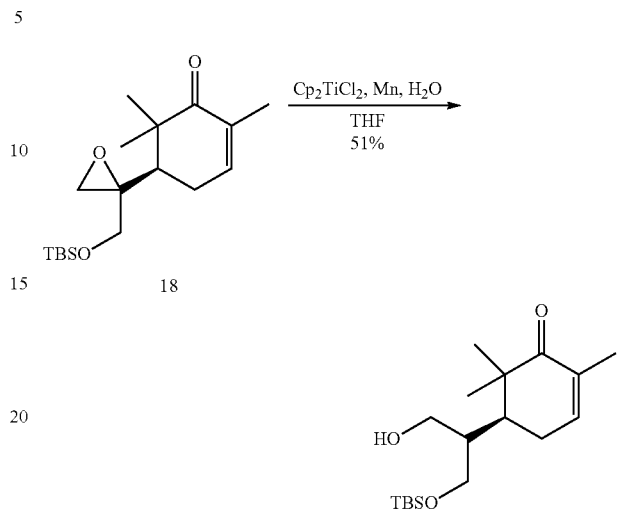

Under an argon atmosphere, 20 ml of a solution of Cp$_2$TiCl$_2$ (1.26 g, 5.08 mmol) and Mn (1.02 g, 18.5 mmol) in THF was agitated at room temperature for 15 minutes, 3.0 ml of a solution of Compound (18) (750 mg, 2.31 mmol) and H$_2$O (1.66 ml, 92.4 mmol) in THF was added dropwise thereto, and the mixture was agitated for 12 hours. The reaction was terminated with the addition of a NaH$_2$PO$_4$ solution, the reaction product was filtered through Celite, and the reaction product was subjected to extraction with EtOAc. The combined organic phases were dried over Na$_2$SO$_4$ and then concentrated. The resulting crude product was purified via column chromatography (silica gel: 16.1 g; hexane:EtOAc=10:1), Compound (19) was obtained as a diastereomer mixture in the form of a colorless oil product (382 mg, 51%), and Compound (18) remaining unreacted was recovered (276 mg, 37%).

$^1$H-NMR (300 MHz, CDCl$_3$) δ 6.61 (dd, 1H, J=1.2, 2.4 Hz, C[H]=CCH$_3$), 3.71 (m, 2H, C[H$_2$]OTBS), 3.71 (m, 2H, C[H$_2$]OH), 2.31 (m, 2H, C[H$_2$]CH=C), 2.03 (m, 1H, C[H]CH$_2$OH), 1.82 (m, 1H, C[H]C(CH$_3$)$_2$), 1.75 (s, 3H, C[H$_3$]C=CH) 1.20 (s, 3H, C[H$_3$]CCH$_3$), 1.07 (s, 3H, C[H$_3$]CCH$_3$), 0.89 (m, 9H, (C[H$_3$])$_3$CSi), 0.07 (m, 6H, (C[H$_3$])$_2$Si);

HRMS (ESI, TFANa) [M+Na]$^+$ calcd for C$_{18}$H$_{34}$NaO$_3$Si: 349.2175; found: 349.2168.

6) Synthesis of (S)-2,6,6-trimethyl-5-(2,2,3,3,9,9,10,10-octamethyl-4,8-dioxa-3,9-disilaundecan-6-yl)cyclohex-2-enone (20)

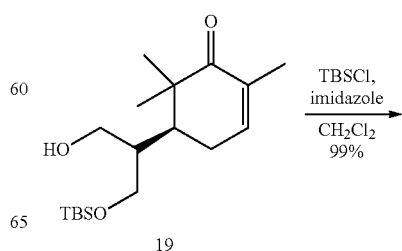

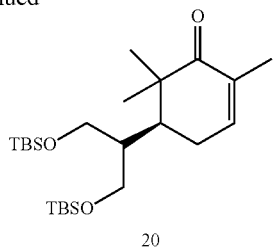

20

Under a nitrogen atmosphere, imidazole (233 mg, 3.43 mmol) and TBSCl (258 mg, 1.71 mmol) were added to 11 ml of a solution of Compound (19) (373 mg, 1.14 mmol) in CH$_2$Cl$_2$, and the mixture was agitated at room temperature for 30 minutes. The reaction was terminated with the addition of H$_2$O, EtOAc was added thereto, and the organic phase was washed with water. The organic phase was dried over Na$_2$SO$_4$ and then concentrated. The resulting crude product was purified via column chromatography (silica gel: 8.03 g; hexane:EtOAc=200:1), and Compound (20) was obtained as a colorless oil product (498 mg, 99%).

$^1$H-NMR (400 MHz, CDCl$_3$) δ 6.59 (dd, 1H, J=0.9, 1.8 Hz, C[H]=CCH$_3$), 3.55 (m, 4H, 2×C[H$_2$]OTBS), 2.35 (m, 2H, C[H$_2$]CH=C), 2.06 (m, 1H, C[H](CH$_2$OTBS)$_2$), 1.85 (m, 1H, C[H]C(CH$_3$)$_2$), 1.72 (s, 3H, C[H$_3$]C=CH) 1.16 (s, 3H, C[H$_3$]CCH$_3$), 1.02 (s, 3H, C[H$_3$]CCH$_3$), 0.86 (m, 18H, 2×(C[H$_3$])$_3$CSi), 0.01 (m, 12H, 2×(C[H$_3$])$_2$Si);

HRMS (ESI, TFANa) [M+Na]$^+$ calcd for C$_{24}$H$_{48}$NaO$_3$Si$_2$: 463.3040; found: 463.3061.

7) Synthesis of (1S,4S,6S)-1,3,3-trimethyl-4-(2,2,3,3,9,9,10,10-octamethyl-4,8-dioxa-3,9-disilaundecan-6-yl)-7-oxabicyclo[4.1.0]heptan-2-one (21)

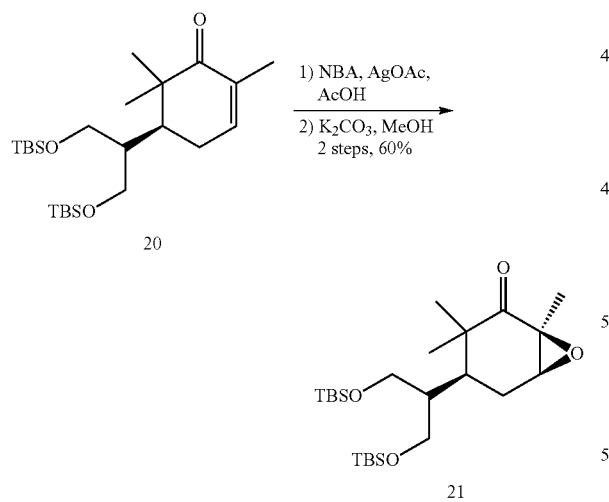

NBA (3-nitrobenzyl alcohol) (468 mg, 3.39 mmol) and AgOAc (566 mg, 3.39 mmol) were added to 11 ml of a solution of Compound (20) (498 mg, 1.13 mmol) in AcOH, and the mixture was agitated at room temperature for 2 hours. The resultant was filtered through Celite, the reaction was terminated with the addition of a saturated NaHCO$_3$ aqueous solution, and the reaction product was then subjected to extraction with CH$_2$Cl$_2$. The combined organic phases were dried over Na$_2$SO$_4$ and then concentrated. The resulting crude product was roughly purified via column chromatography (silica gel: 10.7 g; hexane:EtOAc=100:1), and a fraction containing a product was concentrated to obtain a crude product.

To 2.5 ml of a solution of the resulting crude product in MeOH, K$_2$CO$_3$ (309 mg, 2.23 mmol) was added, and the mixture was agitated at room temperature for 15 minutes. The reaction was terminated with the addition of H$_2$O, EtOAc was added thereto, and the organic phase was washed with water. The organic phase was dried over Na$_2$SO$_4$ and then concentrated. The resulting crude product was purified via column chromatography (silica gel: 9.05 g; hexane:EtOAc=200:1), and Compound (21) was obtained as a white solid material (312 mg, 2-step process, 60%).

$^1$H-NMR (400 MHz, CDCl$_3$) δ 3.60 (m, 4H, 2×C[H$_2$]OTBS), 3.38 (ddd, 1H, J=1.2, 1.5, 3.0 Hz, C[H](O)C), 2.17 (m, 2H, C[H$_2$]CHO), 1.89 (m, 1H, C[H](CH$_2$OTBS)$_2$), 1.74 (m, 1H, C[H]C(CH$_3$)$_2$), 1.38 (s, 3H, C[H$_3$]COCH) 1.17 (s, 3H, C[H$_3$]CCH$_3$), 1.11 (s, 3H, C[H$_3$]CCH$_3$), 0.88 (m, 18H, 2×(C[H$_3$])$_3$CSi), 0.04 (m, 12H, 2×(C[H$_3$])$_2$Si);

HRMS (ESI, TFANa) [M+Na]$^+$ calcd for C$_{24}$H$_{48}$NaO$_4$Si$_2$: 479.2989; found: 479.2967.

8) Synthesis of 5-((3S,5S)-3-((tert-butyldimethylsilyl)oxy)-2,6,6-trimethyl-5-(2,2,3,3,9,9,10,10-octamethyl-4,8-dioxa-3,9-disilaundecan-6-yl)cyclohex-1-enecarbonyl)-2,2,6-trimethyl-4H-1,3-dioxin-4-one (23)

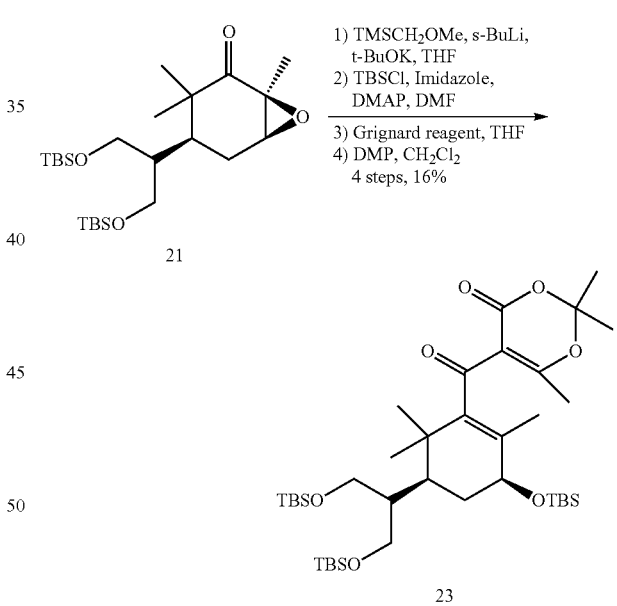

Under an argon atmosphere, s-BuLi (a 1 M THF solution, 0.644 ml, 0.657 mmol) was added dropwise to 1.2 ml of a solution of TMSCH$_2$OMe (0.102 ml, 0.657 mmol) in THF at −23° C., and the mixture was agitated at room temperature for 30 minutes. Thereafter, 1.0 ml of a solution of Compound (21) (100 mg, 0.219 mmol) in THF was added dropwise to the solution obtained above at −78° C., and the mixture was agitated at −60° C. for 20 minutes. Thereafter, t-BuOK (98.3 mg, 0.876 mmol) was added thereto, the temperature was gradually raised to room temperature, and the mixture was agitated at room temperature for 1 hour. A saturated NH$_4$Cl aqueous solution was added, the reaction was terminated by agitating the mixture for 15 minutes, EtOAc was added thereto, the resultant was washed with a 2 N HCl solution, and the organic phase was dried over Na$_2$SO$_4$, followed by concentration.

Imidazole (59.9 mg, 0.880 mmol), a catalytic amount of DMAP, and TBSCl (99.5 mg, 0.660 mmol) were added to 2.2 ml of a solution of the residue obtained above in DMF. Under a nitrogen atmosphere, the mixture was agitated at 50° C. for 1 hour. The reaction was terminated with the addition of H$_2$O, EtOAc was added thereto, and the organic phase was washed with water. The organic phase was dried over Na$_2$SO$_4$ and then concentrated. The resulting crude product was roughly purified via column chromatography (silica gel: 2.22 g; hexane:EtOAc=200:1), and a fraction containing the product was concentrated to obtain a crude product.

Under an argon atmosphere at −30° C., iPrMgCl (a 2.0 M THF solution, 0.221 ml, 0.441 mmol) was added dropwise to 0.7 ml of a solution of 5-iodo-2,2,6-trimethyl-4H-1,3-dioxin-4-one (118 mg, 0.441 mmol) in THF, and the mixture was agitated for 1 hour. Thereafter, 0.7 ml of a solution of the crude product in THF was added dropwise to the solution, and the mixture was agitated at room temperature for 15 minutes. The reaction was terminated with the addition of a saturated NH$_4$Cl aqueous solution, and the reaction product was subjected to extraction with EtOAc. The combined organic phases were dried over Na$_2$SO$_4$ and then concentrated.

Under a nitrogen atmosphere at 0° C., DMP (93.5 mg, 0.221 mmol) was added to 1.5 ml of a solution of the residue obtained above in CH$_2$Cl$_2$, and the mixture was agitated for 15 minutes. The reaction was terminated with the addition of a saturated Na$_2$S$_2$O$_3$ aqueous solution and a saturated NaHCO$_3$ aqueous solution, EtOAc was added thereto, and the organic phase was washed with a saturated NaHCO$_3$ aqueous solution. The organic phase was dried over Na$_2$SO$_4$ and then concentrated. The resulting crude product was purified via column chromatography (silica gel: 1.84 g; hexane:EtOAc=30:1), and Compound (23) was obtained as a yellow oil product (25.4 mg, 4-step process, 16%).

$^1$H-NMR (400 MHz, CDCl$_3$) δ 4.12 (ddd, 1H, J=2.7, 6.0, 6.6 Hz, C[H]OTBS), 3.61 (m, 4H, 2×C[H$_2$]OTBS), 2.44 (s, 3H, C[H$_3$]COC(CH$_3$)$_2$), 1.92 (m, 2H, C[H$_2$]CHOTBS), 1.75 (m, 1H, C[H]C(CH)$_2$), 1.70 (s, 3H, C[H$_3$]COC=O), 1.69 (s, 3H, C[H$_3$]COC=O), 1.62 (m, 1H, C[H](CH$_2$OTBS)$_2$), 1.52 (d, 3H, J=9.2 Hz, C[H$_3$]CCHOTBS) 1.15 (s, 3H, C[H$_3$]C(CH$_3$)C), 0.97 (s, 3H, C[H$_3$]C(CH$_3$)C), 0.89 (m, 27H, 3×(C[H$_3$])$_3$CSi), 0.04 (m, 18H, 3×(C[H$_3$])$_2$Si);

HRMS (ESI, TFANa) [M+Na]$^+$ calcd for C$_{38}$H$_{72}$NaO$_7$Si$_3$: 747.4484; found: 747.4481.

9) Synthesis of (4aR,6S,8S,8aS)-methyl 8-((tert-butyldimethylsilyl)oxy)-2,5,5,8a-tetramethyl-6-(2,2,3,3,9,9,10,10-octamethyl-4,8-dioxa-3,9-disilaundecan-6-yl)-4-oxo-4a,5,6,7,8,8a-hexahydro-4H-chromene-3-carboxylate (24)

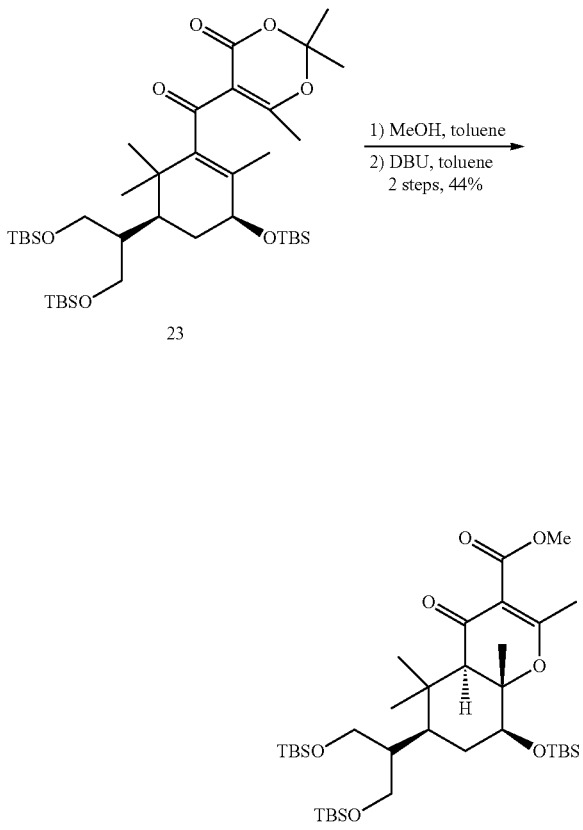

A solution of Compound (23) (70 mg, 0.097 mmol) in toluene (0.8 ml) and MeOH (0.2 ml) was agitated at 90° C. for 3 hours and 15 minutes and then concentrated.

DBU (0.015 ml, 0.097 mmol) was added to 1.0 ml of a solution of the residue obtained above in toluene, and the mixture was agitated at 100° C. for 4 hours. The reaction was terminated with the addition of H$_2$O, EtOAc was added thereto, and the organic phase was washed with water. The organic phase was dried over Na$_2$SO$_4$ and then concentrated. The resulting crude product was purified via column chromatography (silica gel: 1.46 g; hexane:EtOAc=50:1), and Compound (24) was obtained as a yellow oil product (29.8 mg, 44%).

$^1$H-NMR (300 MHz, CDCl$_3$) δ 3.79 (ddd, 4H, J=4.5, 4.8, 6.6 Hz, 2×C[H$_2$]OTBS), 3.60 (m, 3H, C[H$_3$]O), 3.45 (dd, 1H, J=8.4, 9.9 Hz, C[H]OTBS), 2.43 (s, 1H, C[H]C=O), 2.14 (s, 3H, C[H$_3$]C=C), 1.82 (d, 1H, J=3.0 Hz, ½C[H$_2$]CHOTBS), 1.69 (m, 1H, (C[H](CH$_2$OTBS)$_2$), 1.50 (d, 1H, J=13.5 Hz, ½C[H$_2$]CHOTBS), 1.37 (d, 1H, J=11.4 Hz, C[H]C(CH$_3$)$_2$), 1.32 (s, 3H, C[H$_3$]CCHOTBS) 1.06 (s, 3H, C[H$_3$]CCH$_3$), 0.92 (s, 3H, C[H$_3$]CCH$_3$), 0.88 (m, 27H, 3×(C[H$_3$])$_3$CSi), 0.04 (m, 18H, 3×(C[H$_3$])$_2$Si);

HRMS (ESI, TFANa) [M+Na]$^+$ calcd for C$_{36}$H$_{70}$NaO$_7$Si$_3$: 721.4327; found: 721.4349.

10) Synthesis of (5aS,6S,8S,9aR)-6-((tert-butyldimethylsilyl)oxy)-5a,9,9-trimethyl-8-(2,2,3,3,9,9,10,10-octamethyl-4,8-dioxa-3,9-disilaundecan-6-yl)-3-(pyridin-2-yl)-5a,6,7,8,9,9a-hexahydropyrano[4,3-b]chromene-1,10-dione (25)

1) Synthesis of 2-((5aS,6S,8S,9aS,10R)-6-acetoxy-10-hydroxy-5a,9,9-trimethyl-1-oxo-3-(pyridin-2-yl)-1,5a,6,7,8,9,9a,10-octahydropyrano[4,3-b]chromen-8-yl)propane-1,3-diyl diacetate (26) (PT010)

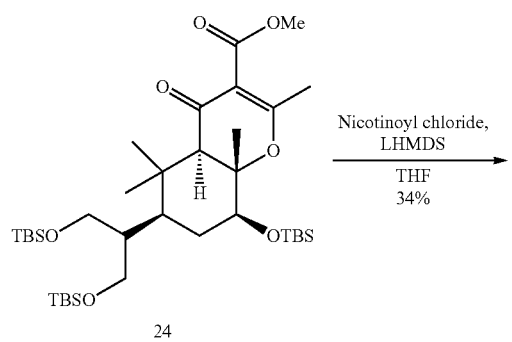

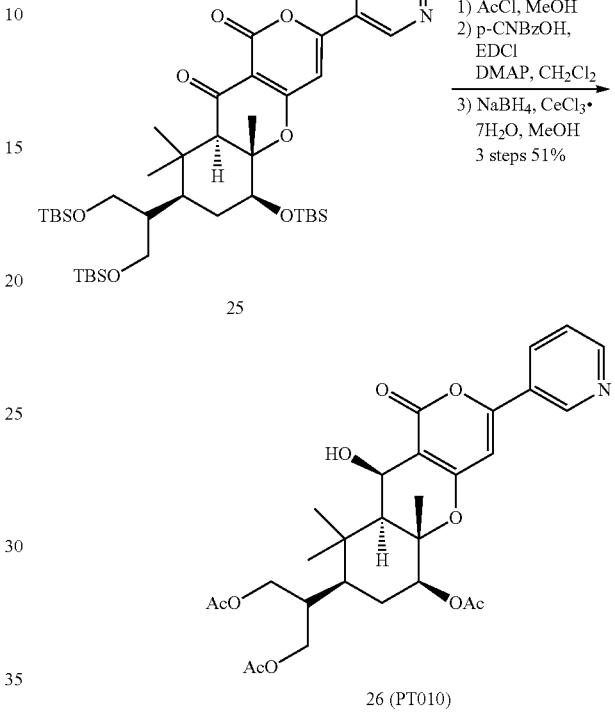

Under an argon atmosphere, 0.2 ml of a solution of Compound (24) (30.0 mg, 0.0429 mmol) in THF was added dropwise to 0.2 ml of a solution of LHMDS (a 1.0 M THF solution, 0.215 ml, 0.215 mmol) in THF at −78° C., the mixture was agitated at room temperature for 4 hours, nicotinoyl chloride hydrochloride (22.9 mg, 0.129 mmol) was added thereto at −78° C., the mixture was agitated at 0° C. for 15 minutes, and the mixture was agitated at room temperature for an additional 2 hours. The reaction was terminated with the addition of AcOH, EtOAc was added thereto, and the organic phase was washed with water. The organic phase was dried over $Na_2SO_4$ and then concentrated. The resulting crude product was purified via column chromatography (silica gel: 0.645 g; hexane:EtOAc=5:1), and Compound (25) was obtained as a yellow oil product (11.3 mg, 34%).

$^1$H-NMR (300 MHz, $CDCl_3$) 9.05 (s, 1H, Py), 8.76 (s, 1H, Py), 8.22 (d, 1H, J=8.1 Hz, Py), 7.50 (m, 1H, Py), 6.39 (s, 1H, C[H]=C), 3.79 (ddd, 4H, J=5.1, 5.7, 8.7 Hz, 2×C[$H_2$]OTBS), 3.50 (m, 1H, C[$H_1$]OTBS), 2.60 (s, 1H, C[H]C=O), 1.84 (m, 1H, ½C[$H_2$]CHOTBS), 1.71 (m, 1H, C[H]($CH_2$OTBS)$_2$), 1.56 (m, 1H, ½C[$H_2$]CHOTBS), 1.42 (m, 1H, C[H]C($CH_3$)$_2$), 1.44 (s, 3H, C[$H_3$]CCHOTBS) 1.15 (s, 3H, C[$H_3$]CCH$_3$), 0.97 (s, 3H, C[$H_3$]CCH$_3$), 0.91 (m, 27H, 3×(C[$H_3$])$_3$CSi), 0.04 (m, 18H, 3×(C[$H_3$])$_2$Si);

HRMS (ESI, TFANa) [M+]$^+$ calcd for $C_{41}H_6NO_7Si_3$: 772.4460; found: 772.4446.

AcCl (0.0207 ml, 0.292 mmol) was added to 0.5 ml of a solution of Compound (25) (11.3 mg, 0.0146 mmol) in MeOH at 0° C., and the mixture was agitated for 1 hour, followed by concentration.

Under a nitrogen atmosphere at 0° C., $Et_3N$ (0.033 ml, 0.234 mmol), a catalytic amount of DMAP, and $Ac_2O$ (0.011 ml, 0.117 mmol) were added to 0.5 ml of a solution of the residue obtained above in $CH_3CN$, and the mixture was agitated at room temperature for 15 minutes. The reaction was terminated with the addition of MeOH and water, and the reaction product was subjected to extraction with $CH_2Cl_2$. Thereafter, the combined organic phases were dried over $Na_2SO_4$ and then concentrated.

$CeCl_3 \cdot 7H_2O$ (21.8 mg, 0.0584 mmol) and $NaBH_4$ (2.2 mg, 0.0584 mmol) were added to 0.5 ml of a solution of the residue obtained above in MeOH at 0° C., and the mixture was agitated for 30 minutes. The reaction was terminated with the addition of acetone, water was added thereto, and the organic phase was then extracted with $CH_2Cl_2$. The organic phase was dried over $Na_2SO_4$ and then concentrated. The resulting crude product was purified via preparative TLC (hexane:EtOAc=1:2), and Compound (26) (PT010) was obtained as a white solid material (4.2 mg, 3-step process, 51%).

$^1$H-NMR (400 MHz, $CDCl_3$) δ 9.04 (s, 1H, Py), 8.71 (s, 1H, Py), 8.20 (m, 1H, Py), 7.50 (m, 1H, Py), 6.50 (d, 1H, J=4.8 Hz, C[H]=C), 5.05 (d, 1H, J=4.0 Hz, C[H]OH), 4.94 (m, 1H, C[H]OAc), 4.19 (m, 2H, C[$H_2$]OAc), 3.97 (m, 2H, C[$H_2$]OAc), 2.29 (m, 1H, C[H]($CH_2$OAc)$_2$), 2.16 (m, 3H,

C[H₃]C=O), 2.12 (m, 2H, C[H₂]CHOAc), 2.08 (m, 1H, C[H]C(CH₃)₂), 2.08 (m, 6H, 2×C[H₃]C=O), 1.97 (m, 1H, C[H]CHOH), 1.58 (s, 3H, C[H₃]CO) 1.34 (s, 3H, C[H₃]CCH₃), 1.25 (s, 3H, C[H₃]CCH₃);

HRMS (ESI, TFANa) [M+Na]⁺ calcd for $C_2H_{35}NNaO_{10}$: 580.2159; found: 80.2137.

Example 111

Production of (5aS,6S,8S,9aS,10R)-10-hydroxy-5a,9,9-trimethyl-1-oxo-3-(pyridin-3-yl)-8-(2-(o-toluyl)-1,3-dioxan-5-yl)-1,5a,6,7,8,9,9a,10-octahydropyrano[4,3-b]chromen-6-yl 4-cyanobenzoate (PT017)

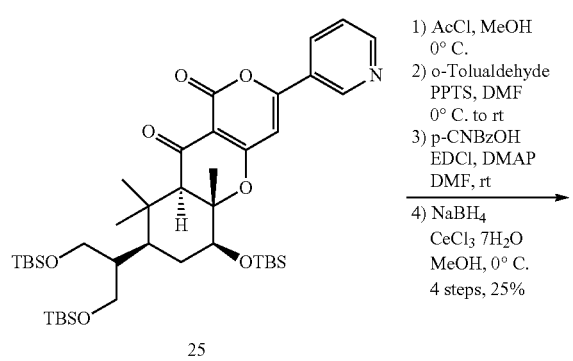

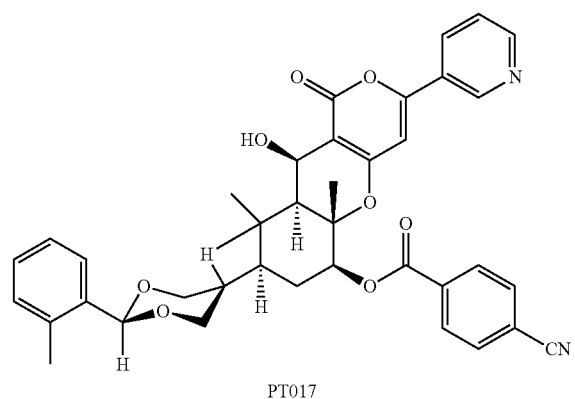

PT017

AcCl (61 μl, 0.860 mmol) was added to 0.5 ml of a solution of Compound 25 (33.2 mg, 0.043 mmol) in MeOH at 0° C., and the mixture was agitated for 1 hour, followed by concentration. Under a nitrogen atmosphere at 0° C., o-tolualdehyde (25 μl, 0.215 mmol) and a catalytic amount of PPTS were added to 0.5 ml of a solution of the residue obtained above in DMF, and the mixture was agitated at room temperature for 2 hours. The reaction was terminated with the addition of water, EtOAc was added thereto, and the organic phase was washed with water. Thereafter, the combined organic phases were dried over Na₂SO₄ and then concentrated. Under a nitrogen atmosphere at room temperature, EDCl (6.9 mg, 0.0359 mmol), a catalytic amount of DMAP, and p-CNBzOH (4.4 mg, 0.0300 mmol) were added to 0.5 ml of a solution of the residue obtained above in DMF, and the mixture was agitated at room temperature for 14 hours and 30 minutes. The reaction was terminated with the addition of H₂O, EtOAc was added thereto, and the organic phase was washed with 0.1 N HCl and a saturated NaHCO₃ aqueous solution. The organic phase obtained was dried over Na₂SO₄ and then concentrated. CeCl₃.7H₂O (9.7 mg, 0.0259 mmol) and NaBH₄ (1.0 mg, 0.0259 mmol) were added to 0.5 ml of a solution of the residue obtained above in MeOH at 0° C., and the mixture was agitated for 30 minutes. The reaction was terminated with the addition of acetone, and the reaction product was subjected to extraction with CH₂Cl₂. The combined organic phases were dried over Na₂SO₄ and then concentrated. The resulting crude product was purified via preparative TLC (20:1 CH₂Cl₂/MeOH), and a white solid material, PT017, was obtained (7.0 mg, 4-step process, 25%).

$[\alpha]^{27}_D$ –105.6 (c, 0.1, CHCl₃); IR (KBr) 3448, 2360, 2341, 1643, 1277, 1086 cm⁻¹; ¹H-NMR (400 MHz, CDCl₃) δ 8.97 (bs, 1H, Py), 8.67 (bs, 1H, Py), 8.19 (d, 2H, p-CN[Bz], J=8.0 Hz), 8.06 (d, 1H, Py, J=8.0 Hz), 7.80 (d, 2H, p-CN[Bz], J=8.8 Hz), 7.38 (dd, 1H, Py, J=4.8, 8.0 Hz), 6.39 (s, 1H, C[H]=C), 5.21 (dd, 1H, C[H]Op-CNBz, J=4.4, 11.2 Hz), 5.08 (d, 1H, C[H](OH)CH, J=4.0 Hz), 4.23-4.18 (m, 2H, C[H₂]OAc), 4.02 (dd, 1H, ½C[H₂]OAc, J=6.4, 11.2 Hz), 3.93 (dd, 1H, ½C[H₂]OAc, J=10.0, 11.2 Hz), 2.98 (bs, 1H, OH), 2.35-2.31 (m, 1H, C[H](CH₂OAc)), 2.15-2.10 (m, 1H, ½C[H₂]CHOp-CNBz), 2.10 (s, 3H, Ac), 2.06 (s, 3H, Ac), 1.82 (s, 3H, C[H₃]CCHOp-CNBz), 1.77-1.65 (m, 3H, ½C[H₂]CHOp-CNBz, C[H]CH(OH), C[H]C(CH₃)₂) 1.39 (s, 3H, C[H₃]CCH₃), 1.27 (s, 3H, C[H₃]CCH₃);

¹³C-NMR (100 MHz, CDCl₃) 5171.1, 171.0, 164.0, 163.8, 161.8, 157.4, 151.5, 146.7, 133.9, 133.1, 132.4, 130.2, 117.9, 116.8, 103.2, 99.1, 82.8, 78.9, 65.6, 62.4, 60.5, 52.5, 46.1, 39.1, 34.9, 27.1, 26.7, 20.9, 18.5, 15.9;

ESI-HRMS (TFA-Na) calcd for $C_{35}H_{36}N_2NaO_{10}$: 666.2268 (M+Na⁺); found: 666.2293 (M+Na⁺).

Example 12

Production of 2-((5aS,6S,8S,9aS,10R)-6-((4-cyanobenzoyl)oxy)-10-hydroxy-5a,9,9-trimethyl-1-oxo-3-(pyridin-3-yl)-1,5a,6,7,8,9,9a,10-octahydropyrano[4,3-b]chromen-8-yl)propane-1,3-diyl diacetate (PT022)

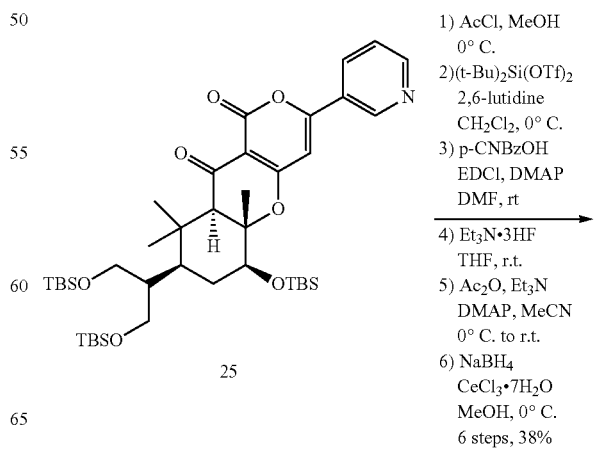

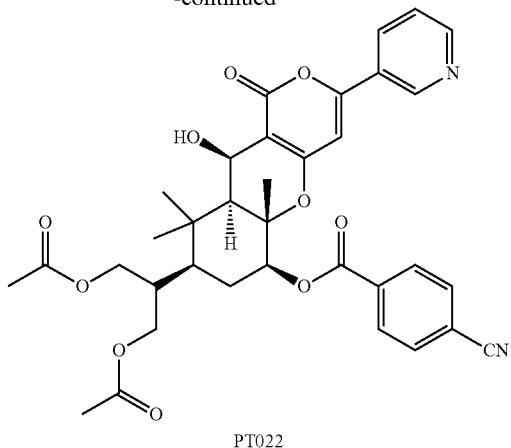

PT022

AcCl (105 µl, 1.473 mmol) was added to 1.0 ml of a solution of Compound 25 (56.8 mg, 0.0737 mmol) in MeOH at 0° C., and the mixture was agitated for 1 hour, followed by concentration. Under a nitrogen atmosphere at 0° C., 2,6-lutidine (26 µl, 0.221 mmol) and (t-Bu)$_2$Si(OTf)$_2$ (30 µl, 0.0811 mmol) were added to 2.0 ml of a solution of the residue obtained above in DMF, and the mixture was agitated for 1 hour. The reaction was terminated with the addition of MeOH, EtOAc was added thereto, and the organic phase was washed with water. Thereafter, the combined organic phases were dried over Na$_2$SO$_4$ and then concentrated. Under a nitrogen atmosphere at room temperature, EDCl (56.5 mg, 0.295 mmol), a catalytic amount of DMAP, and p-CNBzOH (32.5 mg, 0.221 mmol) were added to a solution of the residue obtained above in CH$_2$Cl$_2$ (1.0 ml), and the mixture was agitated at room temperature for 1 hour. The reaction was terminated with the addition of MeOH, EtOAc was added thereto, and the organic phase was washed with 0.1 N HCl and a saturated NaHCO$_3$ aqueous solution. The resulting organic phase was dried over Na$_2$SO$_4$ and then concentrated. Et$_3$N.3HF (12 µl, 0.0737 mmol) was added to 1.0 ml of a solution of the residue obtained above in THF, and the mixture was agitated for 1 hour, followed by concentration. The remaining material was roughly purified via preparative TLC (10:1 CH$_2$Cl$_2$/MeOH) to obtain a crude product. Under a nitrogen atmosphere, Et$_3$N (82 µl, 0.590 mmol), a catalytic amount of DMAP, and Ac$_2$O (30 µl, 0.295 mmol) were added to 1.0 ml of a solution of the resulting crude product in MeCN at room temperature, and the mixture was agitated at room temperature for 0.5 hours. The reaction was terminated with the addition of MeOH, EtOAc was added thereto, and the organic phase was washed with water. The resulting organic phase was dried over Na$_2$SO$_4$ and then concentrated. CeCl$_3$.7H$_2$O (54.9 mg, 0.147 mmol) and NaBH$_4$ (5.6 mg, 0.147 mmol) were added to 1.0 ml of a solution of the residue obtained in MeOH at 0° C., and the mixture was agitated for 15 minutes. The reaction was terminated with the addition of acetone, and the reaction product was subjected to extraction with CH$_2$Cl$_2$. The combined organic phases were dried over Na$_2$SO$_4$ and then concentrated. The resulting crude product was purified via preparative TLC (1:2 hexane/EtOAc), and a white solid material, PT022, was obtained (18.1 mg, 6-step process, 38%).

$^1$H-NMR (400 MHz, CD$_3$OD) δ9.08 (bs, 1H, Py), 8.69 (s, 1H, Py), 8.31 (d, 1H, Py, J=8.0 Hz), 8.23 (d, 2H, p-CN[Bz], J=8.0 Hz), 7.90 (d, 2H, p-CN[Bz], J=8.8 Hz), 7.58 (bs, 1H, Py), 7.48 (dd, 1H, Ph, J=1.6, 7.6 Hz), 7.19-7.08 (m, 3H, Ph), 6.77 (s, 1H, C[H]=C), 5.55 (s, 1H, PhC[H]OCH$_2$), 5.22 (dd, 1H, C[H]Op-CNBz, J=4.8, 12.0 Hz), 5.04 (d, 1H, C[H](OH)CH, J=3.6 Hz), 4.27-4.23 (m, 1H, ½C[H$_2$] OCHPh), 4.00-3.96 (m, 1H, ½C[H$_2$]OCHPh), 3.81 (dd, 1H, ½C[H$_2$]OCHPh, J=11.2, 18.8 Hz), 3.78 (dd, 1H, ½C[H$_2$]OCHPh, J=11.2, 18.8 Hz), 2.42-2.32 (m, 1H, C[H]C$_2$OCHPh), 2.31 (s, 3H, C[H$_3$]Ph), 2.12-2.06 (m, 1H, ½C[H$_2$]CHOp-CNBz), 1.86 (s, 3H, C[H$_3$]CCHOp-CNBz), 1.80 (dd, 1H, ½C[H$_2$]CHOp-CNBz, J=13.2, 25.6 Hz), 1.71 (d, 1H, C[H]CH(OH), J=3.6 Hz), 1.40 (s, 3H, C[H$_3$]CCH$_3$), 1.32 (s, 3H, C[H$_3$]CCH$_3$), 1.27-1.22 (m, 1H, C[H]C(CH$_3$)$_2$);

$^{13}$C-NMR (100 MHz, CDCl$_3$) δ164.3, 163.6, 161.7, 135.9, 135.7, 133.9, 132.6, 130.5, 130.4, 129.0, 126.1, 125.7, 117.9, 117.0, 103.8, 100.0, 82.9, 79.0, 72.0, 70.7, 60.5, 52.6, 45.7, 39.4, 32.8, 32.0, 29.8, 29.7, 29.5, 27.3, 27.2, 22.8, 19.0, 18.8, 16.0, 14.2;

ESI-HRMS (TFA-Na) calcd for C$_{39}$H$_{39}$N$_2$O$_8$: 663.2706 (MH$^+$); found: 663.2713 (MH$^+$).

II. Pharmacological Test of Novel Compound

Test Example 1: Test of Inhibitory Activity Against ACAT2

The compounds produced in accordance with the procedure described above were tested concerning the inhibitory activity against ACAT2 in the manner described below.

[Method for Preparation of ACAT2 Enzyme Protein]

The ACAT2 enzyme protein was prepared in accordance with the method of Uelmen et al. (Uelmen et al., J. Biol. Chem., Vol. 270, pp. 26192-26210, 1995), which was partly modified. The ACAT2 enzyme protein was extracted from the membrane fraction derived from the murine hepatic microsome. Mouse livers were homogenized in buffer A (50 mM Tris-HCl buffer (pH 7.8), 1 mM ethylenediaminetetraacetic acid, and 1 mM phenylmethanesulfonyl fluoride) using a Potter-type homogenizer (Tokyo-RIKO). The homogenate was centrifuged at 12,000×g, and the supernatant was subjected to ultracentrifugation at 10,000×g. The resulting sediment was collected as a murine hepatic microsome fraction, and this fraction was adjusted so as to have a protein concentration of 5 mg/ml using buffer A. Thus, an enzyme source of the ACAT2 enzyme protein was obtained.

[Method for Measurement of Inhibitory Activity Against ACAT2]

ACAT2 activity was measured in the manner described below. A sample containing the above-described enzyme source (200 µg as protein), 200 mM bovine serum albumin, [1-$^{14}$C] oleoyl coenzyme A (final concentration: 170 µM, 0.090 µCi), and the given amounts of compounds prepared in Examples and Comparative Examples was added to buffer A, and the total amount of the mixture was adjusted to 200 µl to obtain a reaction solution. The reaction solution was incubated at 37° C. for 5 minutes. A reaction solution prepared with the addition of 10 µl of methanol in place of the sample was used as a control reaction solution.

After the incubation, the reaction was terminated with the addition of 1.2 ml of a chloroform/methanol (1:2) solution to the reaction solution. Thereafter, the lipid was collected from the reaction solution in accordance with the method of Blish & Dyer (Blish & Dyer, Can. J. Biochem. Physiol., Vol. 37, pp. 911-917, 1959). The resulting chloroform layer was evaporated to dryness and spotted on a thin layer chromatography (TLC) plate (silica gel plate, 0.5 mm thickness, Merck). Separation was carried out with the use of a solvent comprising hexane/diethyl ether/acetic acid (70:30:1, v/v).

Subsequently, [$^{14}$C] cholesteryl oleate separated on the TLC plate was quantified using FLA 7000 (Fuji Film). The results of measurements of the samples comprising compounds of Examples or Comparative Examples were compared with the results of measurement of the control sample to determine the inhibitory activity of the samples comprising compounds of Examples or Comparative Examples against ACAT2 based on the equation shown below. In quantification of the [$^{14}$C] cholesteryl oleate, the radioactivity of a TLC plate onto which no substance had been spotted was designated as the background level.

$$\text{Inhibitory activity} = 100 - \frac{(\text{radioactivity of sample containing compound of Example or Comparative Example}) - (\text{background})}{(\text{radioactivity of control}) - (\text{background})}$$

On the basis of the inhibitory activity determined in the manner described above, the concentration of the compounds of the examples or comparative examples at which 50% inhibition of the ACAT2 activity was achieved (IC$_{50}$) was calculated. The results are shown in Table 1. The symbols used in the table are as defined below.
***: 0.5 μM≥inhibitory activity
**: 10 μM≥inhibitory activity >0.5 μM
*: 100 μM≥inhibitory activity >10 μM
Inhibitory activity: the concentration at which 50% inhibition of the ACAT2 activity was achieved (IC$_{50}$)

TABLE 1

| Compound No. | Inhibitory activity |
|---|---|
| PT001 | * |
| PT002 | * |
| PT003 | * |
| PT004 | ** |
| PT005 | *** |
| PT006 | *** |
| PT007 | ** |
| PT008 | ** |
| PT009 | *** |
| PT010 | * |
| PT017 | *** |
| PT022 | *** |
| Pyripyropene A (Comparative Example) | *** |

As shown in Table 1, all the compounds of the examples exhibited a higher degree of inhibitory activity against ACAT2. In particular, the compounds of the examples corresponding to the compound represented by Formula (I) according to the present invention, PT005, PT006, PT009, PT017, and PT022, exhibited a very higher degree of inhibitory activity against ACAT2, which is substantially equivalent to that of pyripyropene A. Accordingly, it was demonstrated that the compound having an inhibitory activity against ACAT2 according to the present invention could be produced via a synthetic means without the use of a naturally occurring material; i.e., pyripyropene A, as a starting material.

It should be noted that the present invention is not limited to the examples described above, and various modifications are within the scope of the present invention. For example, the examples described above are provided so as to precisely explain the present invention, and the present invention does not necessarily encompass all the constitutions described. In addition, other constitutions may be added to, deleted from, and/or substituted with part of the constitutions of the examples.

All publications, patents, and patent applications cited herein are incorporated herein by reference in their entirety.

The invention claimed is:
1. A compound represented by Formula (I):

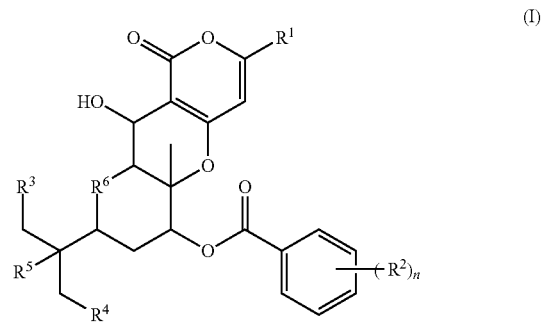

wherein
R$^1$ represents substituted or unsubstituted cycloalkyl, substituted or unsubstituted aryl, substituted or unsubstituted heterocycloalkyl, or substituted or unsubstituted heteroaryl;
n is an integer from 0 to 5;
R$^2$ represents halogen, cyano, nitro, substituted or unsubstituted alkyl, substituted or =substituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted aryl, substituted or unsubstituted arylalkyl, substituted or unsubstituted arylalkenyl, substituted or unsubstituted heteroaryl, substituted or unsubstituted heteroarylalkyl, substituted or unsubstituted alkoxy, substituted or unsubstituted cycloalkoxy, substituted or unsubstituted heterocycloalkoxy, substituted or unsubstituted aryloxy, substituted or unsubstituted arylalkyloxy, substituted or unsubstituted arylalkenyloxy, substituted or =substituted heteroaryloxy, substituted or unsubstituted heteroarylalkyloxy, substituted or unsubstituted acyl, or —NR$^{N1}$R$^{N2}$, provided that, when n is an integer from 2 or greater, each R$^2$ group may be the same or different;
R$^{N1}$ and R$^{N2}$ each independently represent a monovalent group selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted aryl, substituted or unsubstituted arylalkyl, substituted or unsubstituted arylalkenyl, substituted or unsubstituted heteroaryl, substituted or unsubstituted heteroarylalkyl, substituted or unsubstituted alkoxy, substituted or unsubstituted cycloalkoxy, substituted or unsubstituted heterocycloalkoxy, substituted or unsubstituted aryloxy, substituted or unsubstituted arylalkyloxy, substituted or unsubstituted arylalkenyloxy, substituted or unsubstituted heteroaryloxy, substituted or unsubstituted heteroarylalkyloxy, and substituted or unsubstituted acyl;

$R^3$ and $R^4$ each independently represent hydrogen, hydroxyl, substituted or unsubstituted alkylcarbonyloxy, substituted or unsubstituted arylcarbonyloxy, or substituted or unsubstituted alkoxy, or $R^3$ and $R^4$ together form —O—CR$^7$R$^8$—O—;

$R^5$ represents hydrogen, hydroxyl, substituted or unsubstituted alkylcarbonyloxy, substituted or unsubstituted arylcarbonyloxy, or substituted or unsubstituted alkoxy;

$R^6$ represents —C(CH$_3$)$_2$— or —CH$_2$—; and $R^7$ and $R^8$ each independently represent hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted aryl, substituted or unsubstituted arylalkyl, substituted or unsubstituted arylalkenyl, substituted or unsubstituted heteroaryl, or substituted or unsubstituted heteroarylalkyl, wherein when the aforementioned groups are substituted, the substituents each independently represent a monovalent group selected from the group consisting of halogen, cyano, nitro, unsubstituted alkyl, unsubstituted alkenyl, unsubstituted alkynyl, unsubstituted alkynyl, unsubstituted cycloalkyl, unsubstituted cycloalkenyl, unsubstituted cycloalkynyl, unsubstituted amino, and unsubstituted alkoxy;

or a salt thereof, or a solvate thereof.

2. The compound according to claim 1, wherein $R^1$ represents substituted or unsubstituted aryl or substituted or unsubstituted heteroaryl;

$R^2$ represents halogen, cyano, nitro, substituted or unsubstituted alkyl, substituted or unsubstituted alkenyl, or substituted or unsubstituted alkynyl; and $R^7$ and $R^8$ each independently represent hydrogen, substituted or unsubstituted alkyl, substituted or unsubstituted alkenyl, substituted or unsubstituted alkynyl, or substituted or unsubstituted aryl.

3. The compound according to claim 1, wherein $R^2$ represents a cyano group.

4. The compound according to claim 1, wherein n is the integer 1; and $R^2$ represents a 4-cyano group.

5. A method for producing the compound according to claim 1 comprising:

epoxidizing a compound represented by Formula (II):

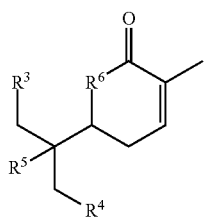
(II)

wherein $R^3$, $R^4$, $R^5$, and $R^6$ are as defined in claim 1, to obtain a compound represented by Formula (III):

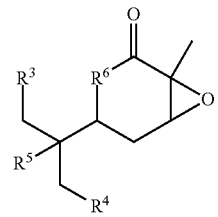
(III)

wherein $R^3$, $R^4$, $R^5$, and $R^6$ are as defined in claim 1;

introducing an aldehyde group into the compound represented by Formula (III) obtained by the step of epoxidation to obtain a compound represented by Formula (IV):

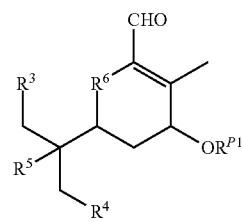
(IV)

wherein $R^3$, $R^4$, $R^5$, and $R^6$ are as defined in claim 1, and $R^{P1}$ represents a hydroxyl protecting group;

a step of C ring introduction increasing the number of carbon atoms of the compound represented by Formula (IV) obtained by the step of aldehyde group introduction and subjecting it to cyclization, so as to obtain a compound represented by Formula (V):

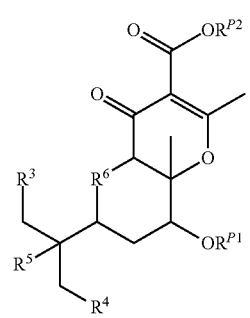
(V)

wherein $R^3$, $R^4$, $R^5$, and $R^6$; are as defined in claim 1 and $R^{P1}$ represents a hydroxyl protecting group, and $R^{P2}$ represents a carboxylic acid protecting group;

a step of D ring introduction subjecting the compound represented by Formula (V) obtained by the step of C ring introduction to cyclization, so as to obtain a compound represented by Formula (VII):

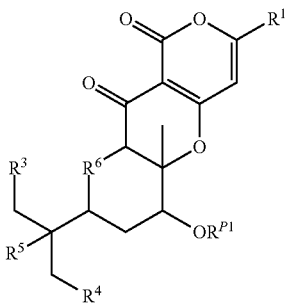

(VII)

wherein $R^1$, $R^3$, $R^4$, $R^5$, $R^6$ are as defined in claim 1 and $R^{P1}$ represents a hydroxyl protecting group;

a step of benzoyl group introduction allowing the compound represented by Formula (VII) obtained by the step of D ring introduction to react with a compound represented by Formula (VIII):

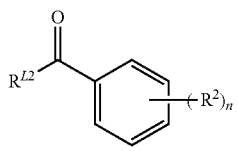

(VIII)

wherein $R^2$ and n are as defined in claim 1; and $R^{L2}$ represents a carboxylic acid protecting group, to obtain a compound represented by Formula (IX):

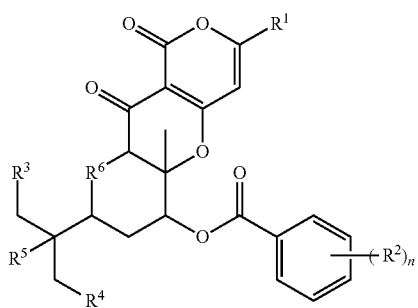

(IX)

wherein $R^1$, $R^2$, $R^3$, $R^4$, $R^5$, $R^6$, and n are as defined in claim 1; and a step of reduction reducing a carbonyl group at position 10 of the compound represented by Formula (IX) obtained by the step of benzoyl group introduction to obtain the compound represented by Formula (I).

6. A pharmaceutical composition comprising the compound according to claim 1 or a pharmaceutically acceptable salt thereof, or a pharmaceutically acceptable solvate thereof, and one or more pharmaceutically acceptable carriers.

7. The pharmaceutical composition according to claim 6 for use in the treatment of one or more diseases or symptoms selected from the group consisting of hyperlipemia, arteriosclerosis, fatty liver, and obesity.

8. A method for the treatment of diseases or symptoms selected from the group consisting of hyperlipemia, arteriosclerosis, fatty liver, and obesity comprising administering an effective amount of the compound according to claim 1 or a pharmaceutically acceptable salt thereof, or a pharmaceutically acceptable solvate thereof to a subject who is in need of treatment of the diseases or symptoms.

9. The compound according to claim 1, wherein $R^1$ represents unsubstituted aryl or unsubstituted heteroaryl;

$R^2$ represents halogen, cyano, nitro, unsubstituted alkyl, unsubstituted alkenyl, or unsubstituted alkynyl;

$R^3$ and $R^4$ each independently represent hydrogen, hydroxyl, unsubstituted alkylcarbonyloxy, unsubstituted arylcarbonyloxy, or unsubstituted alkoxy, or $R^3$ and $R^4$ together form —O—$CR^7R^8$—O—;

$R^5$ represents hydrogen, hydroxyl, unsubstituted alkylcarbonyloxy, unsubstituted arylcarbonyloxy, or unsubstituted alkoxy;

$R^6$ represents —$C(CH_3)_2$— or —$CH_2$—; and $R^7$ and $R^8$ each independently represent hydrogen, unsubstituted alkyl, unsubstituted alkenyl, unsubstituted alkynyl, or substituted or unsubstituted aryl, when the aryl has been substituted, the substituent represents unsubstituted alkyl.

10. The compound according to claim 1, wherein $R^1$ represents phenyl or pyridin-3-yl;

n is 1;

$R^2$ represents 4-cyano;

$R^3$ and $R^4$ each independently represent hydrogen or acetoxy or together form —O—$CR^7R^8$—O—;

$R^5$ represents hydrogen;

$R^6$ represents —$C(CH_3)_2$— or —$CH_2$—;

$R^7$ represents hydrogen; and $R^8$ represents 2-methylphenyl.

11. The compound according to claim 1, which is selected from the group consisting of the following compounds:

(5aS,6S,8S,9aS,10R)-10-hydroxy-8-isopropyl-5a-methyl-1-oxo-3-(pyridin-3-yl)-1,5a,6,7,8,9,9a,10-octahydropyrano[4,3-b]chromen-6-yl 4-cyanobenzoate ((10R)-8) (PT005);

(5aS,6S,8S,9aS,10 S)-10-hydroxy-8-isopropyl-5a-methyl-1-oxo-3-(pyridin-3-yl)-1,5a,6,7,8,9,9a,10-octahydropyrano[4,3-b]chromen-6-yl 4-cyanobenzoate ((10S)-8) (PT006);

(5aS,6S,8S,9aS,10R)-10-hydroxy-8-isopropyl-5a-methyl-1-oxo-3-phenyl-1,5a,6,7,8,9,9a,10-octahydropyrano[4,3-b]chromen-6-yl 4-cyanobenzoate (34) (PT007);

(5aS,6S,8S,9aS,10R)-10-hydroxy-8-isopropyl-5a,9,9-trimethyl-1-oxo-3-(pyridin-3-yl)-1,5a,6,7,8,9,9a,10-octahydropyrano[4,3-b]chromen-6-yl 4-cyanobenzoate (15) (PT009);

(5aS,6S,8S,9aS,10R)-10-hydroxy-5a,9,9-trimethyl-1-oxo-3-(pyridin-3-yl)-8-(2-(o-toluyl)-1,3-dioxan-5-yl)-1,5a,6,7,8,9,9a,10-octahydropyrano[4,3-b]chromen-6-yl 4-cyanobenzoate (PTO 17); and 2-((5aS,6S,8S,9aS,10R)-6-((4-cyanobenzoyl)oxy)-10-hydroxy-5a,9,9-trimethyl-1-oxo-3-(pyridin-3-yl)-1,5a,6,7,8,9,9a,10-octahydropyrano[4,3-b]chromen-8-yl)propane-1,3-diyl diacetate (PT022).

* * * * *